United States Patent
Reuveni et al.

(10) Patent No.: US 8,637,575 B2
(45) Date of Patent: *Jan. 28, 2014

(54) MODULATORS OF PROTEIN KINASE SIGNALING

(75) Inventors: Hadas Reuveni, Har Adar (IL); Alexander Levitzki, Jerusalem (IL); Revital Sasson, Gan Yavne (IL); Andre C. B. Lucassen, Rehovot (IL)

(73) Assignee: Novotyr Therapeutics Ltd., Kiryat Shmona (IL)

( * ) Notice: Subject to any disclaimer, the term of this patent is extended or adjusted under 35 U.S.C. 154(b) by 117 days.

This patent is subject to a terminal disclaimer.

(21) Appl. No.: 12/995,669

(22) PCT Filed: Jun. 7, 2009

(86) PCT No.: PCT/IL2009/000568
§ 371 (c)(1),
(2), (4) Date: Dec. 1, 2010

(87) PCT Pub. No.: WO2009/147682
PCT Pub. Date: Dec. 10, 2009

(65) Prior Publication Data
US 2011/0105618 A1    May 5, 2011

Related U.S. Application Data

(60) Provisional application No. 61/058,943, filed on Jun. 5, 2008.

(51) Int. Cl.
*A61K 31/165*    (2006.01)
*C07C 327/44*    (2006.01)
*C07D 277/36*    (2006.01)

(52) U.S. Cl.
USPC .............................. 514/599; 435/325; 564/74

(58) Field of Classification Search
None
See application file for complete search history.

(56) References Cited

U.S. PATENT DOCUMENTS

| | | | |
|---|---|---|---|
| 5,217,999 A | 6/1993 | Levitzki | |
| 5,302,606 A | 4/1994 | Spada | |
| 5,691,362 A | 11/1997 | McCormick | |
| 5,773,476 A | 6/1998 | Chen | |
| 6,020,332 A | 2/2000 | Li | |
| 6,225,335 B1 | 5/2001 | Tang | |
| 6,525,046 B1 | 2/2003 | Cirillo | |
| 8,058,309 B2 * | 11/2011 | Reuveni et al. | 514/464 |
| 2004/0127555 A1 | 7/2004 | Snow | |
| 2004/0197335 A1 | 10/2004 | Slavin | |
| 2009/0143397 A1 | 6/2009 | Kuo | |
| 2012/0083528 A1 * | 4/2012 | Reuveni et al. | 514/523 |

FOREIGN PATENT DOCUMENTS

| | | |
|---|---|---|
| CN | 1155977 | 8/1997 |
| CN | 1167568 | 12/1997 |
| EP | 0860438 B2 | 8/1998 |
| EP | 1340500 B2 | 9/2003 |
| WO | 95/24190 A1 | 9/1995 |
| WO | 97/45111 A1 | 12/1997 |
| WO | 97/45400 A1 | 12/1997 |
| WO | 99/24442 A1 | 5/1999 |
| WO | 00/43384 A1 | 7/2000 |
| WO | 01/68593 A1 | 9/2001 |
| WO | 03/045378 A1 | 6/2003 |
| WO | 03/053425 A1 | 7/2003 |
| WO | 03/072570 A1 | 9/2003 |
| WO | 2005/068414 A1 | 7/2005 |
| WO | 2005/077942 A1 | 8/2005 |
| WO | 2007/072041 A1 | 6/2007 |
| WO | 2008/068751 A1 | 6/2008 |

OTHER PUBLICATIONS

Aaronson, S. A., "Growth factors and cancer", Science, 254(5035):1146-1153 (1991).
Baserga, Renato, "The insulin receptor substrate-1: A biomarker for cancer?", Exp Cell Res. 315(5):727-732 (2009).
Berge, Stephen M. et al., "Pharmaceutical salts", J. Pharm. Sci., 66(1):1-19 (1977).
Blum, Galia et al., "Substrate Competitive Inhibitors of IGF-1 Receptor Kinase", Biochem, 39(51):15705-15712 (2000).
Gazit, A. et al., "Tyrphostins I: synthesis and biological activity of protein tyrosine kinase inhibitors", J. Med. Chem., 32(10):2344-2352 (1989).
Goodson, J. Max, "Dental applications", Medical Applications of Controlled Release, 2:115-138 (1984).
Langer, Robert, "New methods of drug delivery", Science, 249(4976):1527-1533 application (1990).
Levitzki, Alexander, "Tyrphostins—potential antiproliferative agents and novel molecular tools", Biochem. Pharmcol., 40(5):913-920 (1990).
Levitzki, Alexander, "Tyrphostins: tyrosine kinase blockers as novel antiproliferative agents and dissectors of signal transduction", FASEB J., 6(14):3275-3282 (1992).
Levitzki, Alexander and Gazit, Aviv, "Tyrosine kinase inhibition: an approach to drug development", Science, 267(5205):1782-88 (1995).
Posner, Israel et al., "Kinetics of inhibition by tyrphostins of the tyrosine kinase activity of the epidermal growth factor receptor and analysis by a new computer program", Mol. Pharmacol., 45(4):673-683 (1994).
Ryan, Paula D. and Goss, Paul E., "The emerging role of the insulin-like growth factor pathway as a therapeutic target in cancer", The Oncologist, 13(1):16-24 (2008).

(Continued)

*Primary Examiner* — Kamal Saeed
(74) *Attorney, Agent, or Firm* — Rodney J. Fuller; Booth Udall Fuller, PLC

(57) ABSTRACT

The present invention provides new tyrphostin derivatives acting as protein kinase (PK) and receptor kinase (RK) signaling modulators. The invention further provides methods of their preparation, pharmaceutical compositions including such compounds, and methods of using these compounds and compositions, especially as chemotherapeutic agents for preventions and treatments of PK and RK related disorders such as metabolic, inflammatory, fibrotic, and cell proliferative disorders, in particular cancer.

20 Claims, 19 Drawing Sheets

(56) References Cited

OTHER PUBLICATIONS

Saudek, Christopher D. et al., "A preliminary trial of the programmable implantable medication system for insulin delivery", Engl. Med., 321(9):574-579 (1989).
Schlessinger, Joseph, "Signal transduction by allosteric receptor oligomerization". Trends Biochem Sci., 13(11):443-447 (1988).
Schlessinger, J. and Ullrich, A., "Growth factor signaling by receptor tyrosine kinases", Neuron, 9(3):383-391 (1992).
Steiner, Lilach et al., "ATP non-competitive IGF-1 receptor kinase inhibitors as lead anti-neoplastic and anti-papilloma agents", Eur J Pharmacol., 562(1-2):1-11 Epub Feb. 3, 2007 (2007).
Treat, Joseph et al., "Liposome encapsulated doxorubicin preliminary results of phase I and phase II trials", Liposomes in the Therapy of Infectious Disease and Cancer (1989) Lopez-Berestein and Fidler (eds.), Alan R. Liss, NY, 353-365 (1989).
Ullrich, Axel and Schlessinger, Joseph, "Signal transduction by receptors with tyrosine kinase activity", Cell, 61(2):203-212 (1990).
Yaish, Pnina et al., "Blocking of EGF-dependent cell proliferation by EGF receptor kinase inhibitors", Science, 242(4880):933-935 (1988).
Yoneda, Toshiuki et al., "The antiproliferative effects of tyrosine kinase inhibitors tyrphostins on a human squamous cell carcinoma in vitro and in nude mice", Cancer Res., 51(16):4430-4435 (1991).
International Search Report and written opinion of PCT/IL09/00568 mailed Sep. 29, 2009.
Bäckström et al., (1989) Synthesis of some novel potent and selective catechol O-methyltransferase inhibitors. J Med Chem 32(4): 841-846.
Gazit et al., (1991) Tyrphostins. 2. Heterocyclic and alpha-substituted benzylidenemalononitrile tyrphostins as potent inhibitors of EGF receptor and ErbB2/neu tyrosine kinases. J Med Chem 34(6): 1896-1907.
Mazumder et al., (1995) Effects of tyrphostins, protein kinase inhibitors, on human immunodeficiency virus type 1 integrase. Biochemistry 34(46): 15111-15122.
Yuan and Parrill (2000) QSAR development to describe HIV-1 integrase inhibition. Journal of Molecular Structure: THEOCHEM 529: 273-282.

\* cited by examiner

MODULATORS OF PROTEIN KINASE SIGNALING

RELATED APPLICATION DATA

This application is the U.S. National Stage of PCT/IL2009/000568, filed Jun. 7, 2009, which claims priority to U.S. Provisional Patent Application No. 61/058,943, filed Jun. 5, 2008, the contents of each of which are herein incorporated by reference for all purposes.

FIELD OF THE INVENTION

The present invention relates to novel compounds which modulate protein kinase signaling and their use in treatment of protein kinase related disorders. Methods for their preparation and methods of use thereof are provided.

BACKGROUND OF THE INVENTION

Protein kinases (PKs) are a family of enzymes, which are involved in a variety of cellular processes, including signal transduction and growth regulation. Protein kinases (PKs) remove the γ-phosphate from ATP and covalently attach it to one of three amino acids that have a free hydroxyl group on substrate proteins. Most kinases act on both serine and threonine, others act on tyrosine, and a number (dual specificity kinases) act on all three. These phosphorylation processes by PKs are key events in cellular signaling.

Receptor tyrosine kinases (RTKs) constitute one class of protein tyrosine kinases (PTKs). These kinases belong to a family of transmembrane proteins and have been implicated in cellular signaling pathways. The predominant biological activity of some receptor kinases is the stimulation of cell growth and proliferation, while other receptor tyrosine kinases are involved in inhibiting growth and promoting differentiation. In some instances, a single tyrosine kinase can inhibit, or stimulate, cell proliferation depending on the cellular environment in which it is expressed (Schlessinger and Ullrich, *Neuron* (1992), 9(3): 383-391). RTKs include receptors for platelet-derived growth factor (PDGF), fibroblast growth factor (FGF), hepatocyte growth factor (HGF), insulin, insulin-like growth factor 1 (IGF-1), nerve growth factor (NGF), vascular endothelial growth factor (VEGF), macrophage colony stimulating factor (M-CSF) and others.

Receptor tyrosine kinases are mainly composed of an extracellular glycosylated ligand binding domain, a transmembrane domain and a cytoplasmic catalytic domain that can phosphorylate tyrosine residues. Binding of a ligand to membrane-bound receptors induces the formation of receptor dimers and allosteric changes thus activating the intercellular kinase domains which further results self-phosphorylation (autophosphorylation and/or transphosphorylation) of the receptor on tyrosine residues. Receptor phosphorylation stimulates physical association of the activated receptor with target molecules. Some of the target molecules are, in turn, phosphorylated, a process which transmits the signal to the cytoplasm. The secondary signal transducer molecules generated by activated receptors, result in a signal cascade that regulates cell functions such as cell division or differentiation. Intracellular signal transduction is reviewed in Aaronson, *Science* (1991), 254: 1146-1153; Schlessinger, *J. Trends Biochem. Sci.* (1988), 13: 443-447; and Ullrich and Schlessinger, *Cell* (1990), 61: 203-212.

Various cell proliferative disorders have been associated with defects in pathways mediated by PTKs. Enhanced activities of PTKs resulting from overexpression of the normal kinase, upregulation of ligands of receptor tyrosine kinases or activating mutations, are a hallmark of many diseases which involve cellular proliferation, including cancer. Examples of specific receptor tyrosine kinases associated with cell proliferative disorders include platelet derived growth factor receptor (PDGFR), insulin-like growth factor 1 receptor (IGF-1R), epidermal growth factor receptor (EDFR), and the related HER2.

The involvement of PTKs in various diseases renders them as targets for antiproliferative drugs. Numerous PTK blockers have been described in the literature including proposed mechanisms of action (Levitzki et al., *Science* (1995), 267: 1782-88; and Posner et al., *Mol. Pharmacol.* (1994), 45: 673-683). A family of PTK inhibitors, named tyrphostins, designed to mimic the tyrosine substrate was disclosed in Levitzki et al., *Science* (1995), 267: 1782-88; Levitzki et al., *Biochem. Pharm.* (1990), 40: 913-920; Levitzki et al., *FASEB J.* (1992), 6: 3275-3282; U.S. Pat. Nos. 5,217,999 and 5,773,476. The pharmacophores of these tyrphostins, and in particular tyrphostins of the benzylidene malonitril type, are the hydrophilic catechol ring and the more lipophilic substituted cyano-vinyl radical. Kinetic studies have shown that some tyrphostin compounds are pure competitive inhibitors vis-à-vis tyrosine substrates whereas for the ATP binding site they act as non-competitive inhibitors (Yaish et al., *Science* (1988), 242: 933-935; and Gazit et al., *J. Med. Chem.* (1989), 32: 2344-2352). Nonetheless, many tyrphostins have shown competitive inhibition against both the substrate and ATP binding site (Posner et al., *Mol. Pharmacol.* (1994), 45: 673-683).

In a related group of tyrphostins, the hydrophilic catechol ring was exchanged by lipophilic dichloro- or dimethoxyphenyl groups, to yield EGFR kinase inhibitors, effective in the low micromolar range (Yoneda et al., *Cancer Res.* (1991), 51: 4430-4435).

WO 99/24442 discloses compounds for inhibiting intracellular signal transduction mediated by one or more molecular interactions involving a phosphotyrosine-containing protein. However, nowhere is there a specific teaching of a compound having an αβ-unsaturated thioamide.

WO 2008/068751 to some of the inventors of the present invention, discloses novel tyrphostins compounds having increased inhibitory properties of insulin-like growth factor 1 receptor (IGF1R), platelet derived growth factor receptor (PDGFR), epidermal growth factor receptor (EGFR), and IGF1R-related insulin receptor (IR) activation and signaling. There is yet an unmet need for tyrphostins compounds with increased inhibitory properties useful in the treatment of protein kinase related disorders.

SUMMARY OF THE INVENTION

The present invention relates to novel tyrphostins derivatives having increased inhibitory properties for use as inhibitors of protein kinase (PK) activity, activation and signaling in cells. These novel tyrphostin derivatives show inhibition of human cancer cell proliferation thus being potent for the treatment of diseases associated with altered or abnormal activity or signaling of protein kinases. Examples of such diseases are cell proliferative disorders including cancer and psoriasis.

As demonstrated herein, the novel tyrphostin compoundS of the present invention are potent inhibitors of insulin-like growth factor 1 receptor (IGF1R) and/or insulin receptor substrate 1 (IRS1) signaling. As such, these compounds are useful in inhibiting, treating or preventing an IGF1R and/or IRS1 signaling related disorder, for example cancer.

According to one aspect, the present invention provides compounds represented by the structure of formula 1:

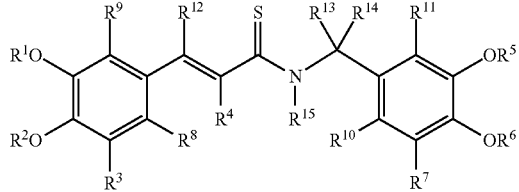

wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;

$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkyl-heterocyclyl, $(C_1$-$C_4)$-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;

provided that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; and $R^4$ is H or CN; then at least one of $R^8$-$R^{15}$ is not H, including salts, hydrates, solvates, polymorphs, optical isomers, geometrical isomers, enantiomers, diastereomers, and mixtures thereof.

According to some embodiments, the present invention provides compounds represented by the structure of formula 2 or 3:

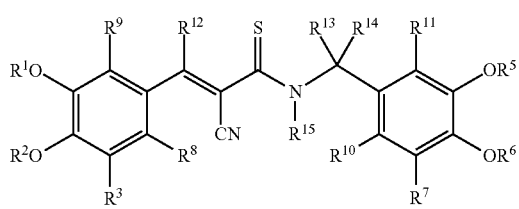

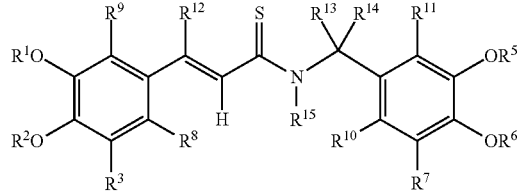

wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;

$R^3$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl; $(C_1$-$C_4)$-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;

provided that when $R^1$, $R^2$, $R^5$ and $R^6$ are H, $C_1$-$C_4$ alkyl, acyl or a functional group that gives rise to hydroxyl upon hydrolysis; and $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; then at least one of $R^8$-$R^{15}$ is not H, including salts, hydrates, solvates, polymorphs, optical isomers, geometrical isomers, enantiomers, diastereomers, and mixtures thereof.

In one embodiment, the present invention provides a compound represented by the structure of formula 1, 2 or 3 wherein $R^1$, $R^2$, $R^5$ and $R^6$ are each H or a functional group that gives rise to hydroxyl upon hydrolysis. In another embodiment, the present invention provides a compound represented by the structure of formula 1, 2, or 3 wherein $R^7$ is $OR^a$ and $R^1$, $R^2$, $R^5$, $R^6$, and $R^a$ are each H or a functional group that gives rise to hydroxyl upon hydrolysis. In yet another embodiment, the present invention provides a compound represented by the structure of formula 1, 2 or 3 wherein $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl or $C_1$-$C_4$ alkyl-$C_2$-$C_6$ alkynyl. In still another embodiment, one of $R^{13}$ and $R^{14}$ is H or $C_1$-$C_4$ alkyl. Each possibility represents a separate embodiment of the invention.

In particular embodiments, the present invention provides a compound represented by the structure of formula 1, wherein $R^4$, $R^{11}$, $R^{12}$, $R^{13}$, $R^{14}$ and $R^{15}$ are each H. In additional embodiments, substituents $R^{13}$, $R^{14}$ and $R^{15}$ are each H. Each possibility represents a separate embodiment of the invention.

In currently preferred embodiments, the present invention provides a compound represented by the structure of formula 1 wherein $R^3$, $R^4$, $R^7$, $R^8$, $R^9$, $R^{10}$, $R^{11}$, $R^{12}$, $R^{13}$ and $R^{14}$ are each H, halogen, haloalkyl, OH, $NO_2$, CN, or $CH_2SR^a$, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalcyl, aryl, heterocyclyl, heteroaiyl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In another currently preferred embodiment, substituents $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$, and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, (C -$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In certain embodiments, the present invention provides a compound represented by the structure of formula 1 wherein $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$ and $R^{14}$ and $R^{15}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$ or CN, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In some embodiments, $R^4$, $R^{11}$, $R^{12}$, $R^{13}$, $R^{14}$ and $R^{15}$ are each H or $C_1$-$C_4$ alkyl. In specific embodiments, $R^1$, $R^2$, $R^5$ and $R^6$ are each H or a functional group that gives rise to hydroxyl upon hydrolysis; $R^3$, $R^8$, and $R^9$ are each independently H, halogen, haloalkyl, or $CH_2SR^a$; $R^7$, $R^{10}$ and $R^{11}$ are each independently H, halogen, haloalkyl, OH or a functional group that gives rise to hydroxyl upon hydrolysis; and $R^4$, $R^{12}$, $R^{13}$, $R^{14}$ and $R^{15}$ are each H, or $C_1$-$C_4$ alkyl, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

In particular non-liming embodiments, $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen. In additional embodiments, $R^1$, $R^2$, $R^4$, $R^5$, $R^6$, $R^8$, $R^{10}$, $R^{12}$, $R^{13}$, $R^{14}$ and $R^{15}$ are each H; $R^7$ is OH; and at least one of $R^3$, $R^9$ and $R^{11}$ is halogen. Each possibility represents a separate embodiment of the invention.

It is to be understood for all compounds of the present invention, that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; and $R^4$ is H or CN; then at least one of $R^8$-$R^{15}$ is not H.

Representative and non-limiting examples of such structures are compounds selected from the group consisting of compounds 4-16:

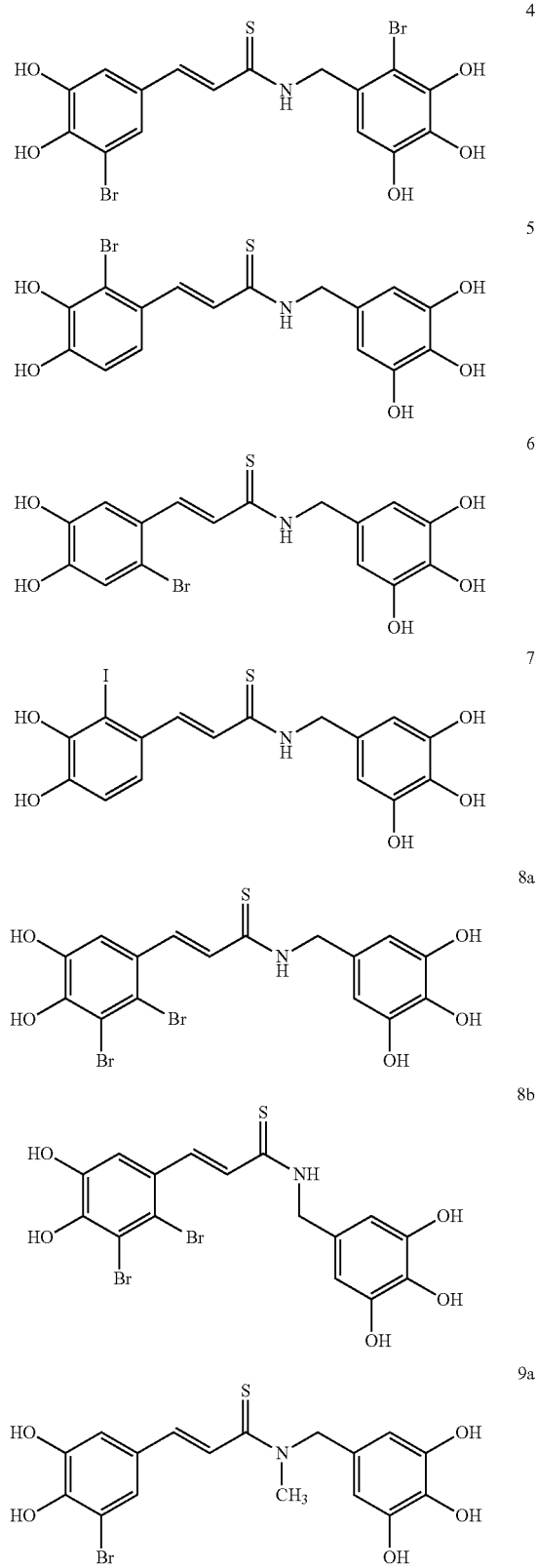

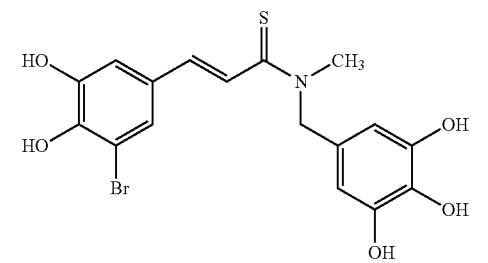

9b

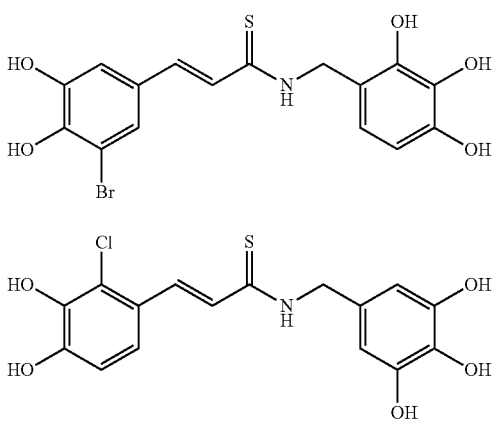

10

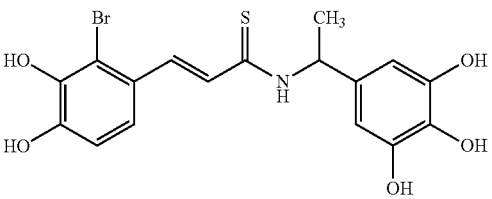

11

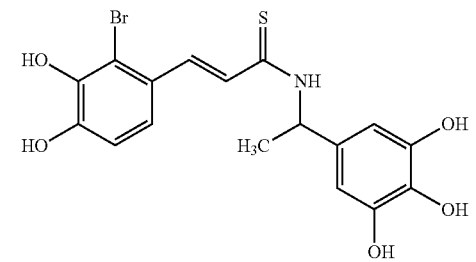

12a

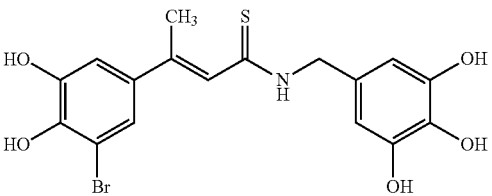

12b

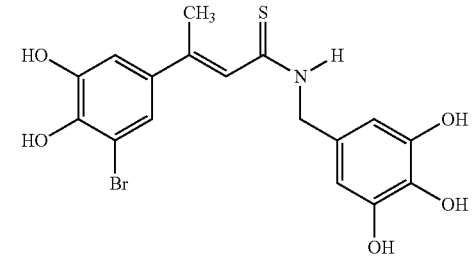

13a

13b

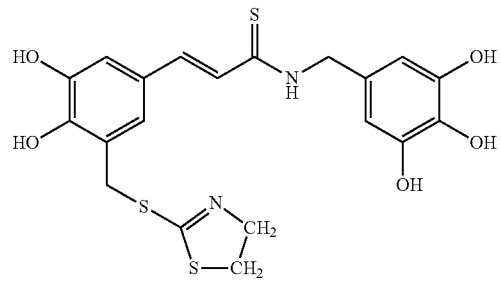

14

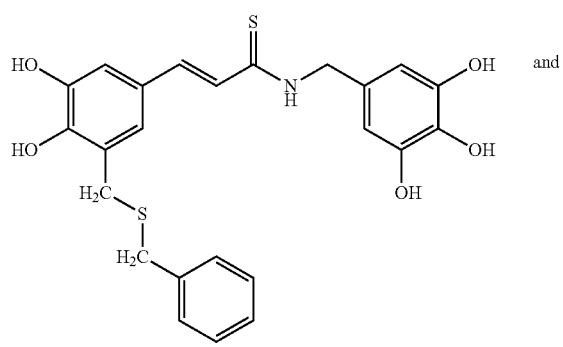

15

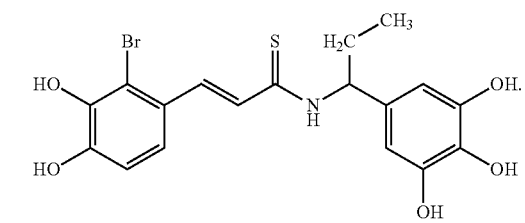

16

Although formulas 1-16 are drawn in a specific configuration, it is contemplated that the present invention encompasses all structural and geometrical isomers of such compounds, including cis, trans, E and Z isomers and optical isomers, independently at each occurrence.

The present invention further provides pharmaceutical compositions comprising a therapeutically effective amount of at least one compound represented by the structure of formula 1.

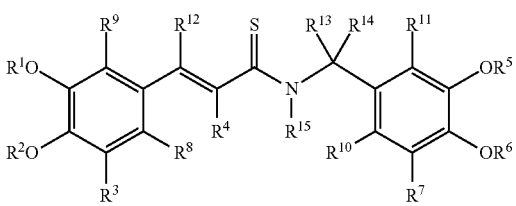

1 wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_n$H, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;

$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl; ($C_1$-$C_4$)-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;

provided that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; and $R^4$ is H or CN; then at least one of $R^8$-$R^{15}$ is not H, including salts, hydrates, solvates, polymorphs, optical isomers, geometrical isomers, enantiomers, diastereomers, and mixtures thereof; and a pharmaceutically acceptable carrier or excipient.

In particular embodiments, the preset invention provides pharmaceutical compositions comprising a therapeutically effective amount of at least one compound represented by the structure of formula 2 or 3

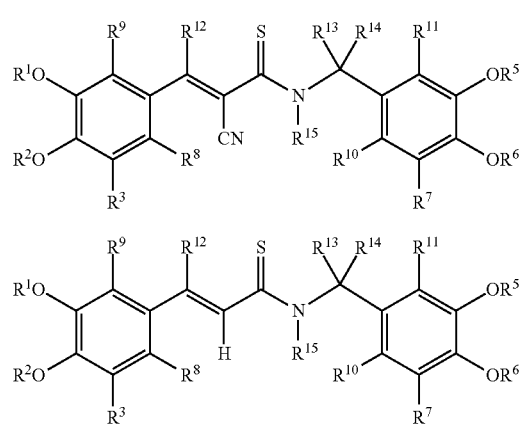

wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, acyl and a functional group that gives rise to hydroxyl upon hydrolysis;

$R^3$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl; ($C_1$-$C_4$)-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^bSR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;

provided that when $R^1$, $R^2$, $R^5$ and $R^6$ are H, $C_1$-$C_4$ alkyl, acyl or a functional group that gives rise to hydroxyl upon hydrolysis; and $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; then at least one of $R^8$-$R^{15}$ is not H, including salts, hydrates, solvates, polymorphs, optical isomers, geometrical isomers, enantiomers, diastereomers, and mixtures thereof; and a pharmaceutically acceptable carrier or excipient.

In currently preferred embodiments, the preset invention provides pharmaceutical compositions comprising a therapeutically effective amount of at least one of compounds 4-16 and a pharmaceutically acceptable carrier or excipient.

In yet another aspect, the present invention provides a method of inhibiting signal transduction mediated by a protein kinase (PK) in a cell, comprising contacting the cell with an effective inhibitory amount of at least one compound represented by the structure of formula 1, 2, or 3 or at least one of compounds 4-16.

In additional aspect, the present invention provides a method of inhibiting cell proliferation comprising contacting the cells with an effective inhibitory amount of at least one compound represented by the structure of formula 1, 2, or 3 or at least one of compounds 4-16.

In another embodiment, the present invention provides a method of inhibiting protein kinase (PK) activity, activation or signaling in a subject comprising the step of administering to the subject a therapeutically effective amount of at least one compound represented by the structure of formula 1, 2, or 3, or at least one of compounds 4-16. In currently preferred embodiments, the method comprises administering to the subject a pharmaceutical composition comprising a therapeutically effective amount of at least one compound represented by the structure of formula 1, 2, or 3, or at least one of compounds 4-16 and a pharmaceutically acceptable carrier or excipient.

In various embodiments, the present invention further provides a method of inhibiting, treating or preventing a protein kinase (PK) related disorder in a subject comprising the step of administering to the subject a therapeutically effective amount of at least one compound represented by the structure of formula 1, 2, or 3, or at least one of compounds 4-16. In other embodiments, the method comprises administering to the subject a pharmaceutical composition comprising a therapeutically effective amount of at least one compound represented by the structure of formula 1, 2, or 3, or at least one of compounds 4-16 and a pharmaceutically acceptable carrier or excipient. In one embodiment, the PK related disorder is a disorder related to receptor protein tyrosine kinase. The receptor protein tyrosine kinase, according to the principles of the present invention, is selected from a platelet-derived growth factor receptor (PDGFR), a fibroblast growth factor receptor (FGFR), a hepatocyte growth factor receptor (HGFR), an insulin receptor, an insulin-like growth factor-1 receptor (IGF-1R), an epidermal growth factor receptor (EGFR), a nerve growth factor receptor (NGFR), a vascular endothelial growth factor receptor (VEGFR), and a macrophage colony stimulating factor (M-CSFR). Each possibility represents a separate embodiment of the invention. In another embodiment, the present invention provides a method of inhibiting, treating or preventing an insulin-like growth factor 1 receptor (IGF1R) and/or insulin receptor substrate 1 (IRS1) signaling related disorder in a subject comprising the step of administering to said subject a therapeutically effective amount of at least one compound represented by the structure of formula 1, 2, or 3, or at least one of compounds 4-16.

In particular embodiments, the present invention provides a method of inhibiting, treating or preventing a protein kinase (PK) related disorder wherein the PK related disorder is selected from a cell proliferative disorder, a metabolic disorder, inflammatory disorder, or a fibrotic disorder. Each possibility represents a separate embodiment of the invention. In a currently preferred embodiment, the PK related disorder is cancer. In specific embodiments, the cancer is selected from the group consisting of ovarian cancer, prostate cancer, breast cancer, skin cancer, melanoma, colon cancer, lung cancer, pancreatic cancer, gastric cancer, bladder cancer, Ewing's sarcoma, lymphoma, leukemia, multiple myeloma, head and neck cancer, kidney cancer, bone cancer, liver cancer and thyroid cancer. Each possibility represents a separate embodiment of the invention.

Within the scope of the present invention are pharmaceutical compositions comprising at least one compound represented by the structure of formula 1, 2, or 3 or at least one of compounds 4-16 for inhibiting, treating or preventing a protein kinase (PK) related disorder in a subject. In various embodiments, the pharmaceutical compositions of the present invention are useful in inhibiting, treating or preventing an insulin-like growth factor 1 receptor (IGF1R) and/or insulin receptor substrate 1 (IRS1) signaling related disorder. In certain embodiments, the present invention provides the use of at least one compound represented by the structure of formula 1, 2, or 3 or at least one of compounds 4-16 for the preparation of a medicament for inhibiting, treating or preventing a protein kinase (PK) related disorder in a subject. In other embodiments, the compounds represented by the structure of formula 1, 2, or 3 or any of the compounds 4-16 are useful in treating or preventing an insulin-like growth factor 1 receptor (IGF1R) and/or insulin receptor substrate 1 (IRS1) signaling related disorder. In some embodiments, the use within the scope of the present invention comprises inhibiting, treating or preventing a disorder selected from the group consisting of a cell proliferative disorder, a metabolic disorder, inflammatory disorder and a fibrotic disorder. Each possibility represents a separate embodiment of the invention. In a currently preferred embodiment, the present invention provides the use of at least one compound represented by the structure of formula 1, 2, or 3 or at least one of compounds 4-16 for the preparation of a medicament for inhibiting, treating or preventing cancer.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
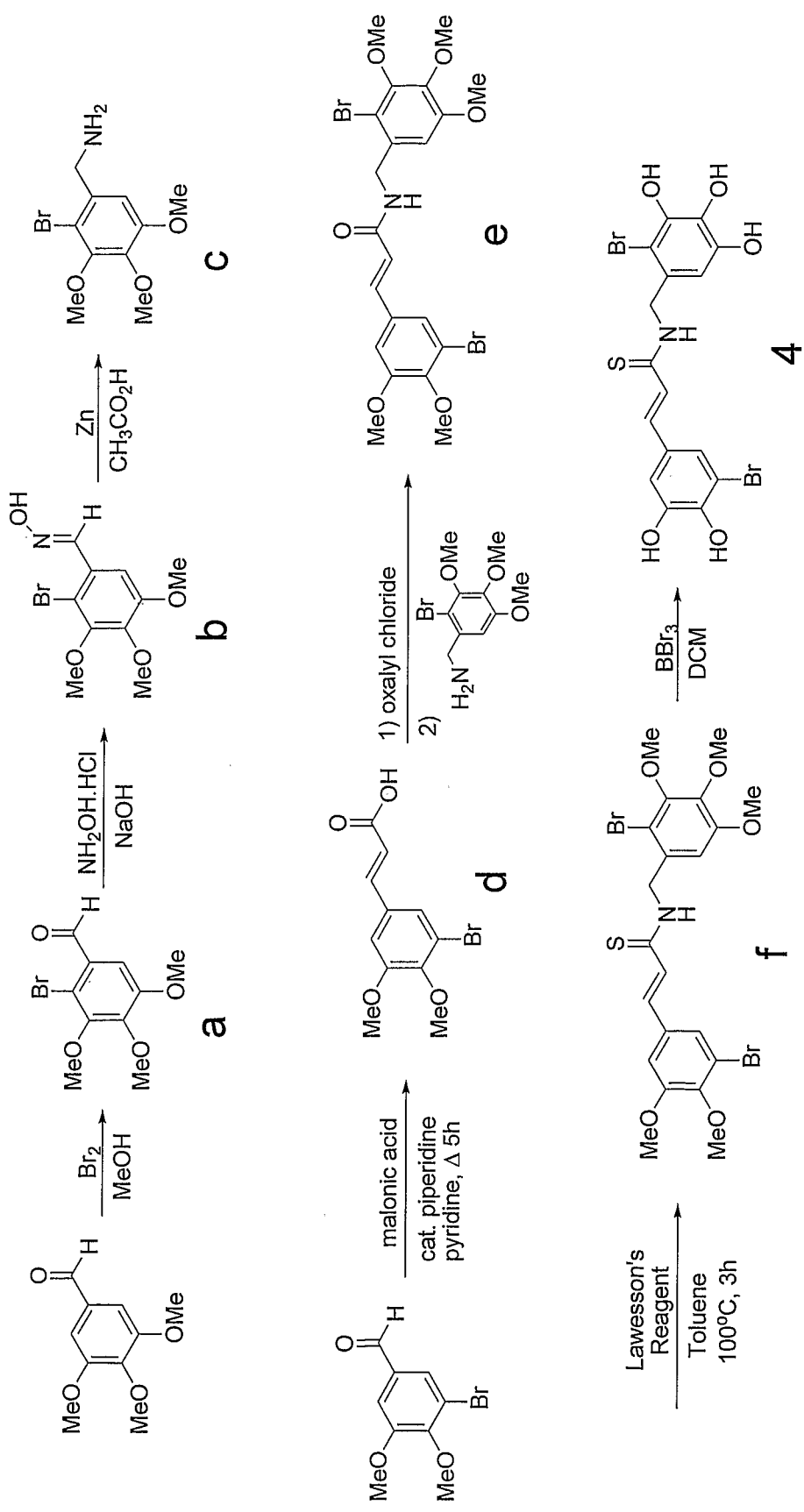
FIG. 1 Shows in schematic form an exemplary process for the synthesis of an exemplary novel Tyrphostin of the invention (compound 4).

The present invention relates to novel tyrphostin derivatives which are potent inhibitors of PK activity, activation and signaling. The compounds are useful in treating or preventing PK-related disorders, particularly those which are associated with defects in signaling pathways mediated by PKs. Exemplary PK-related disorders are cellular proliferation diseases including various types of cancers and psoriasis.

The compounds of the present invention are designed to have an enhanced inhibiting potency with respect to protein kinase (PK) signaling, compared with previously disclosed tyrphostin derivatives (Blum et al., *Biochem.* (2000), 39: 15705-15712; U.S. Pat. Nos. 5,773,476 and 5,217,999). The present invention is based in part on the unexpected finding that the introduction of additional substituents on the catechol phannacophore greatly enhances the inhibitory potency. Furthermore, introduction of additional substituents on the second aromatic ring and on the thioamide moiety were also found to significantly enhance the inhibiting potency of the new compounds.

The present invention provides compounds that are represented by the general formula structure of formula 1:

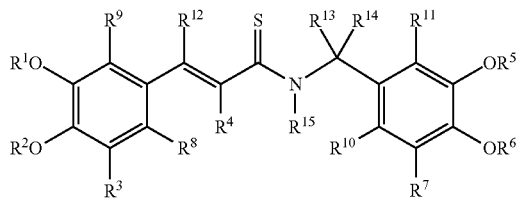

wherein
$R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, acyl and a functional group that gives rise to hydroxyl upon hydrolysis;
$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl; ($C_1$-$C_4$)-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis; and
$R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;
provided that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; and $R^4$ is H or CN; then at least one of $R^8$, $R^9$, $R^{10}$, $R^{11}$, $R^{12}$, $R^{13}$, $R^{14}$ and $R^{15}$ is not H,
including salts, hydrates, solvates, polymorphs, optical isomers, geometrical isomers, enantiomers, diastereomers, and mixtures thereof.

The present invention further provides compounds represented by the structure of formula 2 or 3:

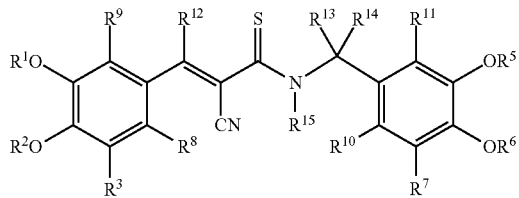

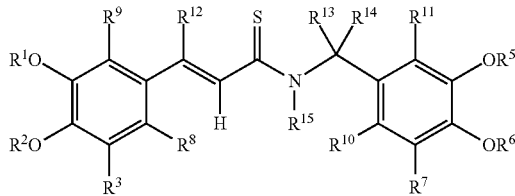

wherein
$R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, acyl and a functional group that gives rise to hydroxyl upon hydrolysis;
$R^3$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl; ($C_1$-$C_4$)-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis; and
$R^{15}$ is H, $C_1$-$C_4$ alkyl, $C_2$-$C_6$ alkenyl, $C_2$-$C_6$ alkynyl, alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;
provided that when $R^1$, $R^2$, $R^5$ and $R^6$ are H, $C_1$-$C_4$ alkyl, acyl or a functional group that gives rise to hydroxyl upon hydrolysis; and $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; then at least one of $R^8$, $R^9$, $R^{10}$, $R^{11}$, $R^{12}$, $R^{13}$, $R^{14}$ and $R^{15}$ is not H,
including salts, hydrates, solvates, polymorphs, optical isomers, geometrical isomers, enantiomers, diastereomers, and mixtures thereof.

The present invention further provides currently preferred embodiments wherein formula 1, 2 or 3 comprise the following substitutions with the proviso that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$, wherein $R^c$ is H, $C_1$-$C_4$ alkyl, acyl or a functional group that gives rise to hydroxyl upon hydrolysis; and $R^4$ is H or CN; then at least one of $R^8$, $R^9$, $R^{10}$, $R^{11}$, $R^{12}$, $R^{13}$, $R^{14}$ and $R^{15}$ is not H:

1. $R^1$, $R^2$, $R^5$ and $R^6$ are each H or a functional group that gives rise to hydroxyl upon hydrolysis.
2. $R^7$ is $OR^a$ and $R^1$, $R^2$, $R^5$, $R^6$, and $R^a$ are each H or a functional group that gives rise to hydroxyl upon hydrolysis.
3. $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl or $C_1$-$C_4$ alkyl-$C_2$-$C_6$ alkynyl.
4. $R^3$, $R^4$, $R^7$, $R^8$, $R^9$, $R^{10}$, $R^{11}$, $R^{12}$, $R^{13}$ and $R^{14}$ are each H, halogen, haloalkyl, OH, $NO_2$, CN, or $CH_2SR^a$, wherein $R^a$ and is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

5. $R^4$, $R^{11}$, $R^{12}$, $R^{13}$, $R^{14}$ and $R^{15}$ are each H.

6. $R^3$, $R^8$ and $R^9$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, halogen, haloalkyl, $NO_2$, $N_3$, $SO_2R^a$, $COOR^a$, $CSNR^aR^b$, $CSOR^a$, $OR^a$, $CONR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

7. $R^{12}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, heterocyclyl, heteroaryl, ($C_1$-$C_4$)-alkylaryl, ($C_1$-$C_4$)-alkylheterocyclyl, ($C_1$-$C_4$)-alkylheteroaryl, halogen, haloalkyl, $NO_2$, CN, $N_3$, $SO_2R^a$, $COOR^a$, $CSOR^a$, $OR^a$, $CONR^aR^b$, $CSNR^aR^b$, $NR^aR^b$ and $SR^a$, $CH_2SR^a$; wherein $R^a$ and $R^b$ are independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl; ($C_1$-$C_4$)-alkylheteroaryl, haloalkyl, $(CH_2CH_2O)_nH$, acyl or a functional group that gives rise to hydroxyl upon hydrolysis.

8. $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H, wherein $R^a$ and is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

9. $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$, $R^{14}$ and $R^{15}$ are each H or $C_1$-$C_4$ alkyl, wherein $R^a$ and is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

10. $R^1$, $R^2$, $R^5$ and $R^6$ are each H or a functional group that gives rise to hydroxyl upon hydrolysis; $R^3$, $R^8$, and $R^9$ are each independently H, halogen, haloalkyl, or $CH_2SR^a$; $R^7$, $R^{10}$ and $R^{11}$ are each independently H, halogen, haloalkyl, OH or a functional group that gives rise to hydroxyl upon hydrolysis; and $R^4$, $R^{12}$, $R^{13}$, $R^{14}$ and $R^{15}$ are each H, or $C_1$-$C_4$ alkyl, wherein $R^a$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, ($C_1$-$C_4$)-alkylaryl, ($C_1$-$C_4$)-alkylheterocyclyl, ($C_1$-$C_4$)-alkylheteroaryl, haloalkyl, $(CH_2CH_2O)_nH$, acyl or a functional group that gives rise to hydroxyl upon hydrolysis.

11. $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen.

12. $R^1$, $R^2$, $R^4$, $R^5$, $R^6$, $R^8$, $R^{10}$, $R^{12}$, $R^{13}$, $R^{14}$ and $R^{15}$ are each H; $R^7$ is OH; and at least one of $R^3$, $R^9$ and $R^{11}$ is halogen.

In some embodiments $R^{13}$, $R^{14}$ and $R^{15}$ are each H. In particular embodiments, one of $R^{13}$ and $R^{14}$ is H or $C_1$-$C_4$ alkyl.

Representative and non-limiting examples of such structures are compounds selected from the group consisting of compounds 4-16:

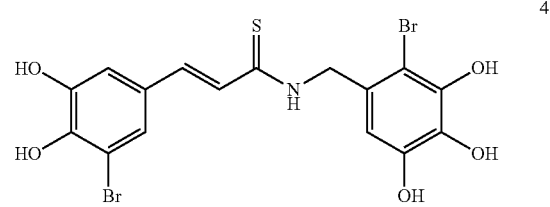

4

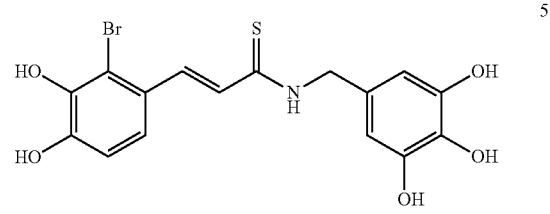

5

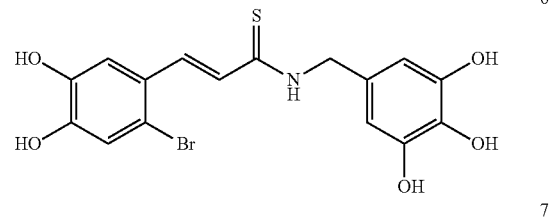

6

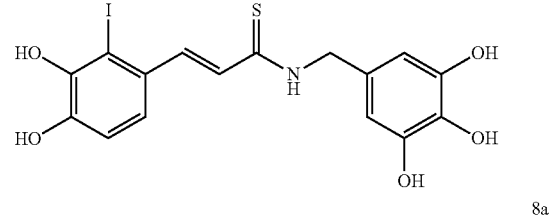

7

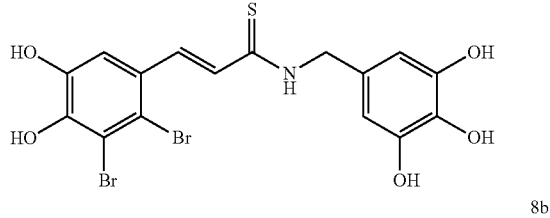

8a

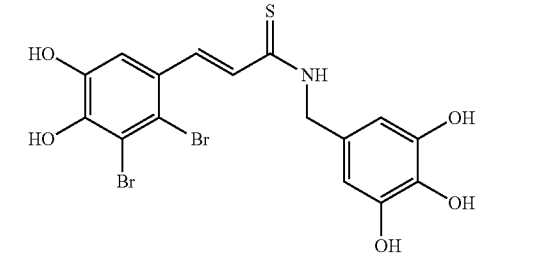

8b

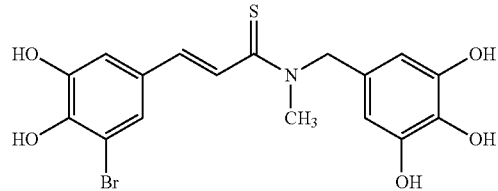
9a

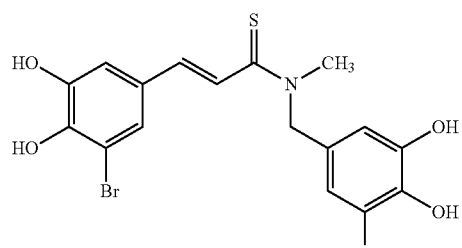
9b

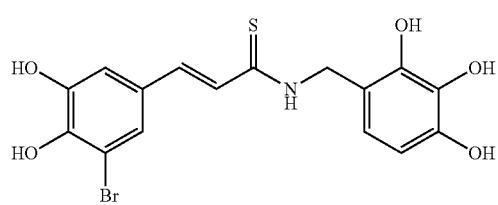
10

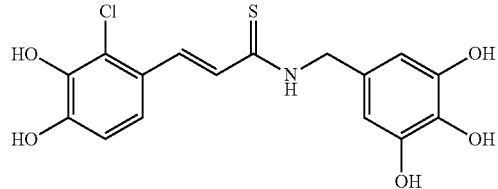
11

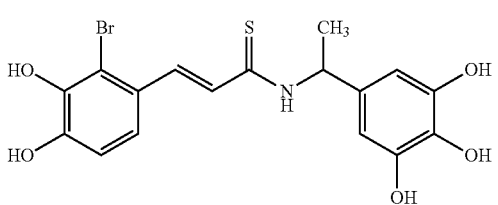
12a

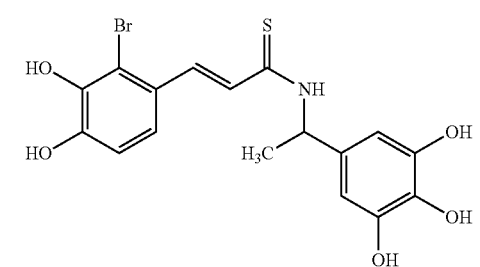
12b

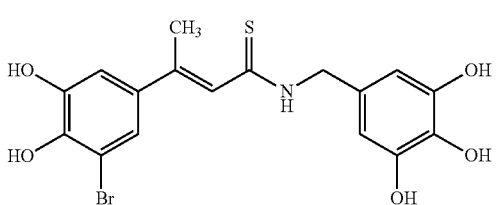
13a

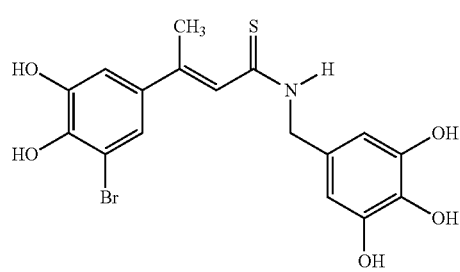
13b

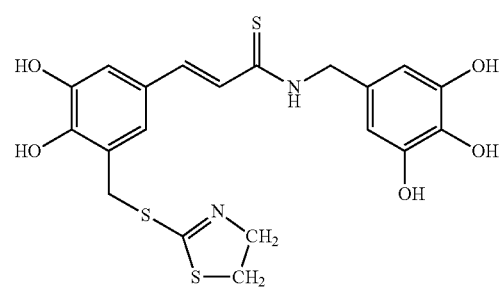
14

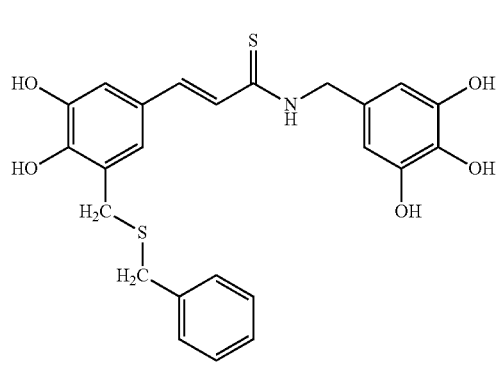
15

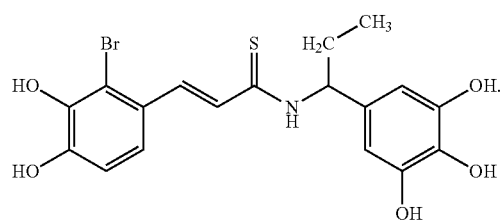
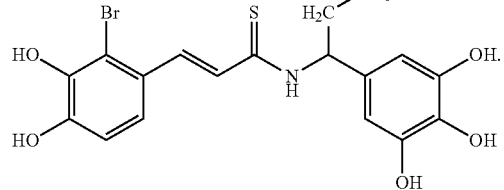
16 and

Although formulae 1-16 are drawn in a specific configuration, it is explicitly denoted that the compounds of the present invention encompass all structural and geometrical isomers including cis, trans, E and Z isomers and optical isomers, independently at each occurrence.

Chemical Definitions

An "alkyl" group refers to any saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms designated here as $C_2$-$C_8$-alkenyl. In another embodiment, the alkenyl group has 2-6 carbon atoms in the chain designated here as $C_2$-$C_6$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain designated here as $C_2$-$C_8$-alkynyl. In another embodiment, the alkynyl group has 2-6 carbon atoms in the chain designated here as $C_2$-$C_6$-alkynyl. Exemplary alkynyl groups include ethynyl, propynyl, n-butynyl, 2-butynyl, 3-methylbutynyl, n-pentynyl, heptynyl, octynyl and decynyl. The alkynyl group can be unsubstituted or substituted through available carbon atoms with one or more groups defined hereinabove for alkyl.

The term "$C_3$-$C_7$ cycloalkyl" used herein alone or as part of another group refers to any saturated or unsaturated (e.g., cycloalkenyl, cycloalkynyl) monocyclic or polycyclic group. Non-limiting examples of cycloalkyl groups are cyclopropyl, cyclobutyl, cyclopentyl, cyclohexyl or cycloheptyl. Non-limiting examples of cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group refers to a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. The heterocyclyl group can be unsubstituted or substituted through available atoms with one or more groups defined hereinabove for alkyl.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

A "hydroxy" group refers to an OH group. An "alkoxy" group refers to an —O-alkyl group wherein R is alkyl as defined above.

A "thio" group refers to an —SH group. An "alkylthio" group refers to an —SR group wherein R is alkyl as defined above.

An "amino" group refers to an $NH_2$ group. An alkylamino group refers to an —NHR group wherein R is alkyl is as defined above. A dialkylamido group refers to an —NRR' group wherein R and R' are alkyl as defined above.

An "amido" group refers to a —C(O)$NH_2$ group. An alkylamido group refers to an —C(O)NHR group wherein R is alkyl is as defined above. A dialkylamido group refers to an —C(O)NRR' group wherein R and R' are alkyl as defined above.

A "thioamide" group refers to a —C(S)NHR group, where R is either alkyl, aryl, alkylaryl or H.

A "polyoxyalkylene" group refers to a $(CH_2CH_2O)_nH$ group wherein n=1-20. Currently preferred polyoxyalkylene groups are polyethyleneglycol (PEG) and polypropyleneglycole.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

Examples of functional groups that give rise to hydroxyl upon hydrolysis include, but are not limited to, esters, anhydrides, carbamates, carbonates and the like. For example, when any of $R^1$, $R^2$, $R^5$ or $R^6$ is an acyl group (COR), the resulting functional group is an ester (OCOR). When any of $R^1$, $R^2$, $R^5$ or $R^6$ is an amide group (CONHR), the resulting functional group is a carbamate (OCONHR). When any of $R^1$, $R^2$, $R^5$ or $R^6$ is a carboxylate group (COOR), the resulting functional group is a carbonate (OCOOR).

Within the scope of the present invention are prodrugs of the compounds disclosed herein. The term "prodrug" represents compounds which are rapidly transformed in vivo to any of compounds represented by formula 1, 2 or 3 or any of compounds 4-16, for example by hydrolysis in the blood. Thus, the term "prodrug" refers to a precursor of any of the compounds of the present invention that is pharmaceutically acceptable. A prodrug may be inactive when administered to a subject, but is converted in vivo to an active compound. The use of prodrugs is particularly advantageous for facilitating the administration of the compounds. The prodrug compound often offers benefits of solubility, tissue compatibility or delayed release in a mammalian organism. For example the prodrug, according to the principles of the present invention, can be a compound represented by the structure of formula 1 wherein $R^1$, $R^2$, $R^5$ and $R^6$ are a functional group that gives rise to hydroxyl upon hydrolysis as defined hereinabove.

All stereoisomers of the compounds of the present invention are contemplated, either in admixture or in pure or substantially pure form. These compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, 1,L or d,1, D,L. In addition, several of the compounds of the present invention contain one or more double bonds. The present invention intends to encompass all structural and geometrical isomers including cis, trans, E and Z isomers and optical isomers, independently at each occurrence. The thioamides of the present invention occur in two isomeric forms known as atropisomers, due to hindered rotation around the thioamide bond. These isomers can interconvert in solution and ratios may vary at different conditions including temperature, pH, solvent, concentration etc. Where the interconversion is slow, the two isomers are drawn separately. Although formulae 1-7, 10-11 and 14-16 are drawn in one geometry, it is to be understood that these compounds encompass all geometrical isomers.

Within the scope of the present invention are intermediate compounds produced in the processes of preparing the compounds of the present invention. Specifically, intermediate compounds which are encompassed by the structure of formula 1 including, but not limited to, compounds f, i, l, o, r, t, t', v, y, ab, ab', ah, ah', al, ao, ar and ar', and therapeutic uses thereof, e.g., for treating cancer, are considered a part of the present invention.

One or more of the compounds of the invention, may be present as a salt. The term "salt" encompasses both basic and acid addition salts, including but not limited to carboxylate salts or salts with amine nitrogens, and include salts formed with the organic and, inorganic anions and cations discussed below. Further encompassed by the term are salts formed by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and the like.

The term "organic or inorganic cation" refers to counter-ions for the carboxylate anion of a carboxylate salt. The counter-ions are chosen from the alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference. Other cations encompassed by the above term include the protonated form of procaine, quinine and N-methylglucosamine. Furthermore, any zwitterionic form of the instant compounds formed by a carboxylic acid and an amino group are also contemplated.

The present invention also includes solvates of any of compounds represented by formula 1, 2 or 3 or any of compounds 4-16 and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of any of compounds represented by formula 1, 2 or 3 or any of compounds 4-16 and salts thereof. The term "polymorph" refers to a particular crystalline state of a substance, which can be characterized by particular physical properties such as X-ray diffraction, IR spectra, melting point, and the like.

Therapeutic Use

The present invention provides compounds and compositions effective at modulating protein kinase signaling. These compounds and compositions are potentially useful in the treatment of diseases associated with altered or abnormal activity or signaling of protein kinases such as enhanced activity or signaling of protein kinases.

Thus, in one embodiment, the present invention provides a method of inhibiting signal transduction mediated by a protein kinase (PK) in a cell comprising contacting the cell with an effective inhibitory amount of at least one compound represented by the structure of formula 1, 2, or 3, or at least one compound selected from compounds 4-16.

In another embodiment, the present invention provides a method of inhibiting cell proliferation comprising contacting the cells with an effective inhibitory amount of at least one compound represented by the structure of formula 1, 2, or 3 or at least one compound selected from compounds 4-16.

The present invention further provides a method of inhibiting, treating or preventing a protein kinase (PK) related disorder in a subject comprising the step of administering to the subject a therapeutically effective amount of at least one compound represented by the structure of formula 1, 2, or 3, or at least one compound selected from compounds 4-16. In another embodiment, the method comprises administering to the subject a pharmaceutical composition comprising a therapeutically effective amount of at least one compound represented by the structure of formula 1, 2, or 3, or at least one compound selected from compounds 4-16 and a pharmaceutically acceptable carrier or excipient.

The present invention further provides a method of inhibiting, treating or preventing an insulin-like growth factor 1 receptor (IGF1R) and/or insulin receptor substrate 1 (IRS1) signaling related disorder in a subject comprising the step of administering to the subject a therapeutically effective amount of at least one compound represented by the structure of formula 1, 2, or 3, or at least one compound selected from compounds 4-16. In another embodiment, the method comprises administering to the subject a pharmaceutical composition comprising a therapeutically effective amount of at least one compound represented by the structure of formula 1, 2, or 3, or at least one compound selected from compounds 4-16; and a pharmaceutically acceptable carrier or excipient.

The present invention further provides the use of at least one compound represented by the structure of formula 1, 2, or 3 or at least one compound selected from compounds 4-16 for the preparation of a medicament for inhibiting, treating or preventing a protein kinase (PK) related disorder in a subject. Further provided is the use of these compounds for the preparation of a medicament for treating or preventing an insulin-like growth factor 1 receptor (IGF1R) and/or insulin receptor substrate 1 (IRS1) signaling related disorder. Additional embodiments are the use of at least one compound represented by the structure of formula 1, 2, or 3 or at least one compound selected from compounds 4-16 for the preparation of a medicament for inhibiting signal transduction mediated by a protein kinase (PK). Additionally, these compounds are useful for the preparation of a medicament for inhibiting cell proliferation.

The pharmaceutical compositions comprising at least one compound represented by the structure of formula 1, 2, or 3 or at least one compound selected from compounds 4-16 in therapeutically effective amount and a pharmaceutically acceptable carrier or excipient are useful for inhibiting, treating or preventing a disorder selected from of a cell proliferative disorder, a metabolic disorder, inflammatory disorder and a fibrotic disorder. Each possibility represents a separate embodiment of the invention. In a currently preferred embodiment, the pharmaceutical compositions are useful for inhibiting, treating or preventing cancer and for inhibiting cell proliferation.

A "protein kinase" (PK) is a protein belonging to a family of enzymes that transfer the γ-phosphate of ATP and covalently attaching it to one of three amino acids that have a free hydroxyl group on substrate proteins. Most kinases act on both serine and threonine, others act on tyrosine, and a number (dual specificity kinases) act on all three. PKs are involved in a variety of key cellular processes, including signal transduction and growth regulation. A protein kinase, as used herein, refers to a receptor kinase (RK) as well as a cellular kinase (CK or non-receptor kinase). Thus the compounds of the present to invention are effective at inhibiting both receptor and non-receptor protein kinases or signaling thereof.

A cellular tyrosine kinase (CTK or non-receptor tyrosine kinase) is an intracellular protein which takes part in signal transduction within the cell, including signal transduction to the nucleus. Examples of CTKs are the Src family of oncoproteins. A receptor tyrosine kinase (RTK) is a transmembrane protein that participates in transmembrane signaling pathways. The predominant biological activity of some receptor tyrosine kinases is the stimulation of cell growth and proliferation, while other receptor tyrosine kinases are involved in arresting growth and promoting differentiation. RTKs include, but are not limited to, the receptors for platelet-derived growth factor (PDGF), fibroblast growth factor (FGF), hepatocyte growth factor (HGF), insulin, insulin-like growth factor-1 (IGF-1), nerve growth factor (NGF), vascular endothelial growth factor (VEGF), and macrophage colony stimulating factor (M-CSF).

The term "protein kinase related disorder" as used herein refers to a disorder characterized by abnormal or altered PK activity or signaling. Abnormal or altered activity or signaling further refers to either (i) increased or decreased PK activity or levels leading to aberrant cell proliferation, differentiation and/or growth; or (ii) any increase or decrease in the activity or levels of molecules downstream to the PK resulting in aberrant signaling of said PK. Over-activity of PKs refers to either overexpression of said PK in cells that do not normally express PKs, or increased PK expression leading to unwanted cell proliferation, differentiation and/or growth. Furthermore, over-activity of PKs can also refer to amplification of the gene encoding a particular PK or production of a level of PK activity which can correlate with cell proliferation, differentiation and/or growth. Over-activity can also be the result of ligand independent or constitutive activation as a result of mutations such as deletions of a fragment of a PK responsible for ligand binding. Over-activity can also be the result of deregulation of ligand levels and availability for binding and regulating the PK activity. Alternatively, aberrant increased or decreased PK activity can result from loss of upstream regulation of said PK, changes in PK localization or its interactions with additional signaling molecules. In addition, decreased PK expression can lead to unwanted reductions in cell proliferation, differentiation and/or growth. As defined above, the disorder may further be characterized by abnormal or altered signal transduction mediated by a PK. Abnormal or altered signaling further refers to changes in the activity or levels of molecules downstream to the PK resulting in aberrant signaling mediated by said PK (e.g. an increase or decrease in the activity of IRS1 leading to aberrant IGF1R signaling).

Thus, in one embodiment, the present invention is directed to preparations containing at least one compound represented by the structure of formula 1, 2, or 3, or at least one compound selected from compounds 4-16, which modulate PK activity signal transduction by affecting the activity of the protein kinases and interfering with the signal transduction pathways mediated by such proteins.

Examples of protein kinase related disorders are cell proliferative disorders, metabolic disorders or fibrotic disorders and inflammation.

Examples of cell proliferative disorders which are mediated by protein kinase activity, activation or signaling are cancer, psoriasis, diabetic nephropathy, blood vessel proliferative disorders, and mesangia cell proliferative disorders.

Cancer is a disorder in which a population of cells has become, in varying degrees, unresponsive to the control mechanisms that normally govern proliferation and differentiation. Cancer refers to various types of malignant neoplasms and tumors, including metastasis to different sites. Non-limiting examples of cancers which can be treated by any of the compounds represented by the structure of formula 1, 2, or 3, or any of the compounds 4-16 are ovarian cancer, prostate cancer, breast cancer, skin cancer, melanoma, colon cancer, lung cancer, pancreatic cancer, gastric cancer, bladder cancer, Ewing's sarcoma, lymphoma, leukemia, .multiple myeloma, head and neck cancer, kidney cancer, bone cancer, liver cancer and thyroid cancer which exhibit altered activity of PK and PK signaling. Specific examples of cancers which the compounds of the present invention are effective at treating¢ nr nreventing are: adenocarcinoma, adrenal gland tumor, ameloblastoma, anaplastic tumor, anaplastic carcinoma of the thyroid cell, angiofibroma, angioma, angiosarcoma, apudoma, argentaffinoma, arrhenoblastoma, ascites tumor cell, ascitic tumor, astroblastoma, astrocytoma, ataxia-telangiectasia , atrial myxoma, basal cell carcinoma, bone cancer, bone tumor, brainstem glioma, brain tumor, breast cancer, Burkitt's lymphoma, carcinoma, cerebellar astrocytoma, cervical cancer, cherry angioma, cholangiocarcinoma, a cholangioma, chondroblastoma, chondroma, chondro sarcoma, chorioblastoma, choriocarcinoma, colon cancer, common acute lymphoblastic leukaemia, craniopharyngioma, cystocarcinoma, cystofibroma, cystoma, cytoma, ductal carcinoma in situ, ductal papilloma, dysgerminoma, encephaloma, endometrial carcinoma, endothelioma, ependymoma, epithelioma, erythroleukaemia, Ewing's sarcoma, extra nodal lymphoma, feline sarcoma, fibroadenoma, fibrosarcoma, follicular cancer of the thyroid, ganglioglioma, gastrinoma, glioblastoma multiforme, glioma, gonadoblastoma, haemangioblastoma, haemangioendothelioblastoma, haemangioendothelioma, haemangiopericytoma, haematolymphangioma, haemocytoblastoma, haemocytoma, hairy cell leukaemia, hamartoma, hepatocarcinoma, hepatocellular carcinoma, hepatoma, histoma, Hodgkin's disease, hypernephroma, infiltrating cancer, infiltrating ductal cell carcinoma, insulinoma, juvenile angiofibroma, Kaposi sarcoma, kidney tumor, large cell lymphoma, leukemia, chronic leukemia, acute leukemia, lipoma, liver cancer, liver metastases, Lucke carcinoma, lymphadenoma, lymphangioma, lymphocytic leukaemia, lymphocytic lymphoma, lymphocytoma, lymphoedema, lymphoma, lung cancer, malignant mesothelioma, malignant teratoma, mastocytoma, medulloblastoma, melanoma, meningioma, mesothelioma, metastatic cancer, Morton's neuroma, multiple myeloma, myeloblastoma, myeloid leukemia, myelolipoma, myeloma, myoblastoma, myxoma, nasopharyngeal carcinoma, nephroblastoma, neuroblastoma, neurofibroma, neurofibromatosis, neuroglioma, neuroma, non-Hodgkin's lymphoma, oligodendroglioma, optic glioma, osteochondroma, osteogenic sarcoma, osteo sarcoma, ovarian cancer, Paget's disease of the nipple, pancoast tumor, pancreatic cancer, phaeochromocytoma, pheochromocytoma, plasmacytoma, primary brain tumor, progonoma, prolactinoma, renal cell carcinoma, retinoblastoma, rhabdomyosarcoma, rhabdosarcoma, solid tumor, sarcoma, secondary tumor, seminoma, skin cancer, small cell carcinoma, squamous cell carcinoma, strawberry haemangioma, T-cell lymphoma, teratoma, testicular cancer, thymoma, trophoblastic tumor, tumourigenic, vestibular schwannoma, Wilm's tumor, or a combination thereof.

Blood vessel proliferative disorders refer to antiogenic and vasculogenic disorders generally resulting in abnormal proliferation of blood vessels. The formation and spreading of blood vessels, or vasculogenesis and angiogenesis, respectively, play important roles in a variety of physiological processes such as embryonic development, corpus luteum formation, wound healing and organ regeneration, as well as a pivotal role in cancer development. Other examples of blood vessel proliferation disorders include arthritis and ocular diseases such as diabetic retinopathy, restenosis, retinopathies and atherosclerosis.

Mesangial cell proliferative disorders refer to disorders brought about by abnormal proliferation of mesangial cells. Mesangial proliferative disorders include various human renal diseases such as glomerulonephritis, diabetic nephropathy, malignant nephrosclerosis, thrombic microangiopathy syndromes, transplant rejection and glomerulopathies. In this regards, PDGFR has been implicated in the maintenance of mesangial cell proliferation.

Metabolic disorders that are implicated with abnormal PK activity and/or signaling include, but are not limited to, psoriasis, diabetes mellitus, wound healing, inflammation and neurodegenerative diseases. For example, EGFR signaling has been implicated in corneal and dermal wound healing. Defects in the Insulin-R and IGF-1 receptor signaling are involved in type-II diabetes mellitus.

Fibrotic disorders refer to the abnormal formation of extracellular matrices. Examples of fibrotic disorders include hepatic cirrhosis and mesangial cell proliferative disorders. Hepatic cirrhosis is characterized by the increase in extracellular matrix constituents resulting in the formation of a hepatic scar.

The present invention further provides a method of inhibiting, treating or preventing an insulin-like growth factor 1 receptor (IGF1R) and/or insulin receptor substrate 1 (IRS1) signaling related disorder. Data from experimental models and population studies have implicated that the IGF-1 system is involved in the pathogenesis of many different human cancers, including breast, prostate, lung, and colon cancer (reviewed in Ryan et al., *The Oncologist* (2008),13: 16-24). There are also several lines of evidence that dysregulation of the IGF-1 system and enhanced IGF-1R activation are involved in resistance to certain anticancer therapies, including cytotoxic chemotherapy, hormonal agents, biological therapies, and radiation.

Insulin receptor substrate 1 (IRS-1) is a constituent of the IGF-1R signaling pathway, and has been shown to be a key mediator in its role in malignant transformation (reviewed in Baserga, *Exp. Cell Res*. (2009), 315(5): 727-732).

Without wishing to be bound by any particular mechanism or theory, it is contemplated that the compounds disclosed herein are useful as inhibitors of IGF1-R signaling and/or IRS-1 signaling thus being highly potent in treating or preventing different types of cancer, both as a single agent therapeutic, and as an enhancement of existing therapies. Inhibition of IRS-1 signaling is beneficial for the treatment of various cancers where IGF1R has been shown to be involved, as well as for the treatment of other types of cancers, which are independent of IGF1R.

The term "treating" as used herein refers to abrogating, inhibiting, slowing or reversing the progression of a disease, ameliorating clinical symptoms of a disease or preventing the appearance of clinical symptoms of a disease. The term "preventing" is defined herein as barring a subject from acquiring a disorder or diseases.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like.

The term "administering" as used herein refers to bringing into contact with a compound of the present invention thus affecting the activity, activation or signaling of the kinase either directly; i.e. by interacting with the kinase itself, or indirectly; i.e. by interacting with another molecule on which the signaling activity of the enzyme is dependent. As used herein, administration can be accomplished in vitro, i.e. in a test tube, or in vivo, i.e. in cells or tissues of living organisms, for example humans. In one embodiment, the present invention encompasses administering the compounds of the present invention to a subject.

The term "inhibition of cell proliferation" as used herein refers to inhibition of abnoinial cells preferably cancerous cells expressed as a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

The term "therapeutically effective amount" refers to the amount of a compound being administered which provides a therapeutic effect for a given condition and administration regimen, specifically an amount which relieves to some extent one or more of the symptoms of the disorder being treated. Therapeutic effective doses for any compounds represented by the structure of formula 1, 2, or 3, or any of the compounds 4-16 described herein can be estimated initially from cell culture and/or an animal model. A dose can be formulated in an animal model, and this dose can be used to more precisely determine useful doses in humans.

The term "effective inhibitory amount" refers to the amount of a compound being administered that inhibits to some extent the protein kinase with which it is contacted.

Pharmaceutical Compositions:

The present invention further provides pharmaceutical compositions comprising at least one compound represented by the structure of formula 1, 2, or 3, or at least one compound selected from compounds 4-16, and a pharmaceutically acceptable carrier or excipient.

As used herein, "pharmaceutical composition" means therapeutically effective amounts of the compounds of the present invention, together with suitable diluents, preservatives, solubilizers, emulsifiers, adjuvant and/or carriers. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

Further comprehended by the invention are particulate compositions coated with polymers (e.g., poloxamers or poloxamines). Other embodiments of the compositions of the invention incorporate particulate forms, protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, intraventricularly, intracranially or intratumorally.

Moreover, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

Controlled or sustained release compositions include formulation in lipophilic depots (e.g. fatty acids, waxes, oils). Also comnrehended by the invention are particulate compositions coated with polymers (e.g. poloxamers or poloxamines) and the compound coupled to antibodies directed against tissue-specific receptors, ligands or antigens or coupled to ligands of tissue-specific receptors.

Other embodiments of the compositions of the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see for example Saudek et al., *N. Engl. J. Med.* (1989), 321:574-579). In another embodiment, polymeric materials can be used. In yet another embodiment, a controlled release system can be placed in proximity to the therapeutic target, i.e., the brain, thus requiring only a fraction of the systemic dose (see, e.g., Goodson, *Medical Applications of Controlled Release*, supra (1984), 2:115-138). Preferably, a controlled release device is introduced into a subject in proximity to the site of inappropriate immune activation or a tumor. Other controlled release systems are discussed in the review by Langer, *Science* (1990), 249: 1527-1533.

The pharmaceutical preparation may comprise one or more of the compounds represented by the structure of formula 1, 2, or 3, or any of the compounds 4-16, or may further include a pharmaceutically acceptable carrier, and can be in solid. or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the selective androgen receptor modulator can be administered to a subject by, for example, subcutaneous implantation of a pellet; in a further embodiment, the pellet provides for controlled release of selective androgen receptor modulator over a period of time. The preparation can also be administered by intravenous, intra-arterial, or intramuscular injection of a liquid preparation, oral administration of a liquid or solid preparation, or by topical application. Administration can also be accomplished by use of a rectal suppository or a urethral suppository.

The pharmaceutical preparations of the invention can be prepared by known dissolving, mixing, granulating, or tabletforming processes. For oral administration, the selective androgen receptor modulators or their physiologically tolerated derivatives such as salts, esters, N-oxides, and the like are mixed with additives customary for this purpose, such as vehicles, stabilizers, or inert diluents, and converted by customary methods into a suitable form of administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, or with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intra-arterial, or intramuscular injection), the compounds of the present invention or their physiologically tolerated derivatives such as salts, hydrates and the like are converted into a solution, suspension, or emulsion, if desired with the substances customary and suitable for this purpose, for example, solubilizers or other auxiliaries. Examples are sterile liquids such as water and oils, with or without the addition of a surfactant, and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycols are preferred liquid carriers, particularly for injectable solutions.

The preparation of pharmaceutical compositions which contain an active component is well understood in the art. Typically, such compositions are prepared as aerosols of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof.

In addition, if desired, the composition can contain minor amounts of auxiliary substances such as wetting or emulsifying agents, pH buffering agents, which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For topical administration to body surfaces using, for example, creams, gels, drops, and the like, the compounds of the present invention or their physiologically tolerated derivatives such as salts, hydrates, and the like are prepared and applied as solutions, suspensions, or emulsions in a physiologically acceptable diluent with or without a pharmaceutical carrier.

In another embodiment, the active compound can be delivered in a vesicle, in particular a liposome (see for example Langer, *Science* (1990), 249: 1527-1533; Treat et al., *Liposomes in the Therapy of Infectious Disease and Cancer* (1989), Lopez-Berestein and Fidler (eds.), Liss, N.Y., 353-365).

It should be noted that the term "and" or the term "or" are generally employed in its sense including "and/or" unless the content clearly dictates otherwise.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLE 1

Synthesis—General Procedures

The general procedures for the synthesis of compounds 4-16 are disclosed hereinbelow:

General Procedure I for the Synthesis of Cinnamic Acids by Knoevenagel Condensation A catalytic amount of piperidine (0.2 equiv.) was added to a solution of a benzaldehyde (1 equiv.) and malonic acid (1.5 equiv.) in pyridine (4 ml/mmol aldehyde). The reaction mixture was heated to 120° C. for 6 hours. The solution was cooled to 0° C. and concentrated HCl was added drop-wise to pH <3. The precipitate was collected by filtration, washed with water and dried under reduced pressure to give the corresponding cinnamic acid.

General Procedure II for the Synthesis of Amides via Acid Chlorides

To a cooled solution of the cinnamic acid (1 equiv.) in $CH_2Cl_2$, oxalyl chloride (4 equiv.) was added and the solution was stirred for 1-2 hours at room temperature. The excess of oxalyl chloride was distilled off and the mixture was evaporated to dryness. The residue was dissolved in $CH_2Cl_2$ and added drop-wise to a cooled solution of the benzylamine (0.9 equiv.) and $Et_3N$ (4 equiv.) in $CH_2Cl_2$. The reaction mixture was stirred at room temperature over night (until TLC indicated the disappearance of the amine) and then treated with water. The $CH_2Cl_2$ was evaporated under reduced pressure and the residual was filtered and washed with ethyl acetate. The filtrate was extracted twice with ethyl acetate and the combined organic phases were dried over $Na_2SO_4$, filtered and the solvent was evaporated to give brown solid. The crude solid was purified by flash chromatography (ethyl acetate/hexanes) to give the amide.

General Procedure III for the Synthesis of Amides via DCC-Coupling

To a cooled (ice-bath) solution of the cinnamic acid (1 equiv.) in DMF (5 ml/mmol), HOBt (1.1 equiv.) was added followed by DCC (1.0 equiv.). The solution was stirred for 15 minutes and a solution of the benzylamine (1 equiv.) in DMF (3 ml/mmol) was added in one portion. After 5 minutes, the reaction mixture was allowed to reach room temperatures and the mixture was stirred overnight. The resulting suspension was filtered and the filtrate was poured into a separating funnel containing water (100 ml). The mixture was extracted trice with diethyl ether. The combined ether fractions were washed with water, 3% $K_2CO_3$, 1M HCl, water and brine. The ether fraction was dried over $Na_2SO_4$. Filtration and evaporation of the solvent gave the crude product that was further purified via column chromatography over silica gel.

General Procedure IV for the Synthesis of Thioamides

The amide (1 equiv.) and Lawesson's reagent (0.55 equiv.) were refluxed in toluene for 3 hours (until TLC indicated the disappearance of the amide). The reaction mixture was cooled to room temperature. The crude mixture was adsorbed onto silica gel and purified by column chromatography (ethyl acetate/hexane) to yield the thioamides.

General Procedure V for De-Methylation

Boron tribromide (2.5 equiv. excess for each hydroxyl group) was added to an ice-cold solution of the protected product in $CH_2Cl_2$ (ca. 20 ml/mmol). The reaction mixture was allowed to warm to room temperatures and stirred for 5 hours. The solution was cooled to 0° C. and then treated with cooled water. The DCM was evaporated and the solution was extracted three times with ethyl acetate. The combined organic layers were dried over $Na_2SO_4$ and the solvent was evaporated under reduced pressure. The crude yellow product was crystallized from water/ethanol or purified by preparative HPLC.

Synthesis of a

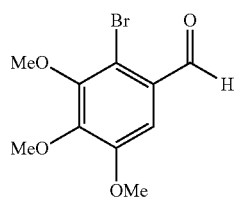 [SMILES: COc1cc(C=O)c(Br)c(OC)c1OC]

To a solution of 3,4,5-trimethoxybenzaldehyde (1 equiv.) in methanol bromine (1.1 equiv.) was added and the solution was stirred at room temperature for 3 hours. The solvent was evaporated and the excess of bromine was neutralized with saturated solution of $Na_2S_2O_3$. The aqueous layer was extracted twice with $CH_2Cl_2$ and the combined organic layers were dried over $Na_2SO_4$, filtered and the solvent was evaporated to give off-white solid in 95% yield. The product was used without further purification.

Synthesis of b

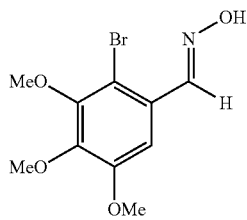

Aldehyde a (1 equiv.) was dissolved in minimum amount of warm ethanol, and a solution of hydroxylamine hydrochloride (1.2 equiv.) in water (30 ml) was added. Then aqueous solution of 10% sodium hydroxide (1.33 equiv.) was added and the mixture' was stirred at room temperature for 2 hours (until TLC indicated the disappearance of the aldehyde). The white precipitation was collected by filtration, washed with water and dried under reduced pressure to yield a pure white solid in 80% yield.

Synthesis of c

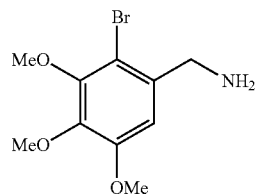 [SMILES: COc1cc(CN)c(Br)c(OC)c1OC]

To a solution of b (1 equiv.) in acetic acid (3 ml/mmol b), zinc (3 equiv.) was added. The solution was refluxed until TLC showed the disappearance of the oxime. The zinc salts were filtered and washed with ethyl acetate. The filtrate was evaporated and aqueous sodium hydroxide was added. The aqueous layer was extracted three times with ethyl acetate. The organic layer was washed with brine, dried over $Na_2SO_4$ and evaporated under reduced pressure to yield yellowish oil in 36% yield.

c: $^1$H NMR (400 MHz, $CDCl_3$): δ 6.81 (s, 1H), 4.46 (d, J=6 Hz, 2H), 3.91 (s, 3H), 3.87 (s, 3H), 3.86 (s, 3H).

Synthesis of d

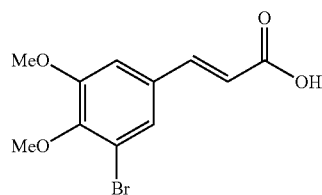 [SMILES: COc1cc(/C=C/C(=O)O)cc(Br)c1OC]

Compound d was prepared from 5-bromovertaldehyde according to general procedure I in 65% yield. White solid.

d: $^1$H NMR (300 MHz, $CDCl_3$): δ 7.65 (d, J=15.9 Hz), 7.35 (d, J=2.1 Hz, 1H), 7.01 (d, J=2.1 Hz, 1H), 6.35 (d, J=15.9 Hz, 1H), 3.90 (s, 3H), 3.88 (s, 3H).

Synthesis of e

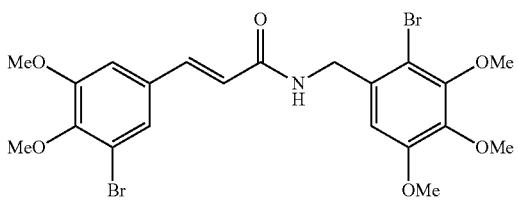 [SMILES: COc1cc(/C=C/C(=O)NCc2cc(OC)c(OC)c(OC)c2Br)cc(Br)c1OC]

Compound e was prepared from d according to general procedure II. Purified by flash chromatography (ethyl acetate/hexanes) to give e in 45% yield. White solid.

e: $^1$H NMR (400 MHz, $CDCl_3$): δ 7.51 (d, J=15.5 Hz, 1H), 7.31 (d, J=2 Hz, 1H), 6.95 (d, J=2 Hz, 1H), 6.86 (s, 1H), 6.32 (d, J=15.5 Hz, 1H), 6.15 (t, J=4.8 Hz, 1H), 4.60 (d, J=4.8 Hz, 2H), 3.90-3.86 (s, 15H).

Synthesis of f

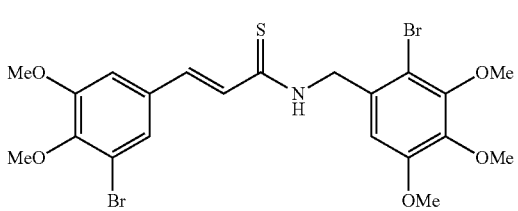 [SMILES: COc1cc(/C=C/C(=S)NCc2cc(OC)c(OC)c(OC)c2Br)cc(Br)c1OC]

Compound f was prepared from e according to general procedure IV. Purified by flash chromatography (ethyl acetate/hexanes) to yield f in 50% yield. Pale yellow solid.

f: ¹H NMR (400 MHz, CDCl₃): δ 7.67 (d, J=15.2 Hz, 1H), 7.61 (bt, 1H), 7.34 (d, J=2 Hz, 1H), 6.97 (d, J=2 Hz, 1H), 6.95 (s, 1H), 6.72 (d, J=15.2 Hz, 1H), 5.05 (d, J=5.6 Hz, 2H), 3.90-3.86 (s, 15H).

Synthesis of 4

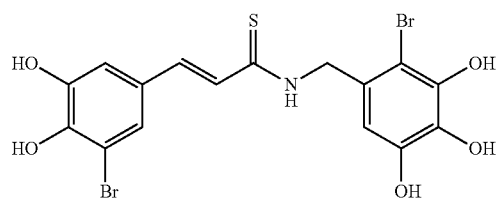 [SMILES: Oc1cc(/C=C/C(=S)NCc2cc(O)c(O)c(O)c2Br)cc(Br)c1O]

The general procedure for the synthesis of compound 4 is drawn schematically in FIG. 1. Compound 4 was prepared according to general procedure V. Crystallization was performed from water/ethanol to give 4 in 50-60% yield. Yellow crystals.

4: ¹H NMR (400 MHz, Acetone-d₆): δ 9.10 (bt, 1H), 7.70 (d, J=15.2 Hz, 1H), 7.32 (d, J=2 Hz, 1H), 7.12 (d, J=2 Hz, 1H), 7.08 (d, J=15.2 Hz, 1H), 6.60 (s, 1H), 4.91 (d, J=4.8 Hz, 2H).

Synthesis of g

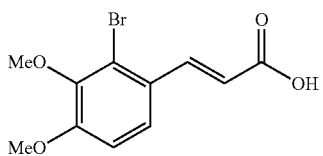

Compound g was prepared from 2-bromo-3,4-dimethoxybenzaldehyde according to general procedure I in 62% yield. White solid.

g: ¹H NMR (400 MHz, CDCl₃+ Acetone-d₆): δ 8.07 (d, J=15.6 Hz), 7.45 (d, J=8.8 Hz, 1H), 6.95 (d, J=8.8 Hz, 1H), 6.31 (d, J=15.6 Hz, 1H), 3.93 (s, 3H), 3.85 (s, 3H).

Synthesis of h

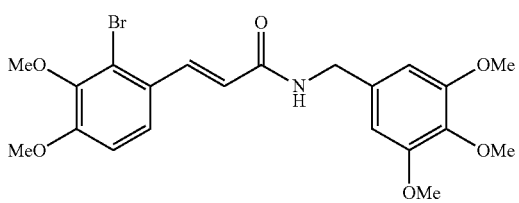

Compound h was prepared from g and 3,4,5-trimethoxybenzylamine according to general procedure II. Purified by flash chromatography (ethyl acetate/hexanes) to give h in 55% yield. White solid.

h: ¹H NMR (400 MHz, CDCl₃): δ 7.96 (d, J=15.6 Hz, 1H), 7.31 (d, J=8.8 Hz, 1H), 6.86 (d, J=8.8 Hz, 1H), 6.55 (s, 2H), 6.28 (d, J=15.6 Hz, 1H), 5.91 (bt, 1H), 4.50 (d, J=5.6 Hz, 2H), 3.90 (s, 3H), 3.85 (s, 9H), 3.84 (s, 3H).

Synthesis of i

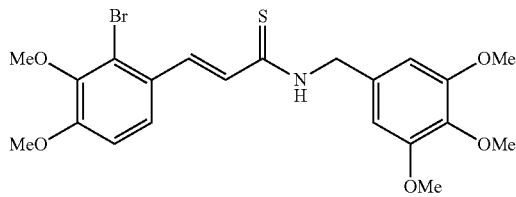

Compound i was prepared from h according to general procedure IV. Purified by flash chromatography (ethyl acetate/hexanes) to yield i in 50% yield. Pale yellow solid.

i: ¹H NMR (400 MHz, CDCl₃): δ 8.05 (d, J=15.6 Hz, 1H), 7.45 (bt, 1H), 7.33 (d, J=8.8 Hz, 1H), 6.86 (d, J=8.8 Hz, 1H), 6.73 (d, J=15.6 Hz, 1H), 6.60 (s, 2H), 4.89 (d, J=5.2 Hz, 2H), 3.91 (s, 3H), 3.86 (s, 6H), 3.85 (s, 3H), 3.83 (s, 3H).

Synthesis of 5

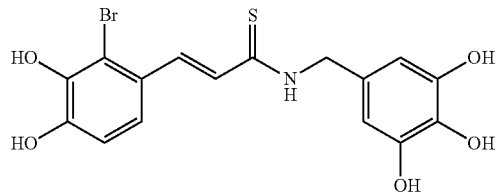

Figure 2:
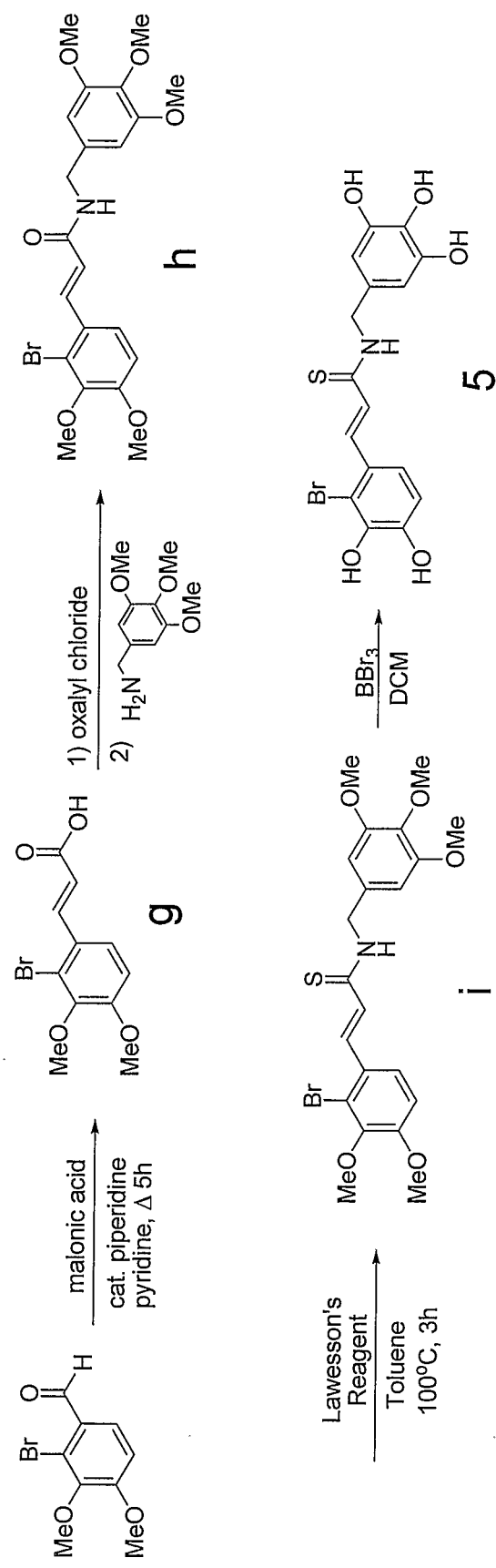
FIG. 2 Shows in schematic form an exemplary process for the synthesis of an exemplary novel Tyrphostin of the invention (compound 5).

The general procedure for the synthesis of compound 5 is drawn schematically in FIG. 2. Compound 5 was prepared from i according to general procedure V. Crystallization was performed from water/ethanol to give product 5 in 50-60% yield. Yellow crystals.

5: ¹H NMR (300 MHz, CDCl₃): δ 4.77 (d, 2H, J=5.2 Hz, CH₂N), 6.43 (s, 2H, aromatic), 6.86 (d, 1H, J=8.4 Hz, aromatic), 7.01 (d, 1H, d=15.2 Hz, alkene), 7.16 (d, 1H, J=8.4 Hz, aromatic), 8.27 (d, 1H, J=15.2 Hz, alkene), 8.99 (br.s., 1H, NH).

Synthesis of j

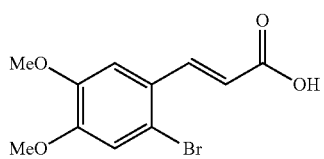 [SMILES: COc1cc(Br)c(/C=C/C(=O)O)cc1OC]

Compound j was prepared from 2-bromo-4,5-dimethoxybenzaldehyde in 75% yield according to general procedure I. White solid.

j: ¹H NMR (300 MHz, CDCl₃): δ 7.96 (d, J=15.6 Hz, 1H, Ar—CH=CH), 7.43 (s, 1H, aromatic CH), 7.20 (s, 1H, aromatic CH), 6.48 (d, J=15.6 Hz, 1H, 1H, Ar—CH=CH), 3.91 (s, 3H, OCH₃), 3.90 (s, 3H, OCH₃).

Synthesis of k

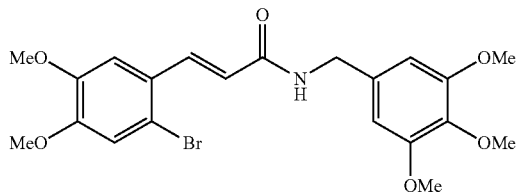 [SMILES: COc1cc(Br)c(/C=C/C(=S)NCc2cc(OC)c(OC)c(OC)c2)cc1OC]

Compound k was prepared from j and 3,4,5-trimethoxybenzylamine according to general procedure II in 42% yield after flash chromatography (ethyl acetate/hexanes). White solid.

k: $^1$H NMR (400 MHz, CDCl$_3$): δ 7.90 (d, J=15.6 Hz, 1H, Ar—CH=CH), 7.022 (s, 1H, aromatic CH), 6.99 (s, 1H, aromatic CH), 6.54 (s, 2H, aromatic CH), 6.29 (d, J=15.6 Hz, 1H, 1H, Ar—CH=CH), 5.99 (bt, 1H, NH), 4.49 (d, J=6 Hz, 2H, CH$_2$N), 3.88 (s, 3H, OCH$_3$), 3.86 (s, 3H, OCH$_3$), 3.84 (s, 6H, OCH$_3$), 3.82 (s, 3H, OCH$_3$). MS (ESI): found (m/z) 467.93; calculated for C$_{21}$H$_{24}$BrNO$_6$ (MH$^+$) 467.32.

Synthesis of l

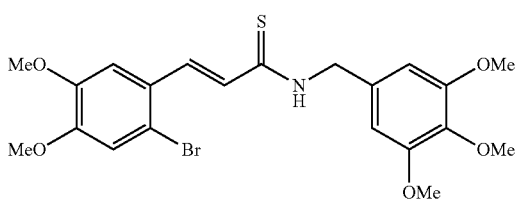

Compound l was prepared from k according to general procedure IV in 56% yield after chromatography. Yellow solid.

l: $^1$H NMR (400 MHz, CDCl$_3$): δ 8.20 (d, J=15.2 Hz, 1H, Ar—CH=CH), 7.28 (s, 1H, aromatic CH), 7.22 (s, 1H, aromatic CH), 7.12 (d, J=15.2 Hz, 1H, 1H, Ar—CH=CH), 6.79 (s, 2H, aromatic CH), 4.92 (d, J=5.2 Hz, 2H, CH$_2$N), 3.90 (s, 3H, OCH$_3$), 3.86 (s, 3H, OCH$_3$), 3.83 (s, 6H, OCH$_3$), 3.73 (s, 3H, OCH$_3$). MS (ESI): found (m/z) 483.87; calculated for C$_{21}$H$_{24}$BrNO$_5$S (MH$^+$) 483.39.

Synthesis of 6

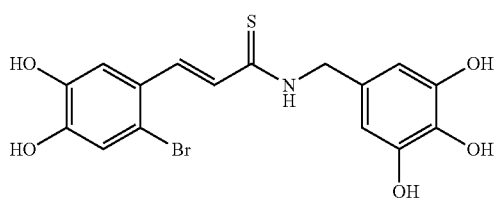 [SMILES: Oc1cc(Br)c(/C=C/C(=S)NCc2cc(O)c(O)c(O)c2)cc1O]

Figure 3:
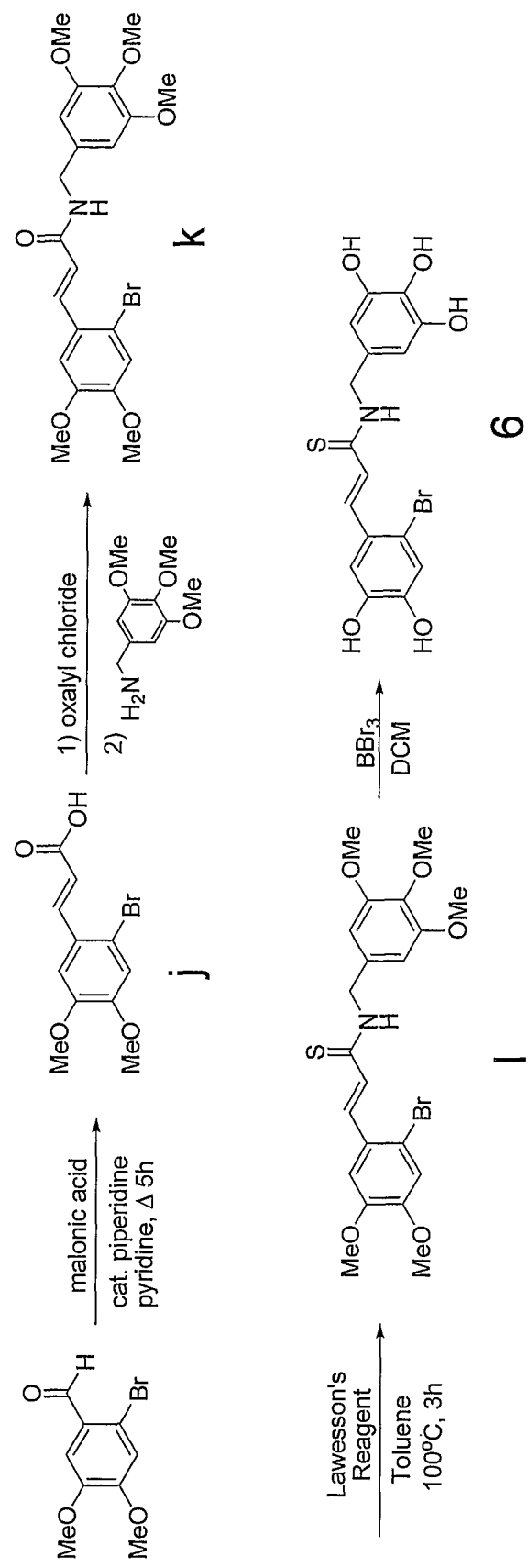
FIG. 3 Shows in schematic form an exemplary process for the synthesis of an exemplary novel Tyrphostin of the invention (compound 6).

The general procedure for the synthesis of compound 6 is drawn schematically in FIG. 3. Compound 6 was prepared from l in 50-60% yields according to general procedure V. Purification by crystallization was performed from water/ethanol.

6: $^1$H NMR (400 MHz, CDCl$_3$): δ 8.20 (d, J=15.2 Hz, 1H, Ar—CH=CH), 7.23 (s, 1H, aromatic CH), 7.12 (s, 1H, aromatic CH), 6.99 (d, J=15.2 Hz, 1H, 1H, Ar—CH=CH), 6.46 (s, 2H, aromatic CH), 4.79 (d, J=5.6 Hz, 2H, CH$_2$N).

Synthesis of m

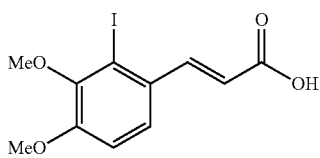 [SMILES: COc1ccc(/C=C/C(=O)O)c(I)c1OC]

Compound m was prepared according to general procedure I in 65% yield from 2-iodo-3,4-dimethoxybenzaldehyde. White solid.

m: $^1$H NMR (300 MHz, CDCl$_3$): δ 7.98 (d, J=16 Hz, 1H, Ar—CH=CH), 7.86 (d, J=8.6 Hz, 1H, aromatic CH), 7.17 (d, J=8.6 Hz, 1H, aromatic CH), 6.37 (d, J=16.0 Hz, 1H, Ar—CH=CH), 3.96 (s, 3H, OCH$_3$), 3.82 (s, 3H, OCH$_3$).

Synthesis of n

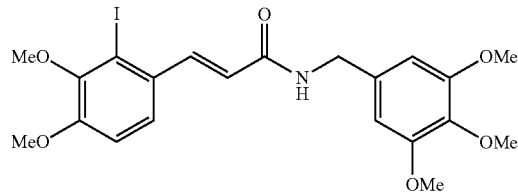

Compound n was prepared from m and 3,4,5-trimethoxybenzylamine according to general procedure II in 45% yield after column chromatography (ethyl acetate/hexanes). White solid.

n: $^1$H NMR (400 MHz, CDCl$_3$): δ 0.88 (d, J=15.2 Hz, 1H, Ar—CH=CH), 7.29 (d, J=15.6 MHz, 1H, Ar—CH=CH), 6.88 (d, 1H, J=15.2 MHz, 1H, Ar—CH=CH), 6.55 (s, 2H, aromatic CH), 6.19 (d, J=Hz, 1H, aromatic CH), 5.90 (bt, 1H, NH), 4.51 (d, J=6 Hz, 2H, CH$_2$N), 3.89 (s, 3H, OCH$_3$), 3.86 (s, 6H, OCH$_3$), 3.83 (s, 6H, OCH$_3$). MS (ESI): found (m/z) 513.93; calculated for C$_{21}$H$_{24}$INO$_6$ (MH$^+$) 513.32.

Synthesis of o

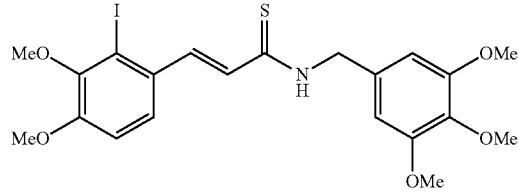 [SMILES: COc1cc(CNC(=S)/C=C/c2ccc(OC)c(OC)c2I)cc(OC)c1OC]

Compound o was prepared from n according to general procedure IV in 50% yield after column chromatography (ethyl acetate/hexanes). Pale yellow solid.

o: $^1$H NMR (400 MHz, CDCl$_3$): δ 7.97 (d, J=15.2 Hz, 1H, Ar—CH=CH), 7.29 (d, J=8.4 MHz, 1H, aromatic CH), 6.87 (d, J=8.4 MHz, 1H, aromatic CH), 6.63 (d, J=15.2 Hz, 1H, 1H, Ar—CH=CH), 6.60 (s, 2H, aromatic CH), 4.90 (d, J=5.2 Hz, 2H, CH$_2$N), 3.89 (s, 3H, OCH$_3$), 3.86 (s, 6H, OCH$_3$), 3.84 (d J=2.8 MHz, 6H, OCH$_3$). MS (ESI): found (m/z) 529.87; calculated for C$_{21}$H$_{24}$INO$_5$S (MH$^+$) 529.39.

Synthesis of 7

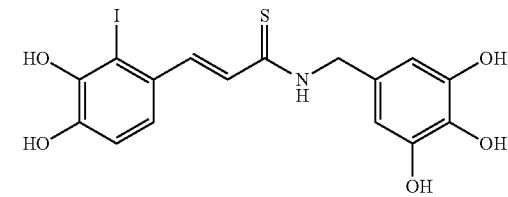 [SMILES: Oc1cc(CNC(=S)/C=C/c2ccc(O)c(O)c2I)cc(O)c1O]

Figure 4:
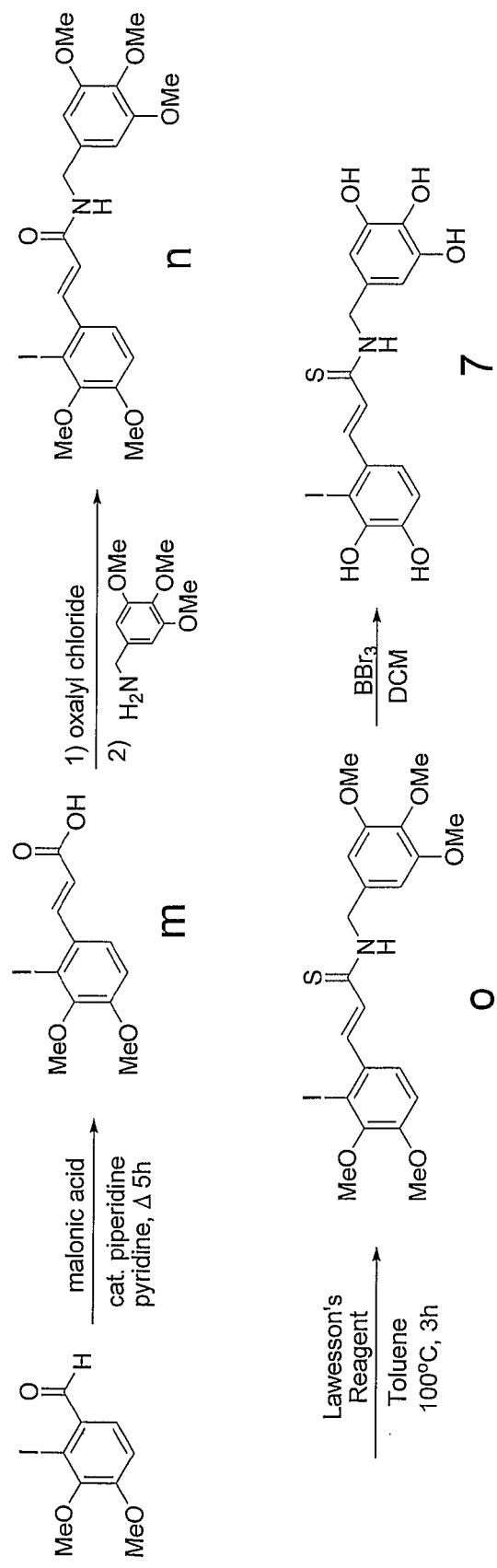
FIG. 4 Shows in schematic form an exemplary process for the synthesis of an exemplary novel Tyrphostin of the invention (compound 7).

The general procedure for the synthesis of compound 7 is drawn schematically in FIG. 4. Compound 7 was prepared from o according to general procedure V in 50-60% yield after crystallization from water/ethanol. Yellow crystals.

7: $^1$H NMR (400 MHz, CDCl$_3$): δ 9.19 (bs, 1H, NH), 8.26 (d, J=14.8 Hz, 1H, Ar—CH=CH), 7.14 (d, J=8.4 MHz, 1H, aromatic CH), 6.94 (d, J=14.8 Hz, 1H, Ar—CH=CH), 6.74

(d, J=8.4 Hz, 1H, aromatic CH), 6.48 (s, 2H, aromatic CH), 4.79 (d, J=5.6 Hz, 2H, CH₂N). MS (ESI): found (m/z) 459.87; calculated for $C_{16}H_{14}INO_5S$ (MH⁺) 459.26.

Synthesis of p (2,3-Bromo-4,5-dimethoxycinnamic acid)

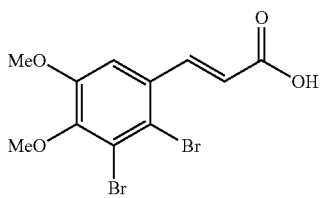 [SMILES: COc1cc(/C=C/C(=O)O)c(Br)c(Br)c1OC]

Compound p was prepared from 2,3-dibromo-4,5-dimethoxybenzaldehyde according general procedure I in 92% yield. Off-white solid.

p: ¹H-NMR (400 MHz, CD₃OD): δ 3.80 (s, 3H, OCH₃), 3.89 (s, 3H, OCH₃), 6.43 (d, 1H, J=12 Hz, CH=CH), 7.35 (s, 1H, aromatic), 8.02 (d, 1H, J=12 Hz, CH=CH).

Synthesis of q

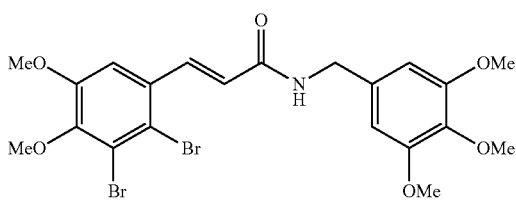

Compound q was prepared from p and 3,4,5-trimethoxybenzylamine in 86% yield according to general procedure III. Off-white solid.

q: ¹H-NMR (CDCl₃): 3.83 (s, 3H, OCH₃), 3.85 (s, 6H, 2× OCH₃), 3.87 (s, 3H, OCH₃), 3.88 (s, 3H, OCH₃), 4.50 (d, 2H, CH₂N, J=5.6 Hz), 5.96 (t, 1H, NH, J=5.6 Hz), 6.27 (d, 1H, J=15.2 Hz, CH=CH), 6.55 (s, 2H, aromatic), 7.04 (s, 1H, aromatic), 7.95 (d, 1H, J=15.2 Hz, CH=CH).

Synthesis of r

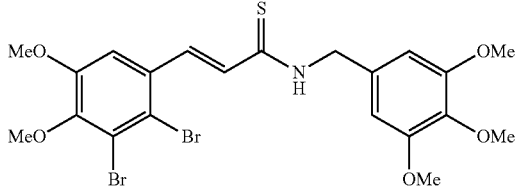

Compound r was prepared from q according to general procedure IV. Purification by column chromatography (ethyl acetate:hexane=1:1). Small yellow crystals, 67% yield.

r: ¹H-NMR (CDCl₃): 3.84 (s, 3H, OCH₃), 3.86 (s, 6H, 2× OCH₃), 3.87(s, 3H, OCH₃), 3.88 (s, 3H, OCH₃), 4.88 (d, 2H, CH₂N, J=5.2 Hz), 6.59 (s, 2H, aromatic benzylamine ring), 6.71 (d, 1H, J=15.2 Hz, CH=CH) 7.05 (s, 1H, aromatic, brominated ring), 7.54 (t, 1H, NH, J=5.2 Hz), 7.95 (d, 1H, J=15.2 Hz, CH=CH).

Synthesis of 8a and 8b

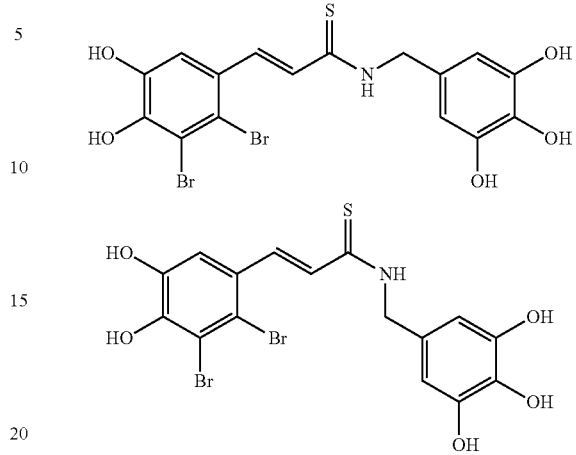

Figure 5:
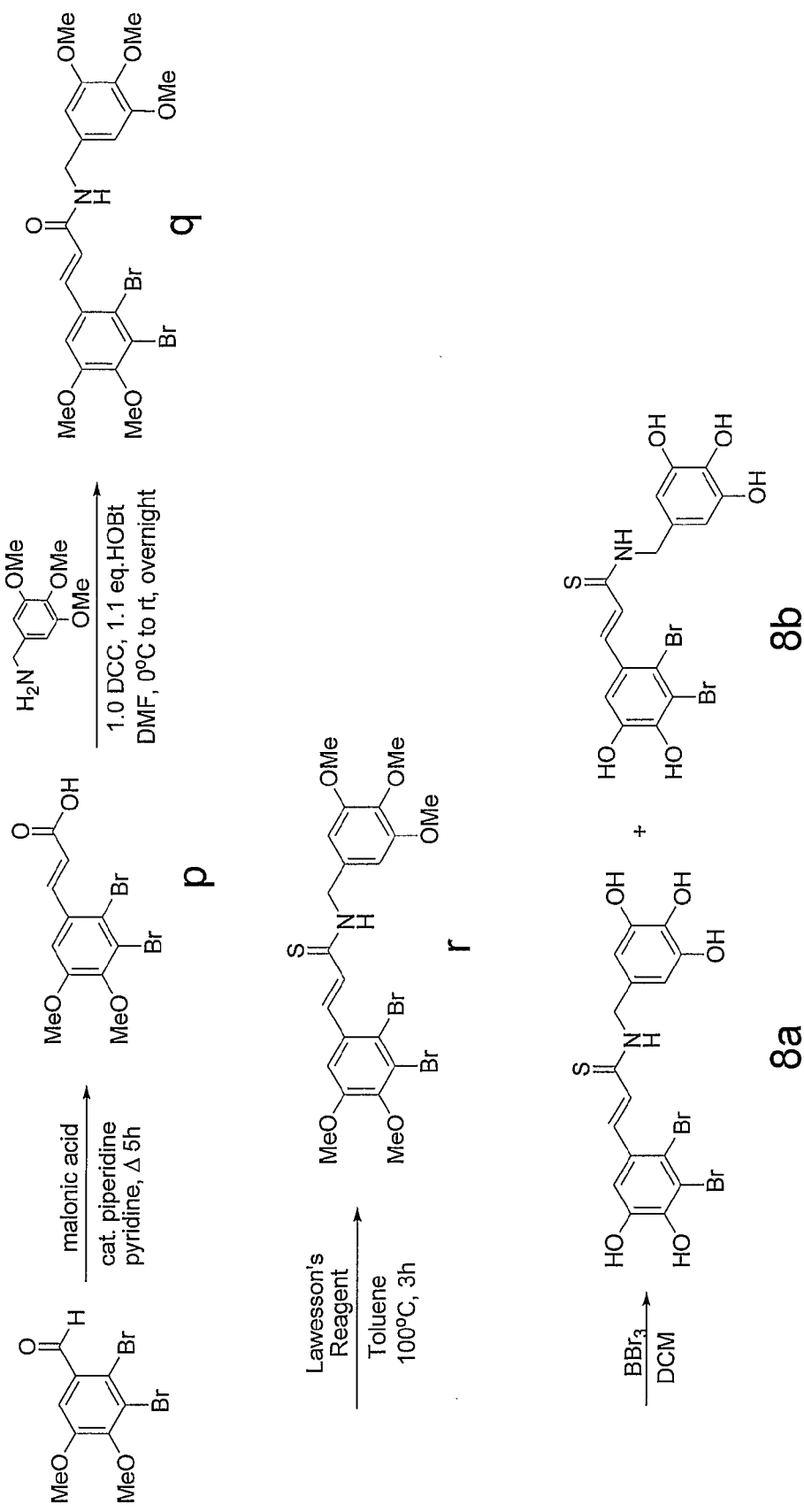
FIG. 5 Shows in schematic form an exemplary process for the synthesis of exemplary novel Tyrphostins of the invention (compounds 8a and 8b).

The general procedure for the synthesis of compounds 8a and 8b is drawn schematically in FIG. 5. Compounds 8a and 8b were prepared from r according to general procedure V. Purification by preparative HPLC (5-95% ACN in 20 min 35 deg). Analytical HPLC of the product showed two peaks in ratio approx. 10:1, partly overlapping.

¹H-NMR (acetone-d₆): 10:1 mixture of isomers (resulting from thioamide group).

Major isomer: 4.79 (br.d., 2H, CH₂NH); 6.45 (s, 2H, aromatic trimethoxy-ring), 6.95 (d, 1H, J=15.2 Hz, CH=CH), 7.30 (s, 1H, aromatic brominated ring), 8.27 (d, 1H, J=15.2 Hz, CH=CH), 9.24 (br.t., 1H, NH).

Minor isomer: 4.83 (br.d., 2H, CH₂NH); 6.33 (s, 2H, aromatic trimethoxy-ring), 6.99 (d, 1H, J=15.2 Hz, CH=CH), 7.17 (s, 1H, aromatic brominated ring), 8.44 (d, 1H, J=15.2 Hz, CH=CH).

Synthesis of s

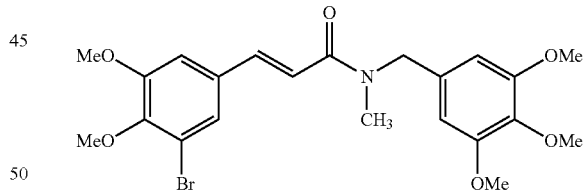

Compound s was prepared from d and N-methyl-(3,4,5-trimethoxybenzyl)-amine according to general procedure III. Purification via column chromatography (ethyl acetate: hexane=2:1). White solid (76%).

s: ¹H-NMR (CDCl₃): two isomers: 3.08 (unsymmetrical doublet from two overlapping doublets, 3H, J=6.8 Hz, N—CH₃), 3.81-3.88 (m, 15H, 5× OCH₃), 4.62 (unsymmetrical doublet from two overlapping doublets, 2H, J=Hz, CH₂—N), 6.40 and 6.49 (two singlets, together 2H, aromatic trimethoxy-ring), 6.74, 6.82 (two doublets, together 1H, J=15.2 Hz, CH=CH)), 6.88 and 6.96 (two singlets, together 1H, aromatic brominated ring), 7.27 and 7.36 (two singlets, together 1H, aromatic brominated ring), 7.61 (d; 1H, J=15.2 Hz, CH=CH).

Synthesis of t and t'

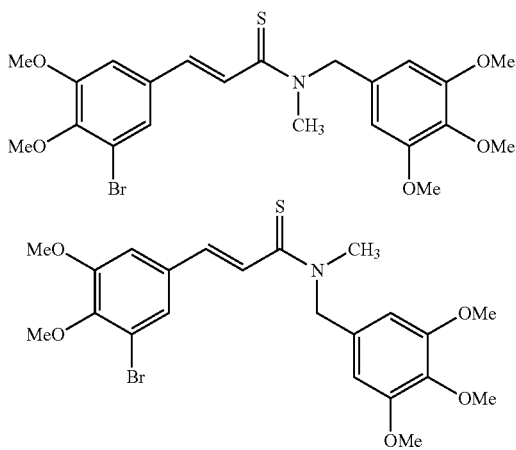

Compounds t and t' were prepared from s, (580 mg; 1.2 mmol), according to general procedure IV. Purification via column chromatography (hexane:ethyl acetate=2:1), 380 mg (77%). Yellow crystalline solid.

t and t': $^1$H-NMR (CDCl$_3$): Two atropisomers with ratio 10:9. 3.31 and 3.57 (N—CH$_3$), 3.83-3.90 (m, 15H, 5× OCH$_3$), 4.88 and 5.35 (s, 2H, CH$_2$N), 6.37 and 6.62 (2H, aromatic trimethoxy ring), 6.74, 6.82 (two doublets, together 1H, J=15.2 Hz, CH═CH)), 6.87 and 6.98 (two doublets, together 1H, J=1 Hz, aromatic brominated ring), 7.02 and 7.05 (two doublets, 1H, J=13.6 Hz, CH═CH), aromatic brominated ring), 7.25 and 7.38 (two doublets, together 1H, J=1 Hz, aromatic brominated ring), 7.61 (two doublets; 1H, J=13.6 Hz, CH═CH).

Synthesis of 9a and 9b

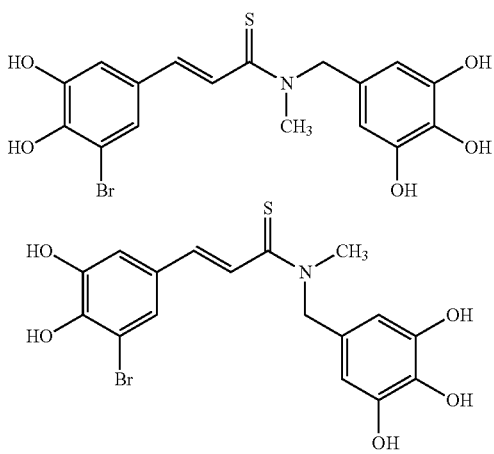

Figure 6:
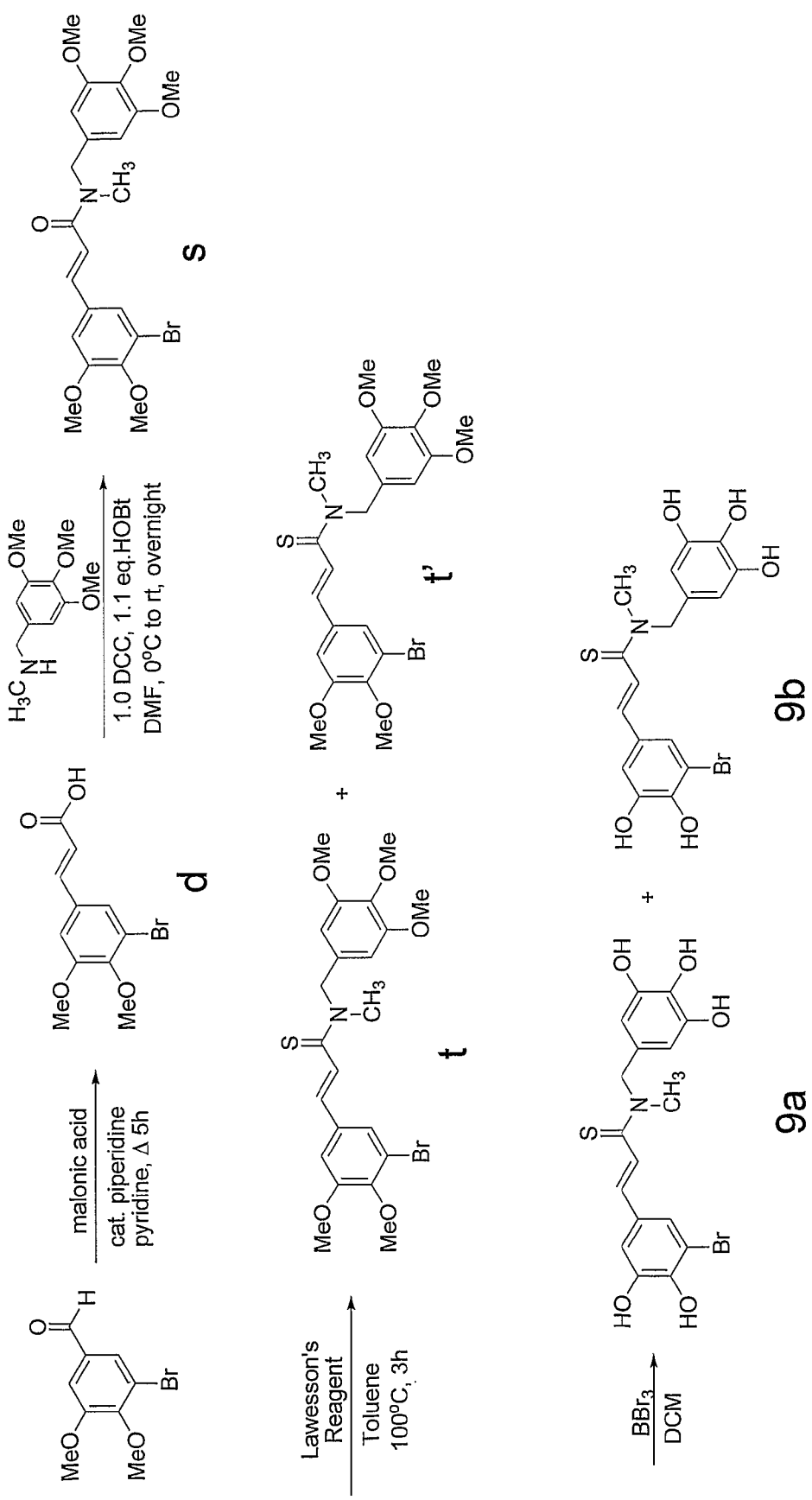
FIG. 6 Shows in schematic form an exemplary process for the synthesis of exemplary novel Tyrphostins of the invention (compounds 9a and 9b).

The general procedure for the synthesis of compounds 9a and 9b is drawn schematically in FIG. 6. Compounds 9a and 9b were prepared from t and t', respectively (300 mg; 0.6 mmol) BBr$_3$ (0.9 ml; 9 mmol; 15 equiv.) according to general procedure V. The crude product was purified by preparative HPLC (5-95% ACN in 20 min 35 deg). 76 mg (30%) yield.

9a and 9b: $^1$H-NMR (400 MHz, acetone-d$_6$): mixture of isomers δ 3.05, 3.34 and 3.49 (singlets, NCH$_3$ of the different isomers), 4.61, 4.91, 5.12 and 5.26 (s, 2H, CH$_2$ of the different isomers), 6.1-6.3 (overlapping peaks, 3H aromatic and alk- ene), 6.47 and 6.53 (s, 1H), 6.98-7.4 (m, aromatic 2H and NH, 1H), 7.66 and 7.69 (d, 1H, J=4.8 Hz, alkene).

Synthesis of u

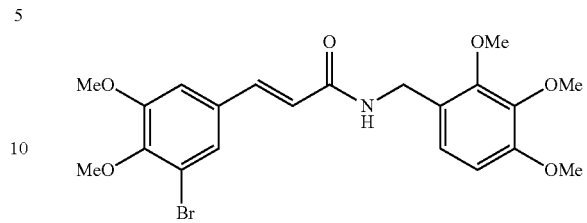

Compound u was prepared from d and 2,3,4-trimethoxybenzylamine according to general procedure II. Purification by flash chromatography (ethyl acetate/hexanes) gave u 45% yield. White solid.

u: $^1$H NMR (400 MHz, CDCl$_3$): δ 3.79 (s, 3H, OCH$_3$), 3.81 (s, 6H, 2× OCH$_3$), 3.83 (s, 3H, OCH$_3$), 3.90 (s, 3H, OCH$_3$), 4.45 (d, 2H, J=5.6 Hz, CH$_2$N), 6.33 (d, 1H, J=15.6 Hz, Ar—CH═CH—), 6.42 (t, 1H, J=5.2 Hz, NH), 6.57 (d, 1H, J=8.4 Hz, aromatic), 6.88 (s, 1H, aromatic), 6.96 (d, 2H, J=8.4 Hz, aromatic), 7.23 (s, 1H, aromatic), 7.44 (d, 1H, J=15.6 Hz, Ar—CH═CH—).

Synthesis of v

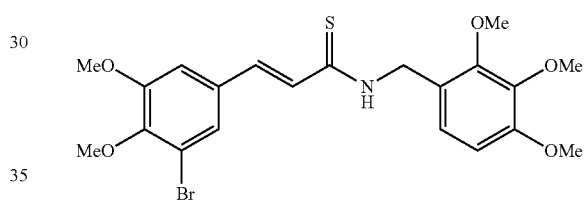

Compound v was prepared from u according to general procedure IV in 50% yield. Pale yellow solid.

v: $^1$H NMR (400 MHz, CDCl$_3$): two isomers in 2:1 ratio.

Major isomer: δ 7.67 (d, J=15.2 Hz, 1H, Ar—CH═CH), 7.07 (d, J=2 Hz, 1H, aromatic CH), 6.95 (d, J=2 Hz, 1H, aromatic CH), 6.88 (d, J=8.8 Hz, 1H, 1H, aromatic CH), 6.65 (d, 1H, J=8.8 Hz, 1H, aromatic CH), 4.72 (d, J=5.2 Hz, 2H, CH$_2$N), 3.85-3.71(m, 15H, OCH$_3$).

Synthesis of 10

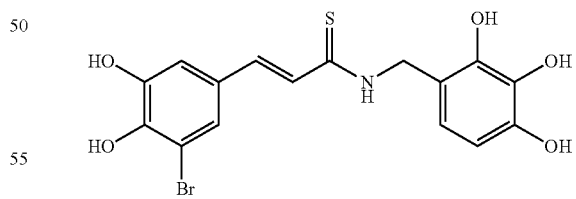

Figure 7:
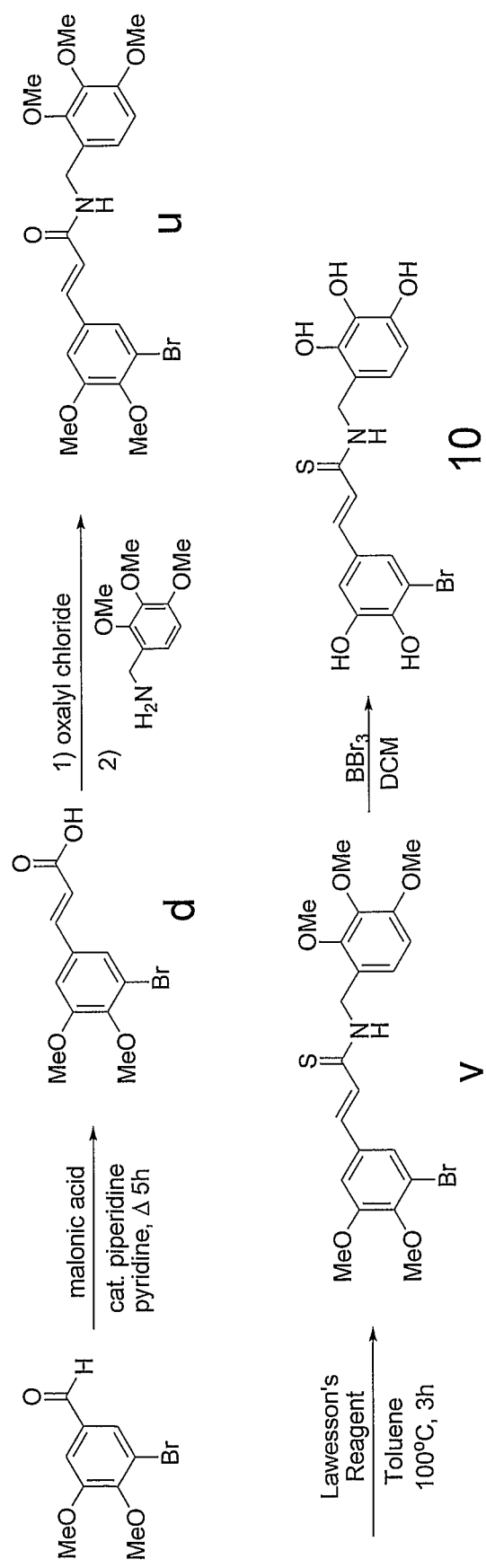
FIG. 7 Shows in schematic form an exemplary process for the synthesis of an exemplary novel Tyrphostin of the invention (compound 10).

The general procedure for the synthesis of compound 10 is drawn schematically in FIG. 7. Compound 10 was prepared from v according to general procedure V. Re-crystallized from water/ethanol in 50-60% yield. Yellow crystals.

10: $^1$H NMR (400 MHz, CDCl$_3$): δ 9.24 (bs, 1H, NH), 7.70 (d, J=15.2 Hz, 1H, Ar—CH═CH), 7.31 (d, J=2 Hz, 1H, aromatic CH), 7.10 (d, J=2 Hz, 1H, aromatic CH), 7.04 (d, 1H, J=15.2 Hz, Ar—CH═CH), 6.68 (d, J=8.4 Hz, 1H, aromatic CH), 4.88 (s, 2H, CH$_2$N).

Synthesis of w

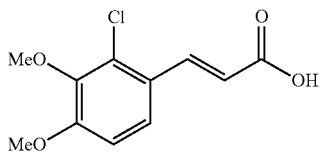

Compound w was prepared from 2-chloro-3,4-dimethoxybenzaldehyde according to general procedure I. 94% yield. White solid.

w: $^1$H NMR (400 MHz, in acetone d$_6$): δ 8.016 (d, J=16 Hz, 1H, Ar—CH=CH), 7.64 (d, J=8.8 Hz, 1H, aromatic CH), 7.11 (d, J=8.8 Hz, 1H, aromatic CH), 6.45 (d, J=16 Hz, 1H, Ar—CH=CH), 4.0 (s, 3H, OCH$_3$), 3.83 (s, 3H, OCH$_3$).

Synthesis of x

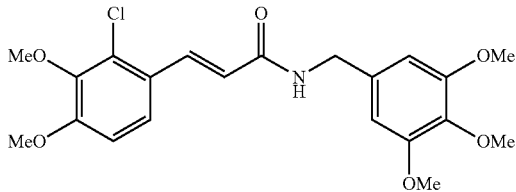

Compound w (1.5 g; 6.18 mmol) was dissolved in DMF (10 ml) and HOBt (920 mg; 6.8 mmol; 1.1 equiv.) was added. The mixture was cooled in an ice/salt-bath and a solution of DCC (128 g; 6.18 mmol) in DMF (7.5 ml) was added. After stirring for 15 minutes a solution of 3,4,5-trimethoxybenzylamine (1.22 g; 1.06 ml; 6.18 mmol) and Et$_3$N (1.0 ml; 7 mmol) in DMF (5 ml) was added. After stirring for another 10 minutes at 0° C., the mixture was allowed to reach room temperatures and stirred overnight. A small sample was taken and quenched in water and extracted with ether for TLC which was taken from the ether layer.

Work-up:

The reaction mixture was filtered and poured into cold water. The solids were filtered off, washed with cold water and dissolved in ether. White solid precipitated. The solid did not dissolve in HCl or in NaOH. NMR showed it to be the pure product x, 1.9 g (74%).

x: $^1$H NMR (400 MHz, in CDCl$_3$): δ 7.96 (d, J=15.6 Hz, 1H, Ar—CH=CH), 7.32 (d, J=8.8 Hz, 1H, aromatic CH), 6.82 (d, J=8.8 Hz, 1H, aromatic CH), 6.55 (s, 2H, aromatic CH), 6.34 (d, J=15.6 Hz, 1H, 1H, Ar—CH=CH), 5.90 (bt, 1H, NH), 4.50 (d, J=5.6 Hz, 2H, CH$_2$N), 3.89 (s, 3H, OCH$_3$), 3.87 (s, 3H, OCH$_3$), 3.86(s, 6H, OCH$_3$), 3.83 (s, 3H, OCH$_3$).

Synthesis of y

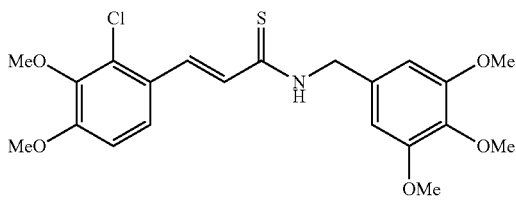

Compound y was prepared from x according to general procedure IV in 81% yield after column chromatography (hexane:ethyl acetate=1:1). Yellow powder.

y: $^1$H NMR (400 MHz, in CDCl$_3$): δ 8.048 (d, J=15.6 Hz, 1H, Ar—CH=CH), 7.35 (d, J=8.8 Hz, 1H, aromatic CH), 6.82 (d, J=8.8 Hz, 1H, aromatic CH), 6.78 (d, J=15.6 Hz, 1H, Ar—CH=CH), 4.9 (s, 2H, CH$_2$—Ar), 3.9 (s, 3H, OCH$_3$), 3.86 (d J=0.4, 9H, OCH$_3$), 3.85 (s, 3H, OCH$_3$).

Synthesis of 11

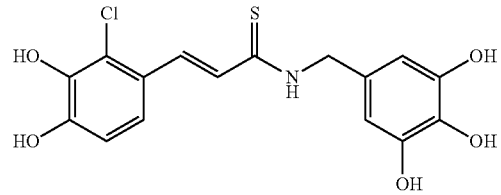

Figure 8:
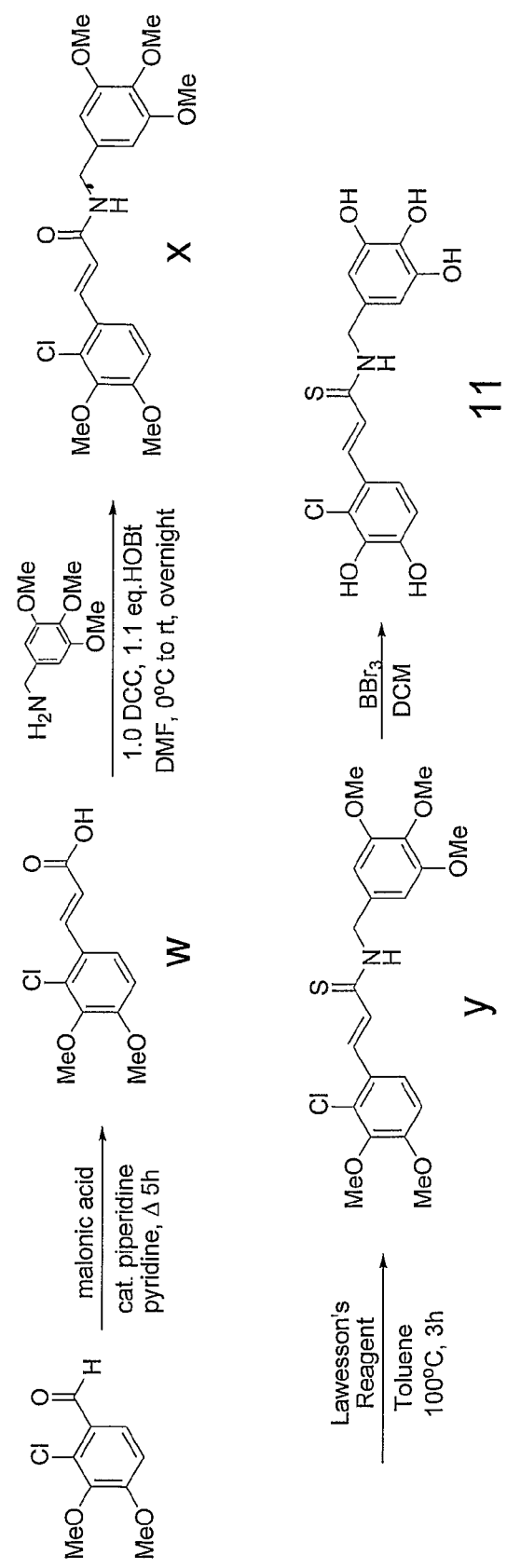
FIG. 8 Shows in schematic form an exemplary process for the synthesis of an exemplary novel Tyrphostin of the invention (compound 11).

The general procedure for the synthesis of compound 11 is drawn schematically in FIG. 8. Compound 11 was prepared from y according to general procedure V. Purification by preparative HPLC gave 40% yield of compound 11. Yellow solid.

11: $^1$H NMR (400 MHz, in Acetone-d$_6$): δ 9.21 (br. s, 1H, NH), 8.28 (d, J=15.2 Hz, 1H, Ar—CH=CH), 7.20 (d, J=8.8 Hz, 1H, aromatic CH), 7.09 (d, J=15.2 Hz, 1H, Ar—CH=CH), 6.85 (d, J=8.8 Hz, 1H, 1H, Ar—CH=CH), 6.45 (s, 2H, aromatic CH), 4.79 (s, 2H, CH$_2$N).

HPLC-96% at 16.27 min (5-95% ACN in 20 min 35 deg).

Synthesis of z

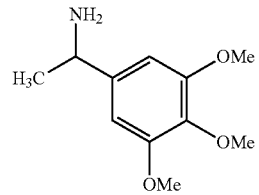

Ti(iPrO)$_4$ (12 ml; 40 mmol) was added to 3,4,5-trimethoxyacetophenone (4.2 g; 20 mmol). The flask was closed with a septum and 2N solution of NH$_3$ in EtOH (50 ml; 100 mmol NH$_3$) was added by syringe. The system was flushed with nitrogen via the septum and subsequently stirred for 6 hours at room temperature in the closed flask.

The mixture was cooled in an ice-bath and NaBH$_4$ (30 mmol; 1.13 g) was added. An exothermic reaction with strong gas evolution occurred. After gas evolution had ceased the cooling bath was removed and the mixture was stirred overnight at room temperature under an atmosphere of nitrogen. After several minutes the mixture turned from a clear solution into a suspension.

Work-Up:

The reaction was quenched with 60 ml of 2M ammonia. The mixture was filtered on a sintered glass filter and washed on the filter with DCM (3×50 ml). After separating the layers, the water layer was extracted with DCM (2×50 ml). The combined DCM fractions were extracted with 1M HCl (2×100 ml) and discarded. The aqueous extracts were washed with DCM (2×50 ml) and subsequently basified with 3 M NaOH till pH>12 followed by extraction with (new) DCM (3×100 ml). The DCM fractions were dried over Na$_2$SO$_4$ and DCM was evaporated. This gave 3.1 g of product z (73%) as a clear and colorless oil.

z: $^1$H-NMR (400 MHz, CDCl$_3$): δ 1.31 (d, 2H, J=6.4 Hz, CH$_3$), 3.77 (s, 3H, OCH$_3$), 3.81 (s, 6H, 2× OCH$_3$), 4.02 (q, 1H, J=6.4 Hz, CH-Me), 6.53 (s, 2H, aromatic).

Synthesis of aa

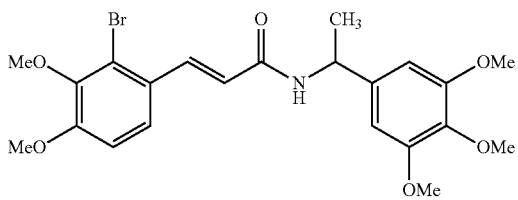 [SMILES: COc1cc(C(C)NC(=O)/C=C/c2ccc(OC)c(OC)c2Br)cc(OC)c1OC]

The 2-Bromo-3,4-dimethoxycinnamic acid (d; 490 mg; 1.70 mmol) was suspended in acetonitrile (20 ml). HOBt (252 mg; 1.87 mmol; 1.1 equiv.) was added, followed by DCC (350 mg; 1.70 mmol; 1.0 equiv.). The mixture was stirred for 10 minutes in an ice-bath and a solution of α-methyl-3,4,5-trimethoxybenzylamine (z; 375 mg; 1.78 mmol) and Et$_3$N (0.30 ml; 2.2 mmol; 1.3 equiv.) in acetonitrile (10 ml) was added. The mixture was allowed to reach room temperature and stirred overnight. TLC (hexane:ethyl acetate=1:2): spot on baseline, product spot with Rf=0.5. The mixture was filtered to remove DCU and the acetonitrile was evaporated. The crude mixture was taken up in DCM (100 ml) and the solution was washed with 2% aqueous K$_2$CO$_3$ (2×75 ml), 1M HCl (2×75 ml) and brine (50 ml). Drying of the organic layer over Na$_2$SO$_4$ and removal of the solvent in vacuo gave 800 mg product aa (98%).

aa: $^1$H-NMR (400 MHz, CDCl$_3$): 1.55 (d, 3H, J=6.8 Hz, CH$_3$—CH); 3.83 (s, 3H, OCH$_3$), 3.85 (s, 3H, OCH$_3$), 3.88 (s, 6H, 2× OCH$_3$); 3.90 (s, 3H, OCH$_3$); 5.18 (m, 1H, CH$_3$—CH), 5.87 (d, 1H, J=7.6 Hz, NH); 6.25 (d, 1H, J=15.2 Hz, CH=CH); 6.84 (d, 1H, J=8.4 Hz; aromatic); 7.29 (d, 1H, J=8.4 Hz; aromatic); 7.93 (d, 1H, J=15.2 Hz, CH=CH).

Synthesis of ab and ab'

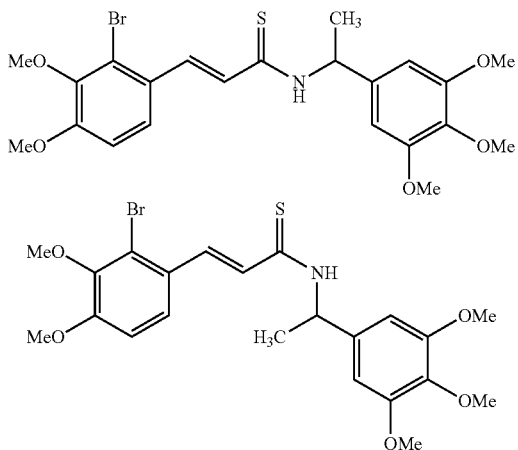

Compounds ab and ab' were prepared from aa according to general procedure IV. Purification by column chromatography (ethyl acetate:hexane=1:1) gave 53% pure product. Yellow solid.

ab and ab' (in a ratio of 3:4): $^1$H-NMR (400 MHz, CDCl$_3$): (1.35 (d; 3H, J=6.8 Hz, CH$_3$—CH, minor isomer); 1.65 (d; 3H, J=6.8 Hz, CH$_3$—CH, major isomer); 3.77 (s, 6H, 2× OCH$_3$, minor isomer), 3.805 (s, 3H, OCH$_3$), 3.807 (s, 3H, OCH$_3$), 3.81 (s, 3H, OCH$_3$), 3.82 (s, 3H, OCH$_3$), 3.83 (s, 3H, OCH$_3$), 3.84 (s, 3H, OCH$_3$), 3.85 (s, 6H, 2× OCH$_3$), 3.88 (s, 3H, OCH$_3$), 5.65 (m, 1H, CH—CH$_3$, minor isomer), 5.86 (m, 1H, CH—CH$_3$, major isomer), 6.36 (s, 2H, aromatic tri-methoxy-ring, minor isomer), 6.40 (d, 1H, J=12 Hz, CH alkene); 6.48 (d, 1H, J=8.8 Hz, aromatic brominated ring); 6.52 (d, 1H; 12 Hz, CH alkene), 6.62 (s, 2H, aromatic trimethoxy-ring, major isomer), 6.68 (d, 1H, J=15.6 Hz, CH alkene major isomer), 6.83 (d, 1H, J=8.8 Hz, aromatic brominated ring major isomer), 6.95 (d, 1H, J=8.8 Hz, aromatic brominated ring minor isomer), 7.22 (br.d, 1H, J=8.0 Hz, NH minor isomer), 7.30 (d, 1H; J=8.8 Hz, aromatic brominated ring), 7.55 (br.d, 1H, J=7.2 Hz, NH minor isomer), 8.04 (d, 1H, J=15.6 Hz, CH alkene).

Synthesis of 12a and 12b

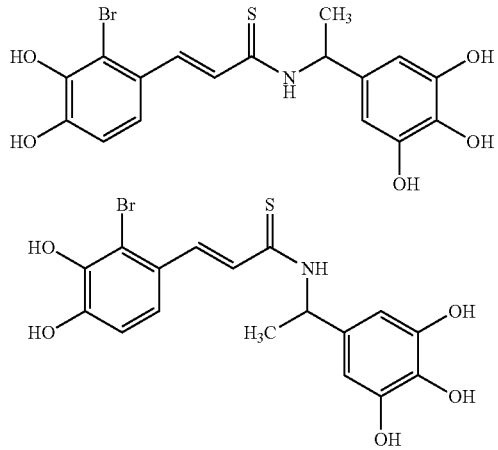

Figure 9:
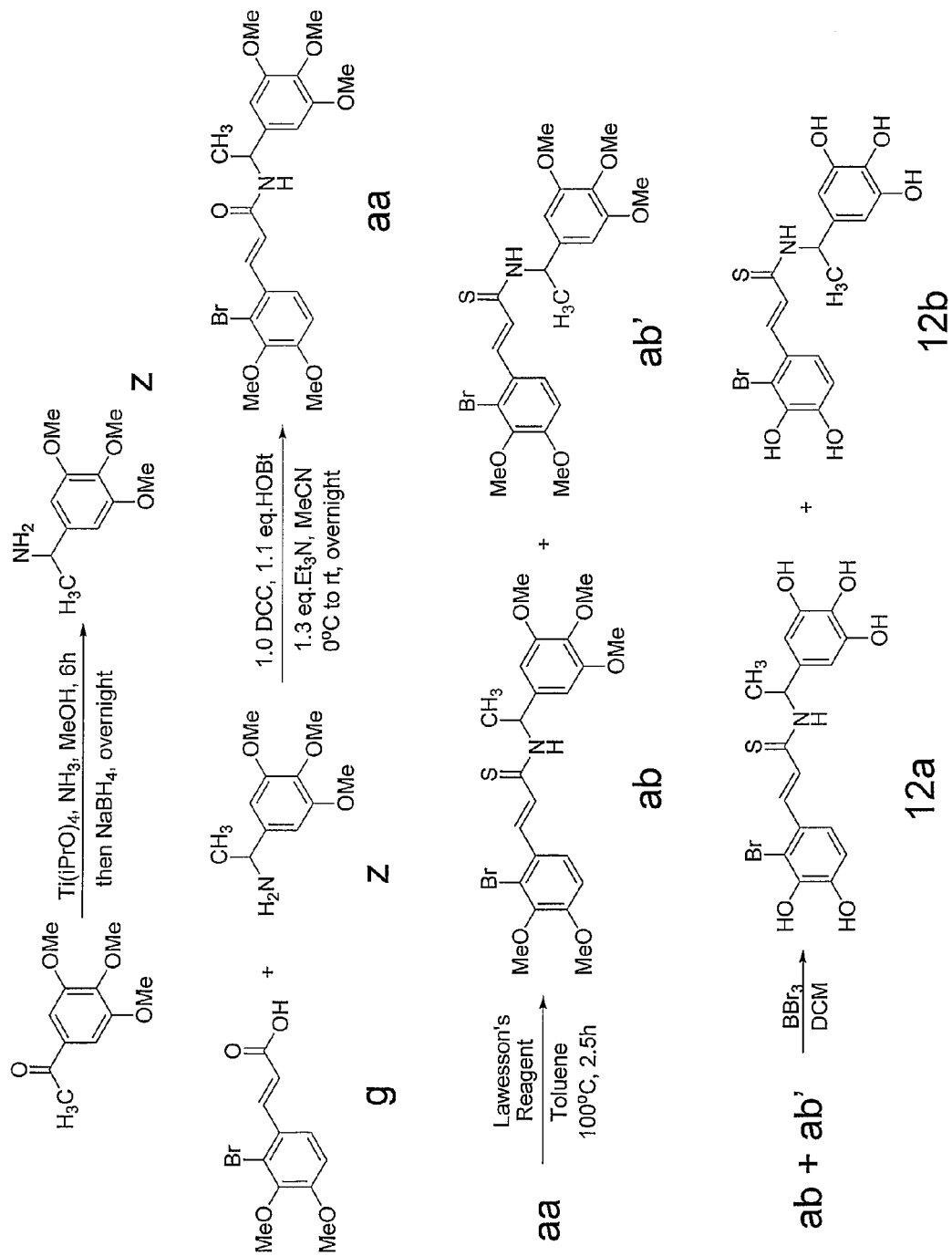
FIG. 9 Shows in schematic form an exemplary process for the synthesis of exemplary novel Tyrphostins of the invention (compounds 12a and 12b).

The general procedure for the synthesis of compounds 12a and 12b is drawn schematically in FIG. 9. Compounds 12a and 12b were prepared from isomers ab and ab', respectively according to general procedure V. Purification by preparative HPLC gave 70 mg product 12a and 12b, yellow solid. Deprotection of compounds ab and ab' resulted in formation of a product having a single $^1$H-NMR spectrum.

12: $^1$H-NMR (400 MHz, acetone-d$_6$): δ 1.53 (d, 3H, J=6.8 Hz, CH$_3$CH), 5.84 (m, 1H, CH—CH$_3$), 6.48 (s, 2H, aromatic), 6.88 (d, 1H, J=8.8 Hz, aromatic), 6.99 (d, 1H, J=15.2 Hz, alkene), 7.16 (d, 1H, J=8.8 Hz, aromatic), 8.27 (d, 1H, J=15.2 Hz, alkene), 9.18 (d, 1H, J=8.0 Hz, NH).

Synthesis of ac (1-(3-Bromo-4,5-dimethoxyphenyl)-1-ethanol)

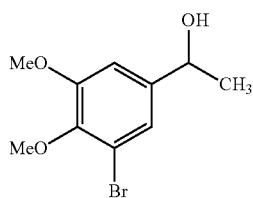

Under nitrogen, a solution of the 3-bromo-4,5-dimethoxybenzaldehyde (2.45 g; 10 mmol) in dry THF (10 ml) was added via syringe through a septum to a cold (ice-bath) solution of MeMgBr (15 mmol; 5.0 ml of 3.0 M Et$_2$O solution) diluted with 10 ml dry THF. After the addition, the mixture was stirred for 10 minutes at 0° C., then for 1 hour at room temperatures. TLC (Hex:EtOAc=3:1) indicated complete disappearance of the reactant and a new product spot with lower Rf (0.25 vs 0.5).

The reaction mixture was cooled again in an ice-bath and quenched by careful addition of saturated NH$_4$Cl-solution (15 ml total). The ether and THF were removed in vacuo and the mixture was extracted with ether (2×50 ml). The organic fraction was dried over Na$_2$SO$_4$, filtered and the ether was removed to give 2.45 g (94%) product ac.

ac: $^1$H-NMR (400 MHz, CDCl$_3$): δ 1.47 (d, 3H, J=6.4 Hz, CH$_3$), 3.83 (s, 3H, OCH$_3$), 3.88 (s, 3H, OCH$_3$), 4.81 (dd, AB-syst., 1H, J$_{AB}$=13.2 Hz, 6.4 Hz, CH—OH), 6.88 (d, 1H, J=3.2 Hz, aromatic), 7.10 (d, 1H, J=3.2 Hz, aromatic).

Synthesis of ad (3'-bromo-4',5'-dimethoxyacetophenone)

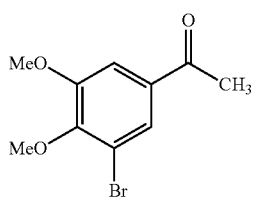

Jones' reagent was prepared as follows: concentrated sulfuric acid (4.6 ml) was added drop-wise to an ice cold solution of chromium trioxide (5.33 g) and water (8 ml). The volume of the solution was adjusted to 20 ml with water.

Compound ac (5.18 g, 19.8 mmol) was dissolved in acetone (200 ml) and Jones reagent (14 ml, 112 mmol oxygen) was added slowly with stirring. After 20 minutes at room temperature, 2-propanol (25 ml) was added and the mixture was filtered through celite. The organic phase was evaporated, the residue dissolved in ether, washed with water, and dried with sodium sulfate. Filtration and evaporation gave 4.37 g of yellowish pure product (85% yield).

ad: $^1$H-NMR (400 MHz, CDCl$_3$): δ 2.56 (s, 3H, CH$_3$—C=O), 3.93 (s, 6H, 2× OCH$_3$), 7.48 (d, J=2 MHz, 1H, aromatic); 7.73 d, J=1.6 MHz, 1H, aromatic).

Synthesis of ae (bromoacetamide derivative)

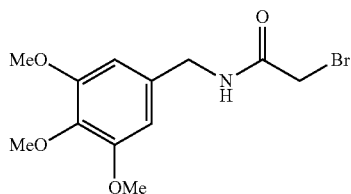 [SMILES: COc1cc(CNC(=O)CBr)cc(OC)c1OC]

To a mixture of K$_2$CO$_3$ (2.94 g; 21.3 mmol; 1.4 equiv.) and 3,4,5-trimethoxybenzylamine (3 g; 2.6 ml; 15.2 mmol) in DCM/water=3:2 (60 ml DCM; 40 ml water) at 0° C., bromoacetyl bromide (3.1 g; 1.33 ml; 15.3 mmol) was added drop-wise. The mixture was stirred overnight at room temperatures. A small sample was taken from the DCM layer for TLC (Hex:EtOAc=1:1) mainly showed the product (Rf=0.2), some amine (Rf=0.9) and a little spot on the baseline. More water (25 ml) was added, the layers were separated and the aqueous phase was extracted with DCM (2×50 ml). The combined DCM layers were washed once with 1N HCl, then again with water and dried over Na$_2$SO$_4$. Filtration and concentration in vacuo gave 4.07 g product (84%).

ae: $^1$H-NMR (400 MHz, CDCl$_3$): δ 3.76 (s, 3H, OCH$_3$), 3.78 (s, 6H, 2× OCH$_3$), 3.84 (s, 2H, CH$_2$Br), 4.31 (d, 2H, J=6 Hz, CH$_2$NH), 6.43 (s, 2H, aromatic), 7.0 (br.s., 1H, NH).

Synthesis of of (amidophosphonate)

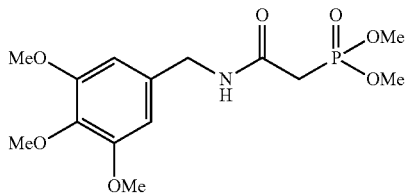 [SMILES: COc1cc(CNC(=O)CP(=O)(OC)OC)cc(OC)c1OC]

Bromoacetamide ae (4.0 g; 12.57 mmol) and trimethylphosphite (5 ml) were mixed and heated to 110° C. for 5 hours with an air-cooler on top of the flask. After cooling to room temperature, hexane (25 ml) was added and the mixture (2 phases) was stirred for 20 minutes and the hexane was removed carefully. This procedure was repeated twice in order to remove any remaining trimethylphosphite as much as possible. The oily product crystallized on standing and was washed two times with 10 ml of cold diethyl either. Filtration and removal of remaining ether in vacuo gave 3.97 g product af as a white solid (91%).

af: $^1$H-NMR (400 MHz, CDCl$_3$): δ 2.90 (d, 2H, J=20.8 Hz, CH$_2$—P), 3.76 (d, 6H, J$_{CP}$=12 Hz; 2× P—OCH$_3$), 3.81 (s, 3H, OCH$_3$); 3.85 (s, 6H, 2× OCH$_3$), 4.39 (d, 2H, J=6 Hz, CH$_2$N); 6.52 (s, 2H, aromatic); 6.93 (br.s., 1H, NH).

Synthesis of ag and ag'

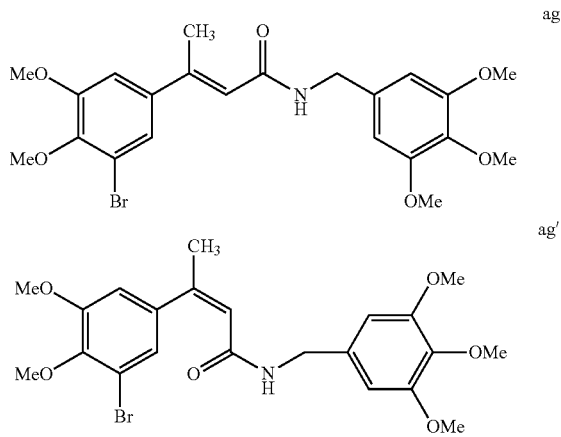

To a solution of the amidophosphonate af (1.74 g; 5 mmol) in dry THF (30 ml) at 0° C. under an nitrogen atmosphere NaH (60% dispersion in mineral oil; 250 mg; 6 mmol; 1.2 equiv.) was added. The resulting suspension was allowed to reach room temperatures and stirred until gas-evolution ceased (30 minutes). A nearly clear, slightly amber solution was formed. Subsequently a solution of 3'-bromo-4',5'-dimethoxyacetophenone ad (1.3 g; 5 mmol) in dry THF (10 ml) was added drop-wise via syringe, resulting in a brown-yellow suspension. The reaction was monitored by TLC (ethyl acetate:hexane=2:1). After 1 hour, disappearance of the starting materials was complete and two product spots were visible. A major spot with Rf=0.5, and minor spot with Rf=0.35. The mixture was stirred for a total of 1.5 hours at room temperatures and poured into ice cold water (100 ml). The THF was removed in vacuo and the residual was extracted with diethyl ether (3×100 ml). The combined organic fractions were washed with water (75 ml) and brine (50 ml) and dried over Na$_2$SO$_4$. After filtration and removal of the solvent the crude product was purified by column chromatography on silica gel (ethyl acetate:hexane=1:1 gradient to ethyl acetate:hexane=2:1). This gave major E-isomer ag (1.55 g; 66%) as a white solid and minor Z-isomer ag' (200 mg; 8.5%) as a white solid. Total combined yield: 74.5%. Two isomers in ratio 7.75:1.

$^1$H-NMR (400 MHz, CDCl$_3$):

E-isomer ag: δ 2.53 (d, 3H, J=1.6 Hz, CH$_3$), 3.80 (s, 3H, OCH$_3$), 3.84 (s, 6H, 2× OCH$_3$), 3.86 (s, 3H, OCH$_3$), 3.87 (s, 3H, OCH$_3$), 4.44 (d, 2H, J=5.6 Hz, N—CH$_2$), 5.94 (t, 1H, J=6 Hz, NH), 5.99 (m, 1H, CH=C—CH$_3$), 6.48 (s, 2H, aromatic), 6.88 (d, 1H, J=2.0 Hz, aromatic), 7.22 (d, 1H, J=2.0 Hz, aromatic).

Z-isomer ag': δ 2.11 (d, 3H, J=1.6 Hz, CH$_3$), 3.76 (s, 3H, OCH$_3$), 3.8 (s, 6H, 2× OCH$_3$), 3.81 (s, 3H, OCH$_3$), 3.82 (s, 3H, OCH$_3$), 4.20 (d, 2H, J=5.6 Hz, N—CH$_2$), 5.41 (br.t., 1H, NH), 5.94 (m, 1H, CH=C—CH$_3$), 6.32 (s, 2H, aromatic), 6.73 (d, 1H, J=2.0 Hz, aromatic), 7.03 (d, 1H, J=2.0 Hz, aromatic).

Synthesis of ah and ah'

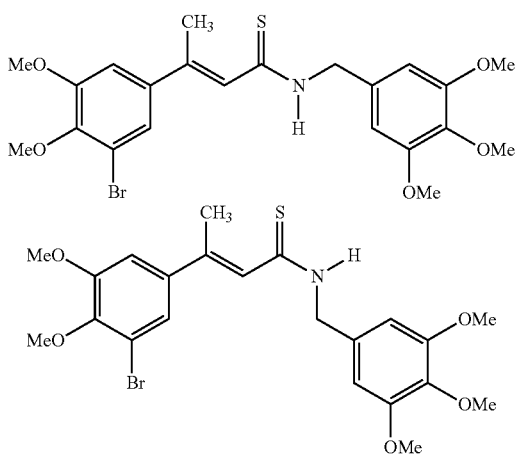

Compound ag (E-isomer; 1.35 g; 2.83 mmol) was suspended in toluene (25 ml) and Lawesson's Reagent (650 mg; 1.60 mmol; 0.57 equiv.) was added. A reflux condenser with drying tube was fitted on the flask and the mixture was heated to 115° C. with stirring for 2.5 hours. After cooling to room temperature, silica was added to the solution and the toluene was evaporated. TLC (hexane:ethyl acetate=2:1) indicated two isomers close together. The adsorbed crude product was purified by column chromatography on silica gel (hexane: ethyl acetate=2:1) to give 200 mg fast isomer ah (atropisomerism around thioamide group), 440 mg slow isomer ah' and 320 mg mixed isomers.

$^1$H-NMR (400 MHz; CDCl$_3$):

Fast Isomer ah: δ 2.08 (d, 3H, J=1.2 Hz, CH$_3$), 3.75 (s, 3H, OCH$_3$), 3.78 (s, 6H, 2× OCH$_3$), 3.81 (s, 3H, OCH$_3$), 3.82 (s, 3H, OCH$_3$), 4.48 (d, 2H, J=4.8 Hz, N—CH$_2$), 6.22 (s, 2H, aromatic), 6.40 (d, 1H, J=1.2 HZ, CH-alkene), 6.84 (d, 1H, J=2.0 Hz, aromatic), 6.95 (br.t, 1H, NH), 7.04(d, 1H, J=2.0 Hz, aromatic).

Slow isomer ah': δ 2.28 (d, 3H, J=1.2 Hz, CH$_3$), 3.82 (s, 3H, OCH$_3$), 3.83 (s, 3H, OCH$_3$), 3.85 (s, 6H, 2× OCH$_3$), 3.86 (s, 3H, OCH$_3$), 4.83 (d, 2H, J=5.2 Hz, N—CH$_2$), 6.49 (br.s, 1H, CH-alkene), 6.59 (d, 2H, aromatic), 6.88 (d, 1H, J=2.4 Hz, aromatic), 7.18 (d, 1H, J=2.4 Hz, aromatic), 7.53 (br.t, 1H, NH).

Synthesis of 13a and 13b

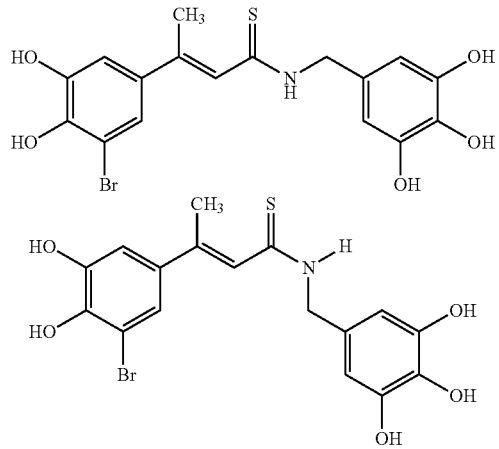

Figure 10:
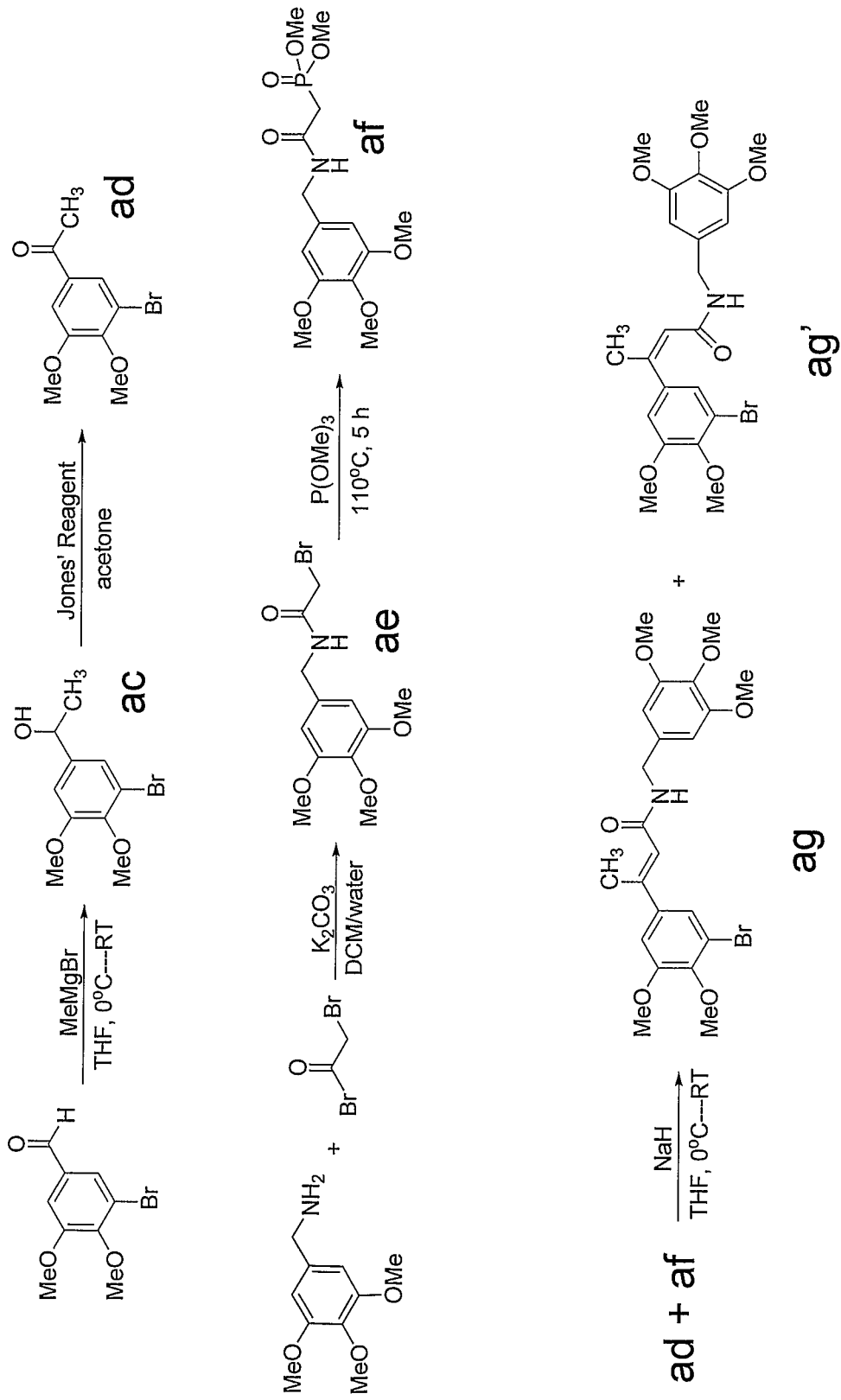
FIG. 10 Shows in schematic form an exemplary process for the synthesis of exemplary novel Tyrphostins of the invention (compounds 13a and 13b).
Figure 10:
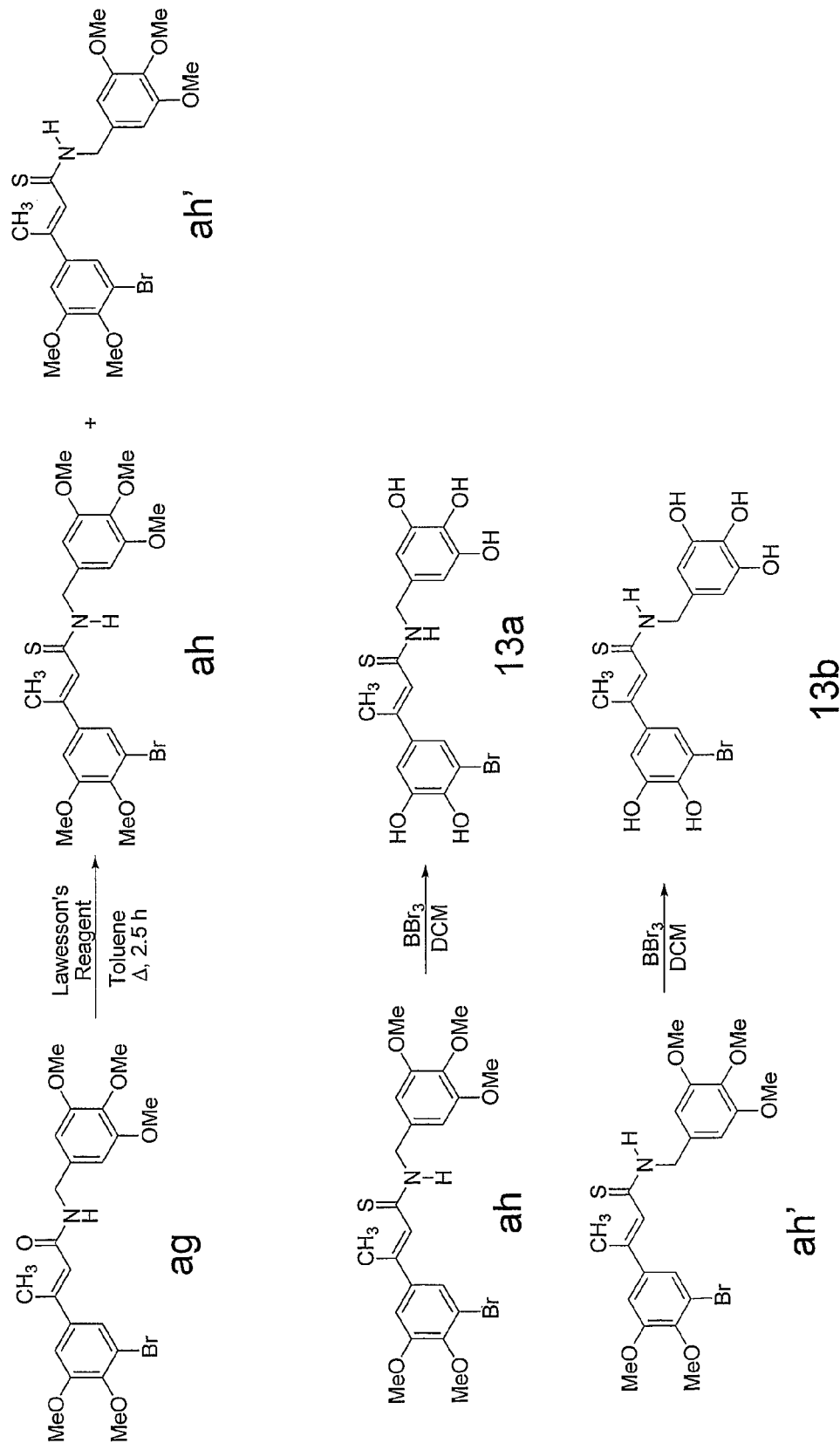

The general procedure for the synthesis of compounds 13a and 13b is drawn schematically in FIG. 10. Compound ah (190 mg; 0.4 mmol) was dissolved in DCM (20 ml), the solution was cooled in an ice-bath, and a solution of BBr$_3$ (0.85 ml; 2.25 g; 9.0 mmol; 22 equiv.) in DCM (10 ml) was added drop-wise (15 minutes). The solution was allowed to reach room temperatures and stirred for 5 hours. The mixture was cooled again in an ice-bath and ice cold water (50 ml) was added carefully. The DCM was removed in vacuo and the mixture was extracted with ethyl acetate (3×75 ml). The combined organic fractions were washed with brine and dried over Na$_2$SO$_4$. Filtration and evaporation of the solvent left crude product. Purification by preparative HPLC (5-95% ACN in 20 min 35 deg) gave 85 mg pure product. Yellow solid. Deprotection of compound ah' using the same conditions resulted in formation of a product having an identical $^1$H-NMR spectrum to that of 13a.

13: $^1$H-NMR (400 MHz, acetone-d$_6$): δ 2.29 (d, 3H, J=1.2 Hz, CH$_3$—C), 4.73 (d, 2H, J=5.2 Hz, CH$_2$—N), 6.48 (s, 2H, aromatic), 6.54 (d, 1H, alkene), 7.04 (d, 1H, J=2.4 Hz, aromatic), 7.17 (d, 1H, J=2.4 Hz, aromatic), 9.27 (br.s., 1H, NH).

Synthesis of ai

A solution of 5-dimethylaminomethyl-4-hydroxy-3-methoxybenzaldehyde (7.5 g; 35.8 mmol) in acetic anhydride (36 ml) was refluxed for 24 hours (drying tube on top of cooler). The volatile materials were removed on the rota-evaporator at 50-60° C. bath temperature. The obtained diacetate was allowed to cool to about 40° C. and concentrated HCl solution (37%, 40 ml) was added slowly. The mixture was allowed to stir at room temperature for 90 minutes during which most of the 5-chloromethyl-4-hydroxy-3-methoxybenzaldehyde precipitated. The precipitate was filtered, washed with ice-cold water (3×25 ml) and taken up in 150 ml ether (any insoluble material was removed via decantation). The solution was dried over Na$_2$SO$_4$. After filtration the part of the ether solution was evaporated to give 2.5 gram of the chloromethyl derivative as a light-brown crystalline solid. This was used immediately in the following step and the remaining ether solution was stored at −20° C.

5-Chloromethyl-4-hydroxy-3-methoxybenzaldehyde (2.5 g; 12.5 mmol) was dissolved in DMF (20 ml) and a solution of 2-mercaptothiazoline (1.5 g; 12.5 mmol) in DMF (10 ml) was added immediately, followed by the addition of triethylamine (1.7 ml; 12.5 mmol). The mixture was stirred at room temperatures for 60 hours and poured into cold water. The mixture was extracted with diethyl ether (2×100 ml). The combined ether fractions were dried over Na$_2$SO$_4$. Filtration and removal of the solvent in vacuo gave crude product contaminated with 2-mercaptothiazole. Purification by column chromatography (hexane:ethyl acetate=1:1) gave 1.85 g of pure ai.

ai: $^1$H-NMR (400 MHz, acetone-d$_6$): δ 3.38 (t, 2H, J=7.6 Hz, CH$_2$ thiazoline); 3.98 (s, 3H, OCH$_3$); 4.20 (t, 2H, J=7.6 Hz, CH$_2$ thiazoline); 5.09 (s, 2H, benzylic CH$_2$—S), 7.43 (d, 1H, J=1.6 Hz, aromatic), 7.55 (m, 1H, aromatic), 9.84 (s, 1H, HC=O).

Synthesis of aj

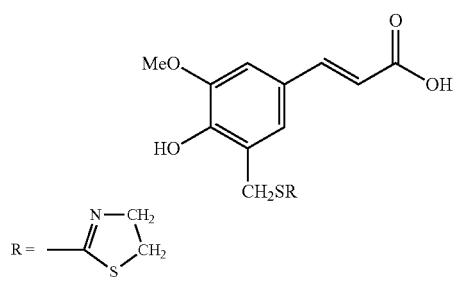

Aldehyde ai (1 equiv.) was dissolved in pyridine (3 ml/mmol) and malonic acid (1.5 equiv.) was added. After dissolution, five drops of aniline were added and the mixture was stirred in a closed flask for 24 hours. A reflux condenser with drying tube was fitted onto the flask and the mixture was heated to 55° C. for 4 hours. The reaction mixture was allowed to cool to room temperatures and transferred to a beaker placed in an ice-bath. Concentrated HCl was then added carefully until pH<2. The resulting precipitate was collected by filtration, washed with water and dried under reduced pressure to give a white solid.

Synthesis of ak

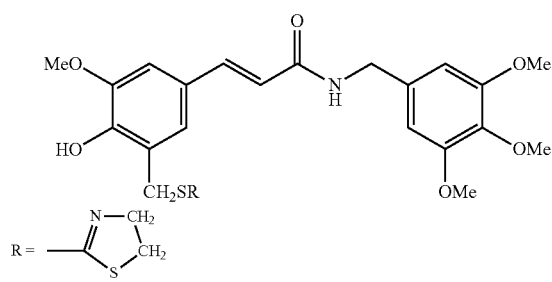

Compound aj (1 mmol) was suspended in acetonitrile (10 ml). HOBt (1.1 mmol; 1.1 equiv.) was added, followed by DCC (1.0 mmol; 1.0 equiv.). The mixture was stirred for 10 minutes in an ice-bath and a solution of α-methyl-3,4,5-trimethoxybenzylamine (z) (1.0 mmol) and Et$_3$N (1.3 mmol; 1.3 equiv.) in acetonitrile (10 ml) was added. The mixture was allowed to reach room temperatures and stirred overnight. The mixture was filtered to remove DCU and the acetonitrile was evaporated. The crude mixture was taken up in DCM (100 ml) and the solution was washed with 2% aqueous K$_2$CO$_3$ (2×75 ml), 1M HCl (2×75 ml) and brine (50 ml). Drying of the organic layer over Na$_2$SO$_4$ and removal of the solvent in vacuo gave product ak.

Synthesis of al

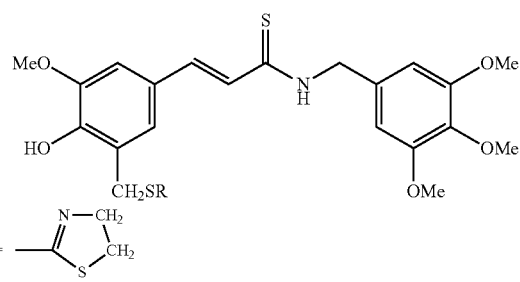

Compound al was prepared from ak according to general procedure IV.

Synthesis of 14

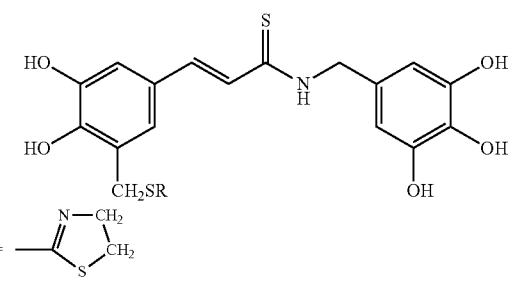

Figure 11:
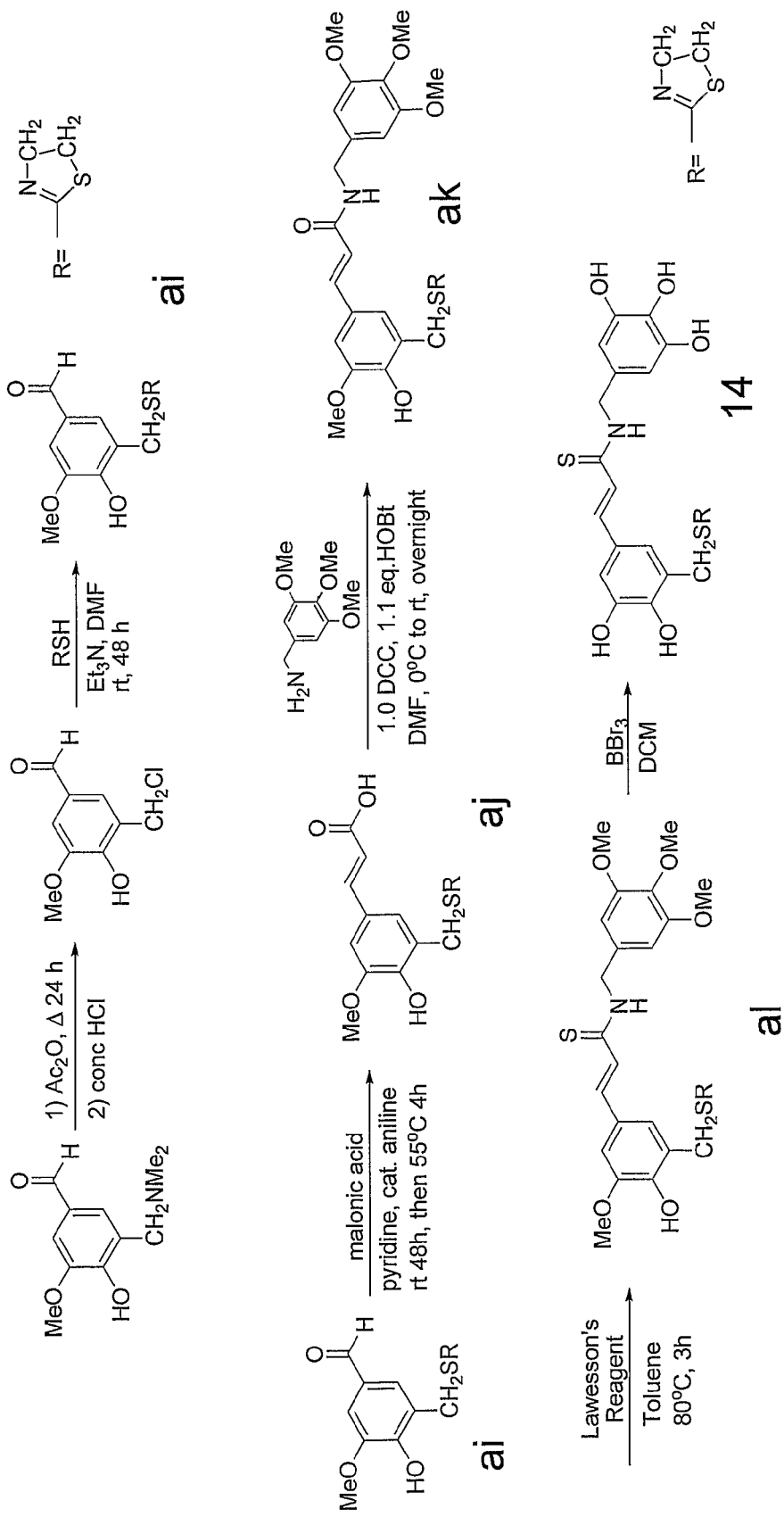
FIG. 11 Shows in schematic form an exemplary process for the synthesis of an exemplary novel Tyrphostin of the invention (compound 14).

The general procedure for the synthesis of compound 14 is drawn schematically in FIG. 11. Compound 14 was prepared from ak according to general procedure V. Purification by preparative HPLC (5-95% ACN in 20 min 35 deg) gave product 14.

Synthesis of am

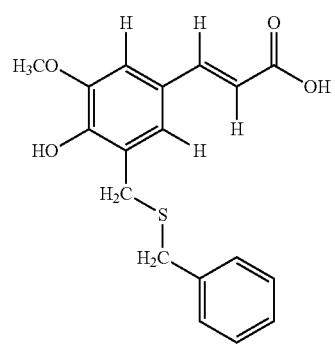 [SMILES: COc1cc(/C=C/C(=O)O)cc(CSCc2ccccc2)c1O]

Compound am is prepared according to a procedure similar to that described for compound aj.

Synthesis of an

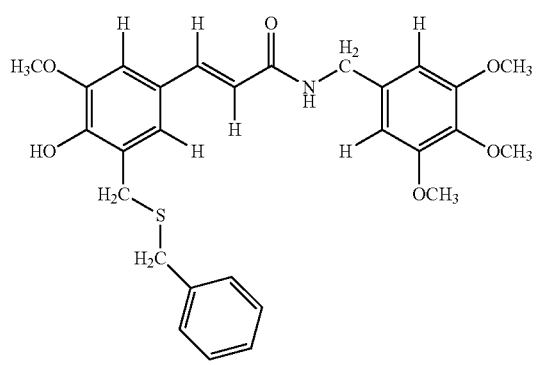 [SMILES: COc1cc(/C=C/C(=O)NCc2cc(OC)c(OC)c(OC)c2)cc(CSCc2ccccc2)c1O]

Compound an is prepared according to a procedure similar to that described for compound ak.

Synthesis of ao

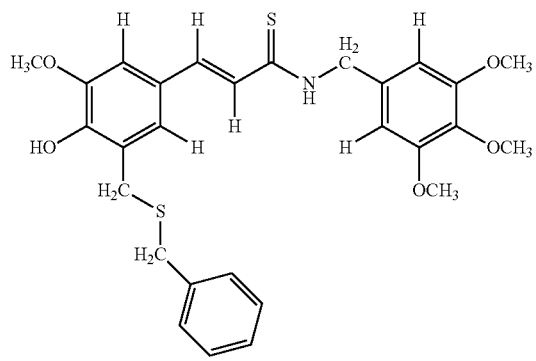

Compound ao is prepared according to general procedure IV.

Synthesis of 15

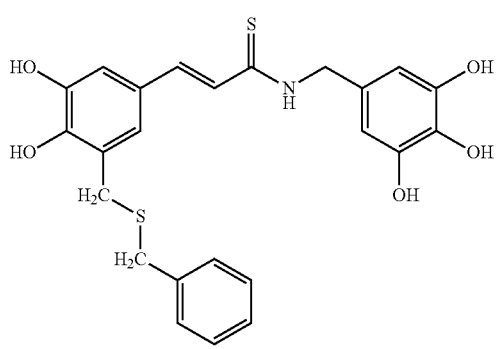

Figure 12:
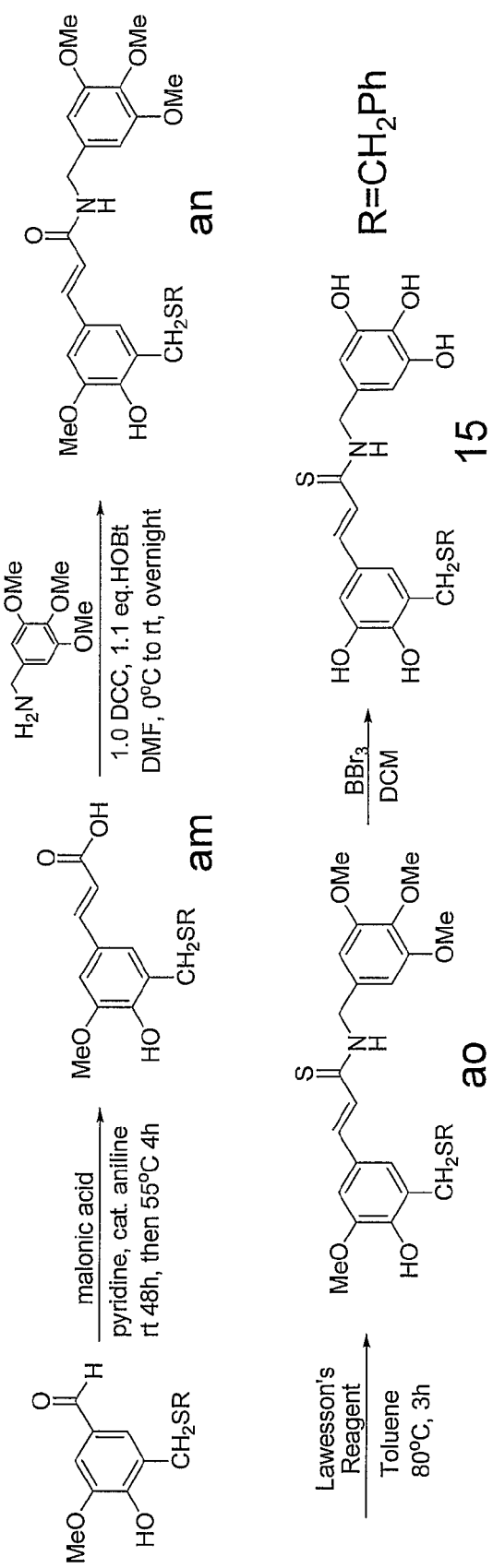
FIG. 12 Shows in schematic form an exemplary process for the synthesis of an exemplary novel Tyrphostin of the invention (compound 15).

The general procedure for the synthesis of compound 15 is drawn schematically in FIG. 12. The compound is prepared according to general procedure V.

Synthesis of ap

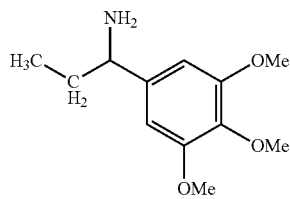 [SMILES: CCC(N)c1cc(OC)c(OC)c(OC)c1]

Compound ap is prepared according to a procedure similar to that described for compound z.

Synthesis of aq

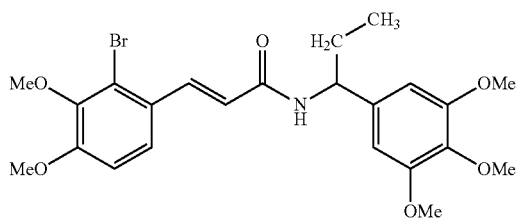 [SMILES: CCC(NC(=O)/C=C/c1ccc(OC)c(OC)c1Br)c1cc(OC)c(OC)c(OC)c1]

Compound aq is prepared from ap according to general procedure III.

Synthesis of ar and ar'

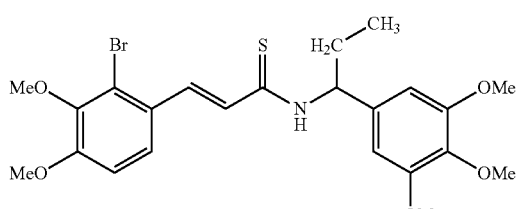

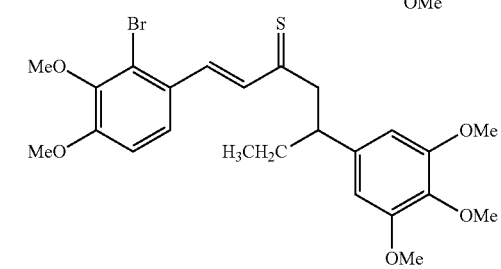

Compounds ar and ar' are prepared from aq according to general procedure IV.

Synthesis of 16

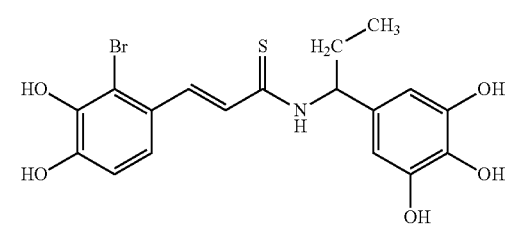 [SMILES: CCC(NC(=S)/C=C/c1ccc(O)c(O)c1Br)c1cc(O)c(O)c(O)c1]

Figure 13:
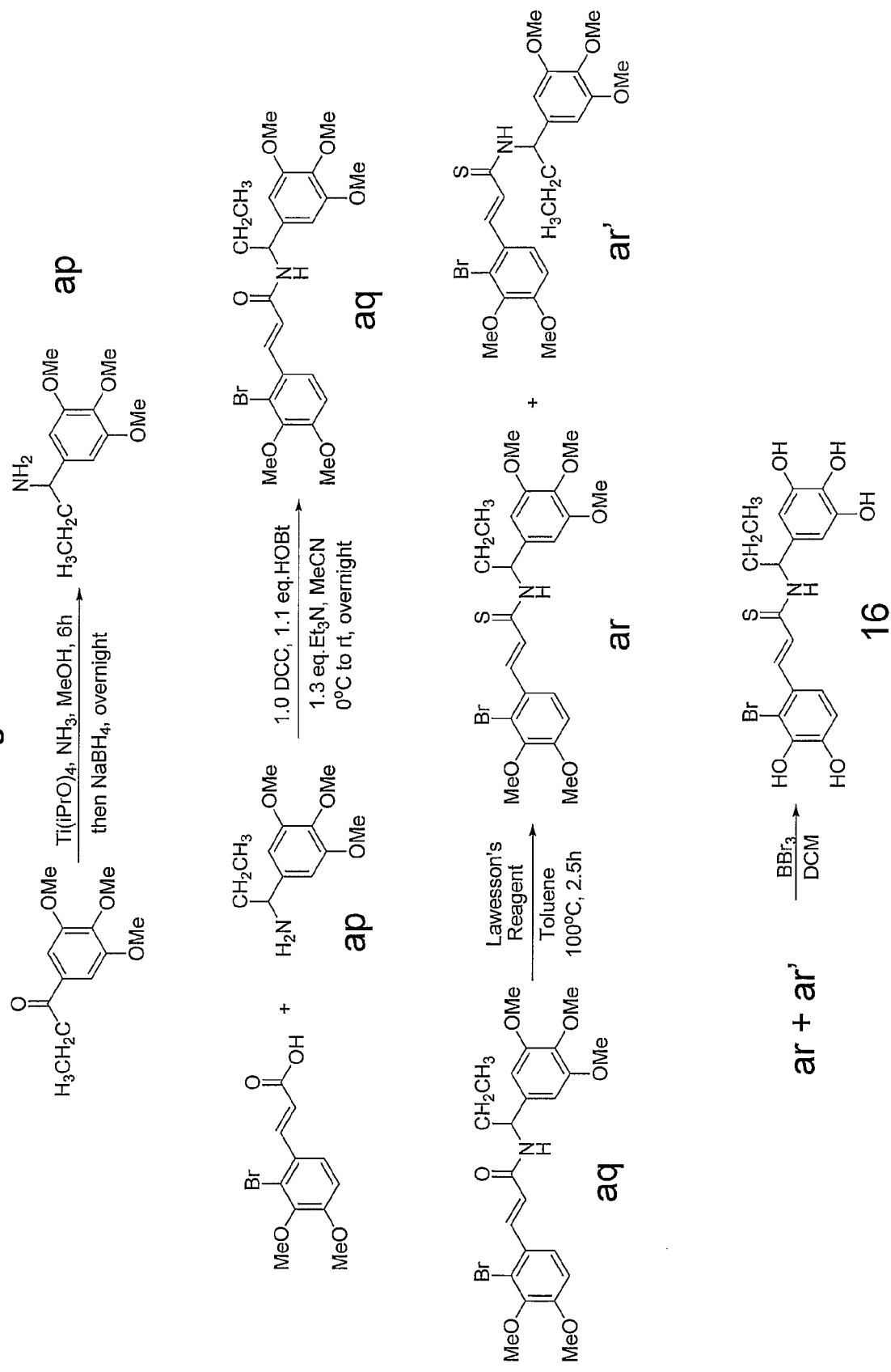
FIG. 13 Shows in schematic faun an exemplary process for the synthesis of an exemplary novel Tyrphostin of the invention (compound 16).

The general procedure for the synthesis of compound 16 is drawn schematically in FIG. 13. The compound is prepared from a mixture of ar and ar' according to general procedure V.

EXAMPLES 2-6

Biological Activity

Reagents and Antibodies

All chemicals used for chemical synthesis, namely bovine serum albumin, poly(Glu,Tyr) 4:1 (pGT), 2,2'-azido-bis-3-ethylbenzithiazoline-6-sulfonic acid, IGF1, methylene blue, 3-(4,5-dimethyl-2-thiazolyl)-2,5-diphenyl-2H-tetrazolium bromide (MTT) and diphosphorylated mitogen-activated protein kinase antibodies (pERK) were purchased from Sigma. Anti-phospho(Y896)IRS1 antibody was obtained from Oncogene Research Products, Germany; anti-IRS1 was obtained from Upstate Biotechnology, Inc. Anti-Akt1/2 (PKB), anti-ERK2, and anti-IGF1Rβ antibodies were obtained from Santa Cruz Biotechnology. Anti-phospho (T308)Akt, anti-phospho(Ser636/Ser639)IRS1 and anti-PARP antibodies were obtained from Cell Signaling Technology. Dulbecco's modified Eagle's medium (DMEM) and fetal calf serum (FCS) were obtained from Biological Industries, Bet-Haemek, Israel. DMSO was obtained from BDH.

EXAMPLE 2

Cell-free Inhibition of IGF1R-Catalyzed Substrate Phosphorylation

Purification of the IGF1R was based on the method described elsewhere (Steiner et al., *Eur. J. Pharmacol.* (2007), 562(1-2):1-11). Confluent $R^+$ cells overexpressing the human IGF1R were lysed in the presence of 10% glycerol, 50 mM HEPES, 1% Triton X-100, 150 mM NaCl, 5 μM EGTA, 0.24 mg/ml 4-(2-aminoethyl)-benzenesulfonyl fluoride, 10 μg/ml aprotinin, 5 μg/ml leupeptin, 25 mM benzamidine, and 10 μg/ml soybean trypsin inhibitor. The lysate was bound to immobilized lectin overnight at 4° C. and washed with 5 column volumes of HTN buffer (50 mM Hepes, 1% Triton X-100, and 150 mM NaCl). Additional washes were performed with 50 mM HEPES, 1% Triton X-100, 1 M NaCl and then with 10% glycerol/HTN. Semi-purified IGF1R was eluted with 0.5 M N-acetyl-D-glucosamine in 10% glycerol/HTN, snap frozen in liquid nitrogen, and kept at −70° C. In each of the preparations the only detectable protein tyrosine kinase activity was that of IGF1R.

The general protein tyrosine kinase substrate, poly (Glu, Tyr) 4:1 (pGT), was coated onto 96-well Maxisorp plates (Nunc) by adding 125 μl of 0.1 mg/ml pGT in PBS to each well. Plates were sealed and incubated for 16 hours at 37° C., washed twice with TBST (10 mM Tris-HCl, pH 7.5, 50 mM NaCl, and 0.1% Triton X-100) and once with DDW, dried for 2-3 hours, and stored at 4° C.

The receptor was incubated (10 ng/well) in the pGT-coated plates, with 50 mM $MgCl_2$, 0.04 mM $NaVO_3$ and 20 mM Hepes, pH 7.4, with or without inhibitors for 3 minutes at 30° C. The reaction was then initiated by addition of ATP and $MnAc_2$ to final concentrations of 10 μM ATP and 2 mM $MnAc_2$. The reaction was allowed to continue for 6 min at 30° C., until 0.5 M EDTA (0.05 ml/well) was added which caused the immediate stop of the reaction. The plate was then washed with TBS with 0.2% Tween-20 (TBST) and blocked for 30 min with 0.5% BSA in TBST. UB40 anti-phosphotyrosine hibridoma was added to the plate for 45 min at room temperature and the plate was washed 6 times with TBST. Then HRP-conjugated anti-mouse antibody (1:10,000 in 5% low fat milk in TBST) was added to the plate for 30 min at room temperatures and the plate was washed repeatedly with TBST. Detection was carried out with a color reagent, ABTS, in citrate-phosphate buffer, pH 4, with 0.004% $H_2O_2$ for 10 min and monitored at 405 nm, all at room temperatures. $IC_{50}$ values of inhibitors were calculated using the REGRESSION program. The assay was optimized with respect to the amount of IGF1R (partially purified from cells overexpressing IGF1R), reaction time, $Mn^{+2}$, $Mg^{+2}$ and ATP concentrations. The signal was linear for 30 min in the range of IGF1R protein concentrations up to 35 ng/well.

Compounds 4-13 of the present invention were tested for their inhibitory potential of IGF1R in a cell-free kinase assay. The preparations were exposed to increasing concentrations of compounds 4-13. $IC_{50}$ values were determined from the curves of IGF1R tyrosine kinase activity values versus compound concentration. As shown in Table 1, the compounds were found to inhibit IGF1R in a cell-free environment with $IC_{50}$ values ranging 0.03-0.22 μM. Thus, the compounds of the present invention are shown as potent inhibitors of IGF1R activity.

TABLE 1

$IC_{50}$ values of IGF1R activity in a cell-free kinase assay

| Compound No. | Cell-free kinase assay IC50 (μM) |
|---|---|
| 4 | 0.03 |
| 5 | 0.07 |
| 6 | 0.08 |
| 7 | 0.18 |
| 8 | 0.05 |
| 9 | 0.17 |
| 10 | 0.09 |
| 11 | 0.14 |
| 12 | 0.12 |
| 13 | 0.22 |

EXAMPLE 3

Anchorage-Independent Growth Assay (Colony Formation in Soft Agar)

Suspensions of separated A375 and U138MG cells were plated in 50 μl growth medium containing 0.3% agar on top of a 100 μl layer of growth medium containing 1% agar in 96-well plates. Growth medium (50 μl) supplemented with inhibitors at various concentrations was added on top. Six to seven days after plating, colonies were stained with 0.5% MTT for 4 hours, and dye was then extracted by the addition of 100 μl dissolving buffer, containing 5 gr sodium dodecyl sulfate, 8.75 ml DDW, 12.5 ml dimethyl formamide, 0.5 ml acetic acid and 0.07 ml HCl. Following incubation overnight at 37° C., optical density values were read at 570 nm in ELISA plate reader. The data was analyzed in Microsoft Excel, using the vehicle control as 100% proliferation. The assays were performed in triplicates. The values of $IC_{50}$ were derived from the dose-dependent growth curves obtained.

EXAMPLE 4

Inhibition of Cell Proliferation

Human ovary cancer A2780 cells lines were seeded at a density of 1000-5000 cells/well, human melanoma A375 cells were plated at a density of 2,500 cells/well, human colon carcinoma HCT116 cells were plated at a density of 2,000 cells/well, human colon carcinoma HCT15 cells were plated at a density of 3,000 cells/well, human colon carcinoma HT29 cells were plated at a density of 2,500 cells/well, human prostate carcinoma DU145 cells were plated at a density of 3,000 cells/well, human breast carcinoma MCF7 cells were plated at a density of 5,000 cells/well, human breast carcinoma SK-BR-3 cells were plated at a density of 2,500 cells/well, human breast carcinoma MDA MB 468 cells were plated at a density of 6,000 cells/well, human glioblastoma U138MG cells were plated at a density of 2,000 cells/well, human hepatocarcinoma HepG2 cells were plated at a density of 3,000 cells/well, human lung cancer A549 cells were plated at a density of 3,000 cells/well, human lung cancer NCI-H1975 cells were plated at a density of 5,000 cells/well, human osteosarcoma Saos-2 cells were plated at a density of 5,000 cells/well, human myeloma U266, RPMI8226, MM1S, CAG and ARH77 cells were plated at a density of 10,000 cells/well, human gastric carcinoma NCI-N87 cells were plated at a density of 5,000 cells/well. All cells were plated in 96-well plates in 90 µl growth medium containing 10% FCS, 100 units/ml penicillin and 100 µg/ml streptomycin. Inhibitors were added a day later in 10 µl of 1% DMSO in DDW to obtain final concentrations of 0, 0.1, 0.3, 1, 3, and 10 µM. The final concentration of DMSO (0.1% DMSO) was kept constant in all samples. Where specified, medium with inhibitors was refreshed a day and two days later. Following exposure of the cells to the inhibitors for 72 hours at 37° C., adhered cells were fixed in 0.5% gluteraldehyde in medium for 10 min, washed three times with DDW, once with 0.1M sodium borate buffer pH 8.5 and stained with 1% methylene blue dissolved in 0.1M borate buffer solution for 60 min. Excess dye was washed out and cell-bound dye was eluted with 200 µl/well of 0.1M HCl. The optical density values were read at 630 nm in ELISA plate reader. Non-adhered cells were exposed to WST-1 reagent for 5 hours following 72 hours treatment with the inhibitors, and optical density values were read at 630 nm in ELISA plate reader. The data was analyzed in Microsoft Excel, using the vehicle control as 100% proliferation. The assays were performed in triplicates. The values of $IC_{50}$ were derived from the dose-dependent growth curves obtained.

Compounds 4-13 of the present invention were tested for their inhibitory potential in cell proliferation assay. Human ovary cancer A2780 cells, melanoma A375 cells, colon carcinoma HCT116 cells, colon carcinoma HCT15 cells, colon carcinoma HT29 cells, prostate carcinoma DU145 cells, breast carcinoma MCF7, breast carcinoma SK-BR-3 cells, breast carcinoma MDA MB 468 cells, glioblastoma U138MG cells, hepatocarcinoma HepG2 cells, lung cancer A549 cells, lung cancer NCI-H1975 cells, osteosarcoma Saos-2 cells, multiple myeloma U266 cells, multiple myeloma RPMI8226 cells, multiple myeloma MM1S cells, multiple myeloma CAG cells, multiple myeloma ARH77 cells, and gastric carcinoma NCI-N87 cells were exposed to increasing concentrations of compounds 4-13. $IC_{50}$ values were determined from the curves of the optical density against compound concentration. The assay was performed in triplicates. As can be seen in Table 2, compounds 4-8 and 11-13 were found to inhibit several cancerous cell lines of various cancer types. Hence, the compounds of the present invention are potent as anti-cancerous agents.

TABLE 2 A&B

The inhibitory potential ($IC_{50}$ values in µM) of compounds 4-13 in cell proliferation assay of various cancer cell lines. The right column (CF) represents colony formation in soft agar.

A.

| | | Cell proliferation assay Compound No. IC50 (µM) | | | | | | | CF |
|---|---|---|---|---|---|---|---|---|---|
| Origin | Cell line | #4 | #5 | #6 | #7 | #8 | #9 | #10 | #5 |
| Ovarian cancer | A2780 | 0.7 | 0.1 | 0.3 | 0.8 | 0.6 | 9.2 | 9.5 | |
| Melanoma | A375 | 1.3 | 0.2 | 0.5 | 1.2 | 0.8 | 9.0 | >10 | 0.4 |
| Colon carcinoma | HCT116 | 1.1 | 0.3 | 0.5 | 1.2 | 0.6 | >10 | 10 | |
| | HCT15 | | 0.4 | | | | | | |
| | HT29 | 3.8 | 3.3 | 2.2 | >10 | 2.1 | >10 | >10 | |
| Prostate carcinoma | DU145 | 2.8 | 0.5 | 1.0 | 2.5 | 1.4 | >10 | >10 | |
| Breast carcinoma | MCF7 | 6.9 | 2.1 | 2.0 | 7.8 | 3.3 | >10 | >10 | |
| | SK-BR-3 | | 2.0 | | | | | | |
| | MDA MB 468 | 3.8 | 2.0 | 3.0 | 7.2 | 2.5 | >10 | >10 | |
| Glioblastoma | U138MG | 0.8 | 0.4 | 0.7 | 1.9 | 0.6 | >10 | >10 | 2.6 |
| Hepatocarcinoma | HepG2 | 0.8 | 0.4 | 0.6 | 2.0 | 0.9 | >10 | >10 | |
| Lung Cancer | A549 | | 1.1 | | | | | | |
| | NCI-H1975 | | 1.3 | | | | | | |
| Osteo-Sarcoma | Saos-2 | | 0.6 | | | | | | |
| Multiple Myeloma | U266 | | 0.9 | | | | | | |
| | RPMI8226 | | 0.5 | | | | | | |
| | CAG | | 0.4 | | | | | | |
| | MM1S | 1.0 | 0.3 | 0.4 | 1.0 | 0.8 | >10 | 10 | |
| | ARH77 | | 4.3 | | | | | | |
| Gastric Carcinoma | NCI-N87 | | 3.7 | | | | | | |

B.

| | | Cell proliferation assay Compound No. IC50 (µM) | | |
|---|---|---|---|---|
| Origin | Cell line | #11 | #12 | #13 |
| Melanoma | A375 | 0.4 | 0.7 | 9.0 |
| Colon | HCT15 | 0.7 | 0.8 | >10 |
| Prostate carcinoma | DU145 | 1.3 | 1.5 | >10 |
| Glioblastoma | U138MG | 0.7 | 0.5 | 6.2 |
| Hepato carcinoma | HepG2 | 1.3 | 2.3 | 4.6 |
| Multiple Meyeloma | RPMI8226 | 1.3 | 1.4 | >10 |

The potential of these compounds in inhibiting the proliferation of cancer cells was further assessed using a single administration as described hereinabove. The inhibitory potential following a single administration of compound 5 (+−−) was compared to the inhibitory potential of compound 5 when refreshment of the medium was performed every day (+++) or a day following the first administration (++−) or two days following the first administration (+−+). The inhibitory potential was tested in a cell proliferation assay of melanoma A375 cells. Table 3 shows that all administration protocols provided the same $IC_{50}$ when exposed to compound 5. It is therefore contemplated that compound 5 is a potent inhibitor of cancer cell proliferation even upon a single administration.

TABLE 3

IC$_{50}$ values of compound 5 in A375 cell proliferation
assay testing various regimens of administration.

| Treatment | IC$_{50}$ (µM) |
|---|---|
| +++ | 0.6 |
| +-- | 0.6 |
| ++- | 0.6 |
| +-+ | 0.6 |

(+) refers to treatment and (−) refers to no additional treatment

In order to further assess the inhibitory potential of compound 5, a replacement of the inhibitor-containing medium with fresh medium without the inhibitor (compound 5) a day (+−−) or two days (++−) following treatment was performed. The inhibitory potential was tested in melanoma A375 cell proliferation. As can be seen from Table 4, all treatment protocols inhibited cell proliferation at IC$_{50}$ values of 0.6-1 µM.

TABLE 4

IC$_{50}$ values of compound 5 in A375 cell proliferation
assay testing the effect of the inhibitor washout.

| Treatment | IC$_{50}$ (µM) |
|---|---|
| +++ | 0.6 |
| +-- | 1 |
| ++- | 0.6 |
| +-+ | 0.8 |

(+) refers to treatment and (−) refers to washing out

EXAMPLE 5

Inhibition of IGF1R Related Signaling in Cancer Cells

Tyrosine autophosphorylation of the β-subunit of IGF1R as well as downstream signaling induced by IGF1R were assayed in human breast cancer MCF7 cells and in melanoma A375 cells. Cells were seeded in 6-well plates (250,000 cells/well) and 24 hours later medium was replaced by serum-free medium (RPMI supplemented with 100 units/ml penicillin and 100 µg/ml streptomycin). Following 20 hours of serum-starvation, medium was replaced with serum-free medium containing various concentrations of the inhibitors in 0.1% DMSO for an additional 4-5 hours. Cells were then stimulated for 5 minutes with 50 ng/ml IGF-1, washed twice with PBS and lysed by boiling sample buffer (10% glycerol, 50 mM Tris-HCl, pH 6.8, 3% SDS, and 5% β-mercaptoethanol). Equal amounts of protein per lane were separated by 8% SDS-PAGE and transferred to a nitrocellulose membrane (Sartorius AG). Phosphorylated proteins were immunoblotted with anti-pIGF1R (phospho-IGF1R), anti-phosphotyrosine-IRS1 (pY-IRS1), anti-phospho(T308)Akt (pPKB), anti-phospho-Erk ($_p$ERK) and anti-phospho-Ser$^{636/639}$-IRS1 (pS$^{636/639}$-IRS1) antibodies. Detection was performed with horseradish peroxidase-conjugated secondary antibody using the ECL system. Blots were then stripped of antibodies, blocked with TBST with 5% low fat milk and re-probed with antibodies detecting both the phosphorylated and the non-phosphorylated corresponding proteins e.g. IGF1Rβ, IRS1, PKB, and ERK. Anti-actin antibodies served as control.

In addition, lysates were prepared from cells exposed to inhibitors at various concentrations for 24 hours in the presence or the absence of FCS without stimulation. Lysate preparation and western blot were performed as described above. Apoptosis was detected by immunoblotting with rabbit anti-PARP antibodies, which interact both with the intact PARP and the cleaved PARP.

Figure 14:
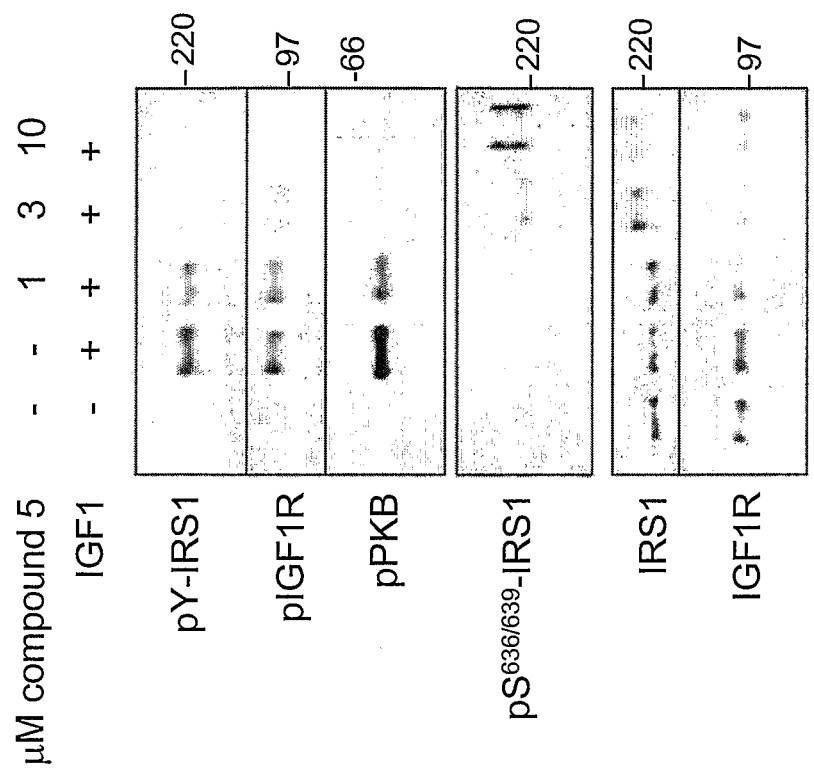
FIG. 14 Shows the inhibitory effect of compound 5 on IGF1R related cell signaling in human melanoma A375 cells.
Figure 15:
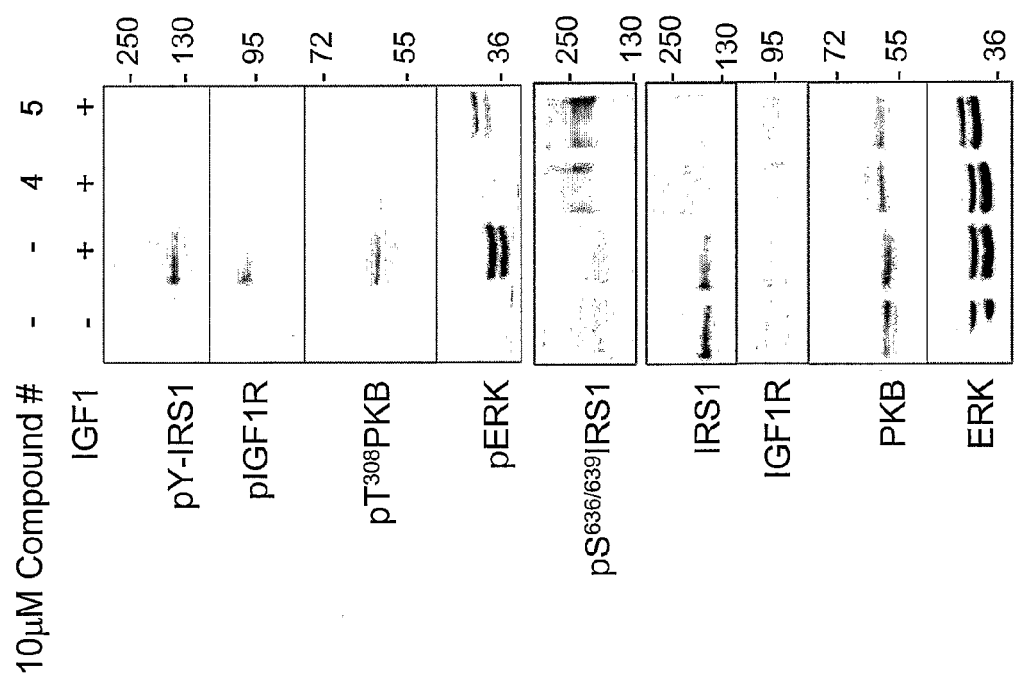
FIG. 15 Shows the inhibitory effect of compounds 4 & 5 on IGF1R related cell signaling in human breast cancer MCF7 cells.
Figure 16:
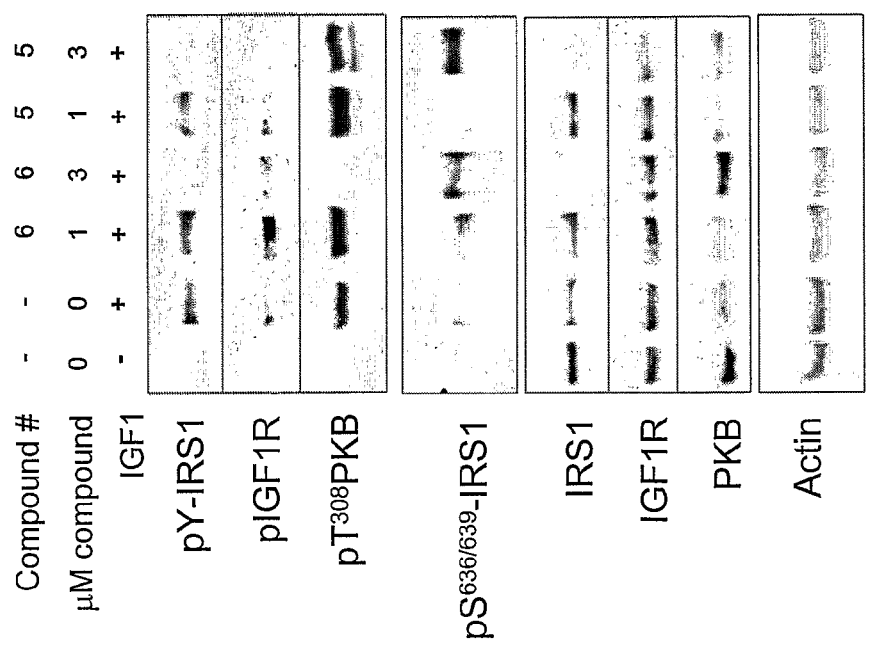
FIG. 16 Shows the inhibitory effect of compounds 5 & 6 on IGF1R related cell signaling in human melanoma A375 cells.

Compounds 4, 5 and 6 of the present invention were tested for their effect on several components of the IGF1R signaling axis, including IGF1R, IRS1, PKB and ERK. As can be seen in FIGS. 14-16, compounds 4, 5 & 6 inhibited the IGF1-induced tyrosine phosphorylation of IRS1, a direct substrate of IGF1R, and the IGF1-induced activation of the downstream signaling component PKB, a central antiapoptotic signaling protein. In MCF7 cells the IGF1-induced ERK activation was also inhibited (FIG. 15). These results indicate an inhibition of the IGF1R related signaling axis. In addition, the compounds were found to induce serine phosphorylation of IRS1, followed by its degradation (FIGS. 14-16, pS$^{636/639}$-IRS1 and IRS1). Without being bound by any theory or mechanism of action, Ser-phosphorylation of IRS1 induces decoupling of IRS1 and IGF1R and, therefore, inhibits IGF1R signaling. This phosphorylation and the decrease in IRS1 levels result in a long-term inhibition of IGF1R signal transduction.

EXAMPLE 6

Inhibition of Ovarian and Melanoma Tumor Growth In-Vivo

Human melanoma A375 cells (ATCC, 2×10$^6$ cells per mouse) were injected subcutaneously into the flank of Nude:Hsd mice. Eight days later, when tumors were formed, mice were divided into 3 groups with similar average tumor size of 120 mm$^3$. Compound 5 was injected IP either daily at doses of 50 mg/kg for 12 days or every other day at doses of 100 mg/kg for 6 days, dissolved in 2% EtOH, 6% Tween-80 in DDW at volume of 10 ml/kg. The Veh group received daily 2% EtOH, 6% Tween-80 in DDW at volume of 10 ml/kg. Groups were composed of 7-8 mice per group. The length (l) and the width (w) of the tumors were measured twice a week, as well as the mouse body weight. The volumes of the tumors were calculated as follows: v=lw$^2$/2. Graphs present average volumes of the tumors versus days following treatment initiation.

The procedure was followed for the A2780 ovary cancer cell in-vivo study with the following modifications:

Human ovary cancer A2780 cells (ECACC, 2×10$^6$ cells per mouse) were injected subcutaneously into the flank of female Nude:Hsd mice (purchased from Harlan). When tumors were formed, mice were divided into 3 groups with similar average tumor size of ~25 mm$^3$ and treatments initiated. Compound 5 was injected IP daily at doses of 25 mg/kg suspended in PBS. The Veh group received PBS. The CDDP group received 8 mg/kg CDDP (Cisplatin) twice a week.

Figure 17:
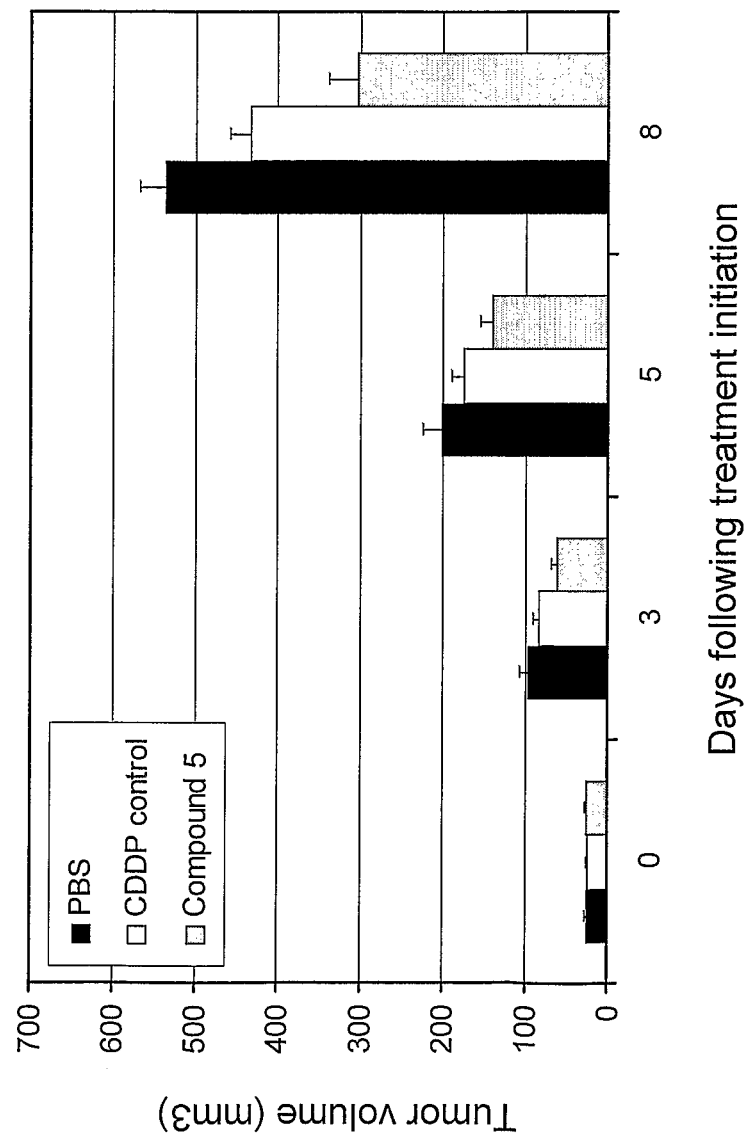
FIG. 17 Shows the inhibitory effect of compound 5 on ovarian cancer A2780 tumor growth.
Figure 18:
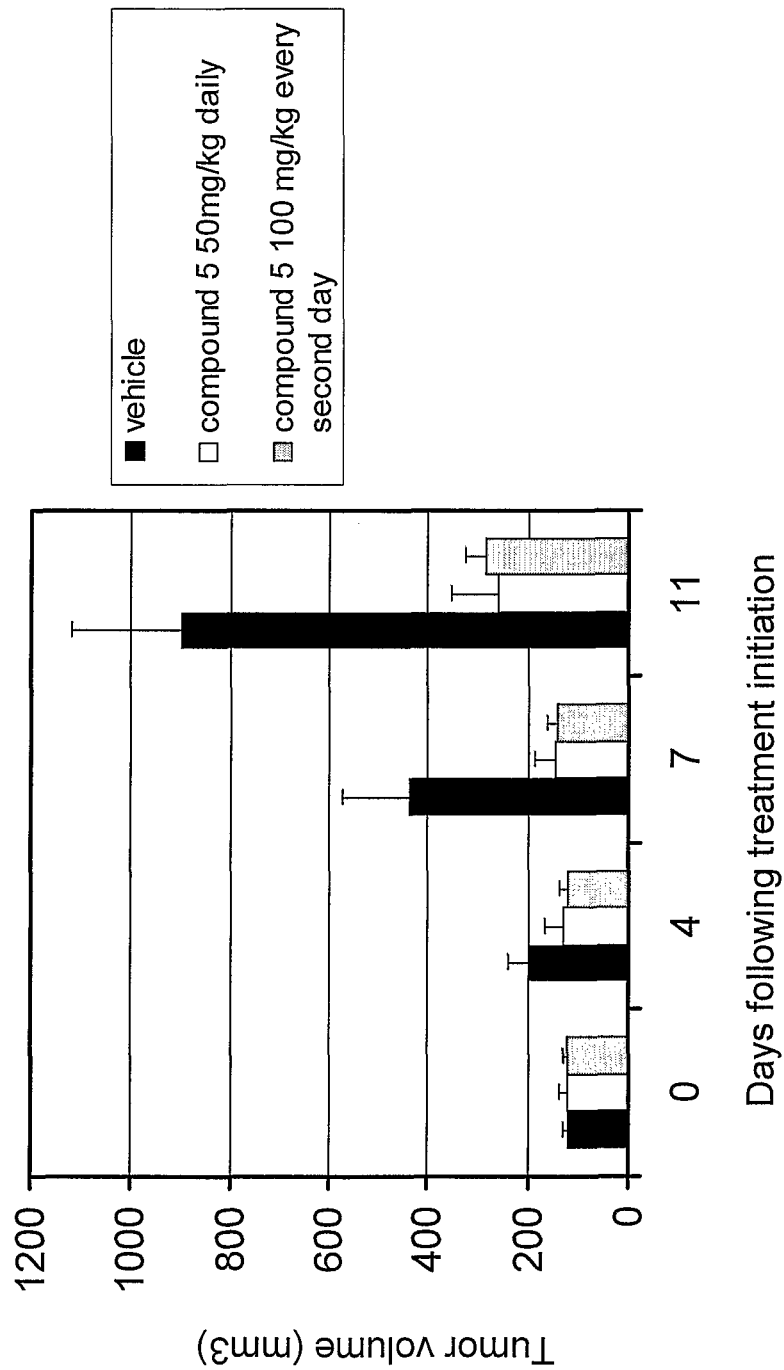
FIG. 18 Shows the inhibitory effect of compound 5 on A375 tumor growth.

Compound 5 of the present invention was tested for its in-vivo effects on the growth of human ovarian cancer and melanoma xenografts in nude mice. The mice were treated with daily or alternate day IP injections, at the specified doses. In the ovarian cancer experiment, CDDP treatment served as control. As shown in FIGS. 17 & 18, compound 5 exerts a 45% inhibition of ovarian tumor growth (in comparison to 14% CDDP-induced inhibition), and 70% inhibition of melanoma tumor growth.

While certain embodiments of the invention have been illustrated and described, it is to be clear that the invention is not limited to the embodiments described herein. Numerous modifications, changes, variations, substitutions and equivalents will be apparent to those skilled in the art without depart-

What we claim is:

1. A compound represented by the structure of formula 1:

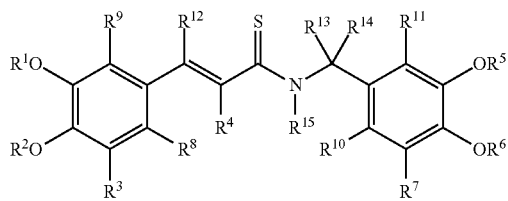

wherein $R^1$, $R^2$, $R^5$ and $R^6$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $(CH_2CH_2O)_nH$, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, acyl and a functional group that gives rise to hydroxyl upon hydrolysis;

$R^3$, $R^4$, $R^7$, $R^8$, $R^9$, $R^{10}$, $R^{11}$, $R^{12}$, $R^{13}$ and $R^{14}$ are each independently selected from H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl; $(C_1$-$C_4)$-alkylheteroaryl, halogen, haloalkyl, $NO_2$, CN, $N_3$, $SO_2R^a$, $COOR^a$, $CSNR^aR^b$, $CSOR^a$, $OR^a$, $CONR^aR^b$, $NR^aR^b$, $SR^a$, and $CH_2SR^a$, wherein $R^a$ and $R^b$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, $C_3$-$C_7$ cycloalkyl, aryl, heterocyclyl, heteroaryl, $(C_1$-$C_4)$-alkylaryl, $(C_1$-$C_4)$-alkylheterocyclyl, $(C_1$-$C_4)$-alkylheteroaryl, haloalkyl, $(CH_2CH_2O)_nH$, acyl or a functional group that gives rise to hydroxyl upon hydrolysis; and $R^{15}$ is H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, haloalkyl, or $OR^b$ wherein $R^b$ is independently H or $C_1$-$C_4$ alkyl;

provided that when $R^1$, $R^2$, $R^5$ and $R^6$ are H, $C_1$-$C_4$ alkyl, acyl or a functional group that gives rise to hydroxyl upon hydrolysis; $R^3$ and $R^7$ are H, halogen, haloalkyl or $OR^c$ wherein $R^c$ is H, $C_1$-$C_4$ alkyl, acyl or a functional group that gives rise to hydroxyl upon hydrolysis; and $R^4$ is H or CN; then at least one of $R^8$-$R^{15}$ is not H, including salts, hydrates, solvates, polymorphs, optical isomers, geometrical isomers, enantiomers, diastereomers, and mixtures thereof.

2. A compound according to claim 1, wherein $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen.

3. A compound according to claim 1, wherein $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen.

4. A compound according to claim 1, wherein $R^1$, $R^2$, $R^5$ and $R^6$ are each H or a functional group that gives rise to hydroxyl upon hydrolysis.

5. A compound according to claim 1, wherein $R^7$ is H or $OR^a$ and $R^1$, $R^2$, $R^5$, $R^6$, and $R^a$ are each H or a functional group that gives rise to hydroxyl upon hydrolysis.

6. A compound according to claim 1, wherein $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl or $C_1$-$C_4$ alkyl-$C_2$-$C_6$ alkynyl.

7. A compound according to claim 1, wherein at least one of $R^{13}$ and $R^{14}$ is H or $C_1$-$C_4$ alkyl.

8. A compound according to claim 1, wherein $R^3$, $R^4$, $R^7$, $R^8$, $R^9$, $R^{10}$, $R^{11}$, $R^{12}$, $R^{13}$ and $R^{14}$ are each independently H, halogen, haloalkyl, OH, $NO_2$, CN, or $CH_2SR^a$, wherein $R^a$ is as defined in claim 1.

9. A compound according to claim 1, wherein $R^4$ is H or CN.

10. A compound according to claim 1, wherein $R^4$, $R^{11}$, $R^{12}$, $R^{13}$, $R^{14}$ and $R^{15}$ are each H.

11. A compound according to claim 1, wherein $R^{13}$, $R^{14}$ and $R^{15}$ are each H.

12. A compound according to claim 1, wherein $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H, wherein $R^a$ is as defined in claim 1.

13. A compound according to claim 1, wherein $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$, $R^{14}$ and $R^{15}$ are each H, or a $C_1$-$C_4$ alkyl, wherein $R^a$ is as defined in claim 1.

14. A compound according to claim 1, wherein $R^1$, $R^2$, $R^5$ and $R^6$ are each H or a functional group that gives rise to hydroxyl upon hydrolysis;

$R^3$, $R^8$, and $R^9$ are each independently H, halogen, haloalkyl, or $CH_2SR^a$;

$R^7$, $R^{10}$ and $R^{11}$ are each independently H, halogen, haloalkyl, OH or a functional group that gives rise to hydroxyl upon hydrolysis; and $R^4$, $R^{12}$, $R^{13}$, $R^{14}$ and $R^{15}$ are each H, or $C_1$-$C_4$ alkyl, wherein $R^a$ is as defined in claim 1.

15. A compound according to claim 1, selected from the group consisting of:

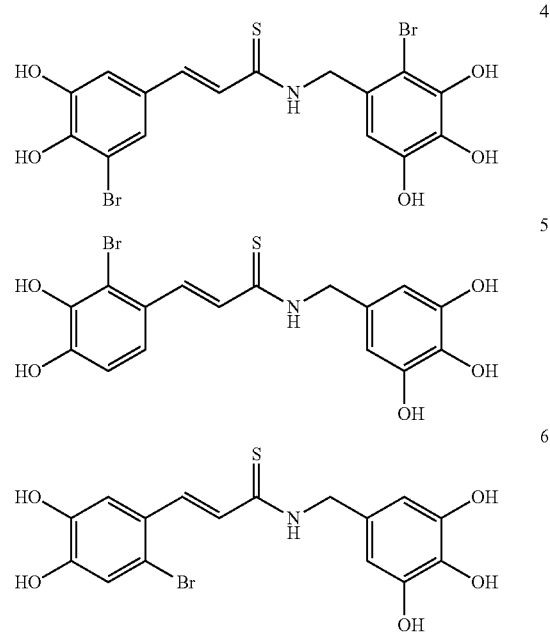

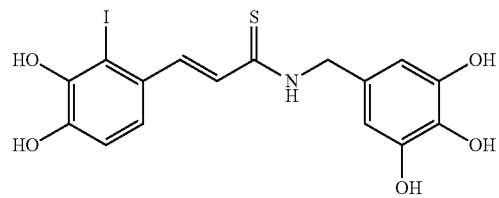
7
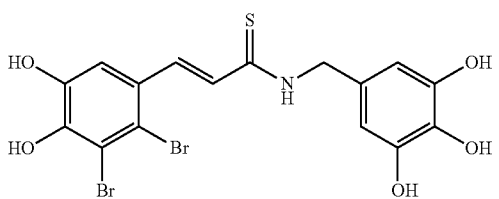
8a
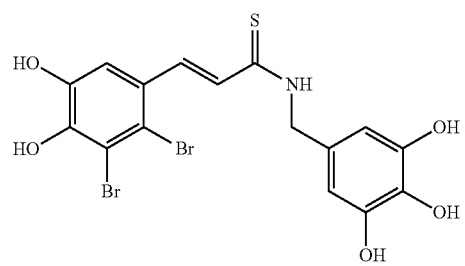
8b
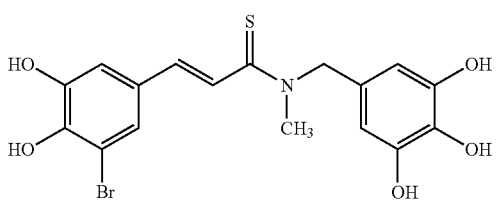
9a
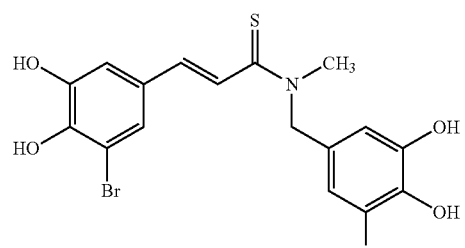
9b
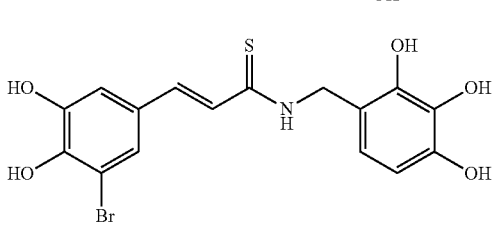
10
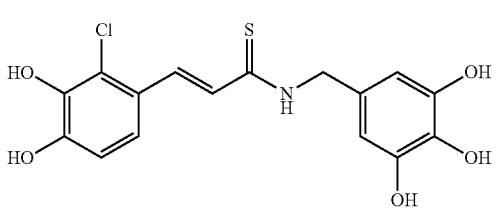
11
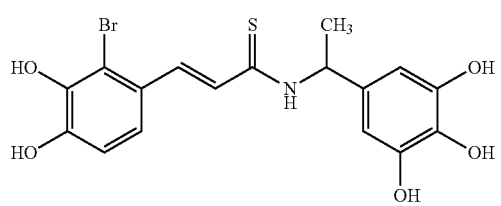
12a
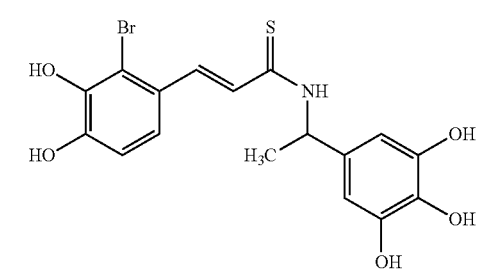
12b
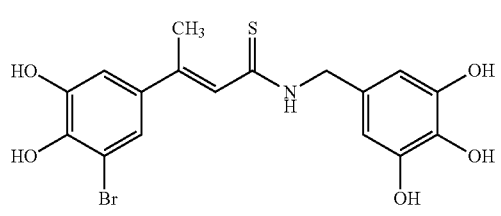
13a
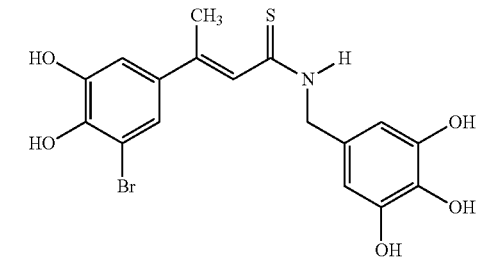
13b
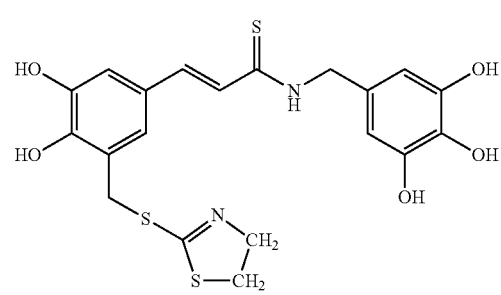
14
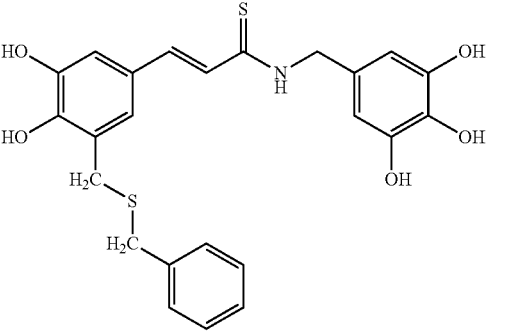
15
and -continued

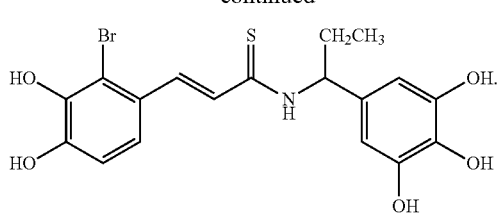

16

16. A pharmaceutical composition, comprising a therapeutically effective amount of at least one compound according to claim 1, and a pharmaceutically acceptable carrier or excipient.

17. A method of inhibiting signal transduction mediated by a protein kinase (PK), comprising the step of contacting said PK with an effective inhibitory amount of at least one compound according to claim 1.

18. The method according to claim 17, wherein said protein kinase is a receptor protein tyrosine kinase (RTK) selected from the group consisting of a platelet-derived growth factor receptor (PDGFR), a fibroblast growth factor receptor (FGFR), a hepatocyte growth factor receptor (HGFR), an insulin receptor, an insulin-like growth factor-1 receptor (IGF-1R), an epidermal growth factor receptor (EGFR), a nerve growth factor receptor (NGFR), a vascular endothelial growth factor receptor (VEGFR), and a macrophage colony stimulating factor (M-CSFR).

19. A method for treating cancer in a subject comprising the step of administering to the subject a therapeutically effective amount of at least one compound according to claim 1, wherein the cancer is selected from the group consisting of ovarian cancer, breast cancer, melanoma, colon cancer, prostate cancer, glioblastoma, hepatocarcinoma, lung cancer, osteosarcoma, multiple myeloma and gastric cancer.

20. A method of inhibiting proliferation of cancer cells, wherein the cancer is selected from the group consisting of an ovarian cancer, breast cancer, melanoma, colon cancer, prostate cancer, glioblastoma, hepatocarcinoma, lung cancer, osteosarcoma, multiple myeloma and gastric cancer, the method comprising contacting the cancer cells with an effective inhibitory amount of at least one compound according to claim 1.

* * * * *